(12) United States Patent
Uchida et al.

(10) Patent No.: US 12,286,414 B2
(45) Date of Patent: Apr. 29, 2025

(54) METHOD FOR PRODUCING HETEROCYCLIDENE ACETAMIDE DERIVATIVE

(71) Applicant: MOCHIDA PHARMACEUTICAL CO., LTD., Tokyo (JP)

(72) Inventors: Hideharu Uchida, Tokyo (JP); Tsutomu Satoh, Tokyo (JP); Bin Zhao, Changzhou (CN); Xiaomin Gu, Changzhou (CN); Jian Luo, Changzhou (CN); Chuan Chen, Changzhou (CN); Xiaofei Cai, Shanghai (CN); Jiajie Ye, Shanghai (CN); Jie Li, Shanghai (CN); Fenglai Sun, Shanghai (CN)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 697 days.

(21) Appl. No.: 17/486,265

(22) Filed: Sep. 27, 2021

(65) Prior Publication Data
US 2022/0009898 A1 Jan. 13, 2022

Related U.S. Application Data

(63) Continuation of application No. PCT/JP2020/022827, filed on Jun. 10, 2020.

(30) Foreign Application Priority Data

Aug. 23, 2019 (CN) .......................... 201910783254.8
Sep. 18, 2019 (WO) .................. PCT/JP2019/036451
Apr. 29, 2020 (CN) .......................... 202010355546.4

(51) Int. Cl.
C07D 311/58 (2006.01)
C07C 29/143 (2006.01)
(Continued)

(52) U.S. Cl.
CPC .......... C07D 311/58 (2013.01); C07C 29/143 (2013.01); C07C 35/23 (2013.01); C07C 213/02 (2013.01); C07C 2602/10 (2017.05)

(58) Field of Classification Search
CPC ... C07D 311/58; C07D 311/02; C07C 29/143; C07C 35/23; C07C 213/02;
(Continued)

(56) References Cited

U.S. PATENT DOCUMENTS 5,041,673 A 8/1991 d'Orchymont et al.
5,136,103 A 8/1992 Fried
(Continued)

FOREIGN PATENT DOCUMENTS

CN 101228131 A 7/2008
CN 101589038 A 11/2009
(Continued)

OTHER PUBLICATIONS

PCT inter. 2002059107, Aug. 2002, abstract (Year: 2002).*
(Continued)

*Primary Examiner* — Taylor V Oh
(74) *Attorney, Agent, or Firm* — Birch, Stewart, Kolasch & Birch, LLP

(57) ABSTRACT

The present invention provides, a novel method for producing a compound represented by formula (I) and a novel method for producing a compound represented by formula (B) or a salt thereof, which are intermediates in the production of formula (I).

7 Claims, 3 Drawing Sheets

(51) Int. Cl.
  *C07C 35/23* (2006.01)
  *C07C 213/02* (2006.01)
(58) Field of Classification Search
  CPC ... C07C 2602/10; C07C 35/52; C07C 209/10;
    C07C 215/70; C07C 269/04; C07C
    269/06; C07C 271/30; C07C 29/159;
    C07C 215/86; C07B 61/00; C07B 53/00;
    C07B 2200/07; C12P 17/06; C12P 7/02;
    C12P 7/04; C12Y 101/01
  USPC ............................................................ 549/407
  See application file for complete search history.

(56) References Cited

U.S. PATENT DOCUMENTS

| | | | |
|---|---|---|---|
| 5,225,339 | A | 7/1993 | Wong et al. |
| 5,342,767 | A | 8/1994 | Wong et al. |
| 2003/0135045 | A1 | 7/2003 | Fisher et al. |
| 2004/0082043 | A1 | 4/2004 | Yadav et al. |
| 2008/0287428 | A1 | 11/2008 | Uchida et al. |
| 2010/0016285 | A1 | 1/2010 | Uchida et al. |
| 2011/0003795 | A1 | 1/2011 | Frank et al. |

FOREIGN PATENT DOCUMENTS

| | | |
|---|---|---|
| CN | 107880058 A | 4/2018 |
| CN | 108276380 A | 7/2018 |
| CN | 109956872 A | 7/2019 |
| EP | 0 343 830 A2 | 11/1989 |
| EP | 1 908 753 A1 | 4/2008 |
| JP | 2-233650 A | 9/1990 |
| JP | 2012-526061 A | 10/2012 |
| JP | 6830569 B1 | 2/2021 |
| JP | 7113098 B2 | 8/2022 |
| RU | 2 196 139 C2 | 1/2003 |
| WO | WO 96/21452 A1 | 7/1996 |
| WO | WO 02/059107 A1 | 8/2002 |
| WO | WO 03/095420 A1 | 11/2003 |
| WO | WO 2005/040100 A1 | 5/2005 |
| WO | WO 2005/040119 A1 | 5/2005 |
| WO | WO 2007/010383 A1 | 1/2007 |
| WO | WO 2008/013949 A2 | 1/2008 |
| WO | WO 2009/050289 A2 | 4/2009 |
| WO | WO 2009/055749 A1 | 4/2009 |
| WO | WO 2010/010935 A1 | 1/2010 |
| WO | WO 2010/038803 A1 | 4/2010 |
| WO | WO 2010/045401 A1 | 4/2010 |
| WO | WO 2010/045402 A1 | 4/2010 |
| WO | WO 2010/127855 A1 | 11/2010 |
| WO | WO 2018/205948 A1 * | 11/2018 |

OTHER PUBLICATIONS

Decision to Grant a Patent for Japanese Patent Application No. 2021-009393, dated Jun. 28, 2022, with English translation.
Japanese Office Action for Japanese Application No. 2021-009393, dated Dec. 21, 2021, with English translation.
Bsharat et al., "Asymmetric Reduction of Substituted 2-Tetralones by Thermoanaerobacter pseudoethanolicus Secondary Alcohol Dehydrogenase," ChemCatChem (2017), vol. 9, pp. 1487-1493.
Extended European Search Report issued Sep. 26, 2022, in European Patent Application No. 20859098.4.
Russian Notice of Allowance and Search Report for corresponding Russian Application No. 2022102921, dated Dec. 4, 2023, with English translation.
Japanese Notice of Allowance with Allowed Claims for Japanese Application No. 2022-117222, dated Jul. 4, 2023, with an English translation.
4th Edition Experimental Chemistry Course 22, Organic synthesis IV Acid Amino acid Peptide, 1992, pp. 193-309, total 64 pages.
4th Edition Experimental Chemistry Course 26, Organic synthesis VIII, The Chemical Society of Japan, 1992, p. 33, total 5 pages.
Abalain et al., "Selective Synthesis of 1-, and 3-Carbomethoxy 2-Tetralol Stereoisomers by Microbial Reduction of the Corresponding Tetralones", Tetrahedron Asymmetry, Oct. 1, 1996, vol. 7, No. 10, pp. 2983-2996.
Appeal form of Patent Application JP 2020-557359, dated Dec. 22, 2020.
Asai et al., "Practical Synthesis of Photochromic Diarylethenes in Integrated Flow Microreactor Systems;" ChemSusChem, vol. 5, 2012, pp. 339-350, 12 pages total.
Audiger et al., "Ritter Reactions in Flow," ChemSusChem, vol. 5, 2012, pp. 257-260, 4 pages total.
Ayats et al., "A Solid-Supported Organocatalyst for Continuous-Flow Enantioselective Aldol Reactions," ChemSusChem, vol. 5, 2012, pp. 320-325, 6 pages total.
Broda et al., "Application of the Sol-Gel Technique to Develop Synthetic Calcium-Based Sorbents with Excellent Carbon Dioxide Capture Characteristics," ChemSusChem, vol. 5, 2012, pp. 411-418, 8 pages total.
Campbell et al., "The Asymmetric Meerwein-Schmidt-Ponndorf-Verley Reduction of Prochiral Ketones with iPrOH Catalyzed by Al Catalysts", Angew. Chem. Int. Ed., Mar. 15, 2002, vol. 41, No. 6, pp. 1020-1022.
CAS No. 1823867-35-1, Sep. 1, 2021, total 3 pages.
CAS No. 1823929-47-0, Sep. 1, 2021, total 3 pages.
CAS No. 444619-84-5, Sep. 1, 2021, total 3 pages.
CAS No. 920334-15-2, Sep. 1, 2021, total 3 pages.
Chinnusamy et al., "Application of Metal-Based Reagents and Catalysts in Microstructured Flow Devices;" ChemSusChem, vol. 5, 2012, pp. 247-255, 9 pages total.
Contents, Chemsuschem, vol. 5, 2012, pp. 218-226, 9 pages total.
Corey et al., "Highly Enantioselective Borane Reduction of Ketones Catalyzed by Chiral Oxazaborolidines. Mechanism and Synthetic Implications", J. Am. Chem. Soc., Sep. 1, 1987, No. 109, No. 18, pp. 5551-5553.
Cover page, Chemsuschem, vol. 5, 2012, 1 page total.
Cover Picture, Chemsuschem, vol. 5, 2012, 2 pages total.
De Gonzalo et al., "Enzymatic Reduction of Ketones in "Microaqueous" Media Catalyzed by ADH-A from Rhodococcus ruber", Organic Letters, May 1, 2007, vol. 9, No. 11, pp. 2163-2166.
Dencic et al., "Recent Changes in Patenting Behavior in Microprocess Technology and its Possible Use for Gas-Liquid Reactions and the Oxidation of Glucose," ChemSusChem, vol. 5. 2012, pp. 232-245, 14 pages total.
Dibenedetto et al., "Hybrid Technologies for an Enhanced Carbon Recycling Based on the Enzymatic Reduction of CO2 to Methanol in Water: Chemical and Photochemical NADH Regeneration," ChemSusChem, vol. 5, 2012, pp. 373-378, 6 pages total.
Doherty et al., "4-Aminopyrimidine tetrahydronaphthols: A series of novel vanilloid receptor-1 antagonists with improved solubility properties", Bioorganic & Medicinal Chemistry Letters, vol. 18, No. 6, available online Feb. 13, 2008, pp. 1830-1834.
Ellingboe et al., "Antihyperglycemic Activity of Novel Naphthalenyl 3H-1,2,3,5-Oxathiadiazole 2-Oxides", Journal of Medicinal Chemistry, Aug. 1, 1993, vol. 36, No. 17, pp. 2485-2493.
Gürbüz et al., "Conversion of Hemicellulose to Furfural and Levulinic Acid using Biphasic Reactors with Alkylphenol Solvents," ChemSusChem, vol. 5, 2012, pp. 383-387, 5 pages total.
Hill-Cousins et al., "TEMPO-Mediated Electrooxidation of Primary and Secondary Alcohols in a Microfluidic Electrolytic Cell," ChemSusChem, vol. 5, 2012, pp. 326-331, 6 pages total.
Hoffmann, "Homogeneous Photocatalytic Reactions with Organometallic and Coordination Compounds—Perspectives for Sustainable Chemistry," ChemSusChem, vol. 5, 2012, pp. 352-371, 20 pages total.
Hübner et al., "Ultrasound and Microstructures—A Promising Combination?," ChemSusChem, vol. 5, 2012, pp. 279-288, 10 pages total.
International Search Report for PCT/JP2020/022827 mailed on Aug. 18, 2020.
Janeczko et al., "Enantioselective Dynamic Process Reduction of α- and β-Tetralone and Stereoinversion of Resulting Alcohols in a Selected Strain Culture", Current Microbiology, May 22, 2012, vol. 65, No. 2, pp. 189-194.

(56) References Cited

OTHER PUBLICATIONS

Jiang et al., "CuI/4-Hydro-L-proline as a More Effective Catalytic System for Coupling of Aryl Bromides with N-Boc Hydrazine and Aqueous Ammonia", J. Org. Chem., May 11, 2009, vol. 74, No. 12, pp. 4542-4546.
Kim et al., "Ammonium salts as an inexpensive and convenient nitrogen source in the Cu-catalyzed amination of aryl halides at room temperature", Chem. Commun., May 23, 2008, vol. 26, pp. 3052-3054.
Kitamura et al., "Homogeneous Asymmetric Hydrogenation of Functionalized Ketones", J. Am. Chem. Soc., Jan. 1, 1988, vol. 110, No. 2, pp. 629-631.
Kotrappanavar Nataraj et al., "Highly Proton-Selective Biopolymer Layer-Coated Ion-Exchange Membrane for Direct Methanol Fuel Cells," ChemSusChem, vol. 5, 2012, pp. 392-395, 4 pages total.
Kralisch et al., "Transfer of the Epoxidation of Soybean Oil from Batch to Flow Chemistry Guided by Cost and Environmental Issues," ChemSusChem, vol. 5, 2012, pp. 300-311, 12 pages total.
Kurahashi et al., "Room-Temperature, Acid-Catalyzed [2+2] Cycloadditions: Suppression of Side Reactions by using a Flow Microreactor System," ChemSusChem, vol. 5, 2012, pp. 270-273, 4 pages total.
Lai et al., "Stereocontrolled Synthesis of the Sterically Encumbered F Ring of Lancifodilactone G", Organic Letters, May 3, 2008, vol. 10, No. 11, pp. 2115-2118.
Lavandera et al., "An Exceptionally DMSO-Tolerant Alcohol Dehydrogenase for the Stereoselective Reduction of Ketones", ChemSusChem, May 15, 2008, vol. 1, No. 5, pp. 431-436.
Lavandera et al., "Asymmetric anti-Prelog reduction of ketones catalysed by Paracoccus pantotrophus and Comamonas sp. cells via hydrogen transfer", Tetrahedron: Asymmetry, Aug. 27, 2008, vol. 19, No. 16, 2008, pp. 1954-1958.
Lavandera et al., "Stereoselective Bioreduction of Bulky-Bulky Ketones by a Novel ADH from Ralstonia sp.", J. Org. Chem., Jul. 3, 2008, vol. 73, No. 15, pp. 6003-6005.
Lee et al., "Flexible and Platinum-Free Dye-Sensitized Solar Cells with Conducting-Polymer-Coated Graphene Counter Electrodes," ChemSusChem, vol. 5, 2012, pp. 379-382, 4 pages total.
Li et al., "Amine Synthesis through Mild Catalytic Hydrosilylation of Imines using Polymethylhydroxysiloxane and [RuCl2(arene)]2 Catalysts," ChemSusChem, vol. 5, 2012, pp. 396-399, 4 pages total.
Mcpake et al., "Sequential Continuous Flow Processes for the Oxidation of Amines and Azides by using HOF MeCN," ChemSusChem, vol. 5, 2012, pp. 312-319, 8 pages total.
Musa et al., "Asymmetric Reduction and Oxidation of Aromatic Ketones and Alcohols Using W110A Secondary Alcohol Dehydrogenase from Thermoanaerobacter ethanolicus", J. Org. Chem., Dec. 10, 2006, vol. 72, No. 1, pp. 30-34.
Musa et al., "Xerogel-Encapsulated W110A Secondary Alcohol Dehydrogenase from Thermoanaerobacter ethanolicus Performs Asymmetric Reduction of Hydrophobic Ketones in Organic Solvents", Angew. Chem. Int. Ed., Apr. 12, 2007, vol. 46, No. 17, pp. 3091-3094.
News Spotlights on our Sister Journals, ChemSusChem, vol. 5, 2012, pp. 228-230, 3 pages total.
Nishiyama et al., "Highly Enantioselective Hydrosilylation of Ketones with Chiral and C2-Symmetrical Bis( oxazolinyl)pyridine-Rhodium Catalysts", Organometallics, Feb. 1, 1991, vol. 10, No. 2, pp. 500-508.
Notice of Allowance for Patent Application JP 2020-557359, dated Jan. 5, 2021.
Ohira et al., "Design of Cellulose Dissolving Ionic Liquids Inspired by Nature," ChemSusChem, vol. 5, 2012, pp. 388-391, 4 pages total.
Ötvös et al., "Highly Efficient 1,4-Addition of Aldehydes to Nitroolefins: Organocatalysis in Continuous Flow by Solid-Supported Peptidic Catalysts," ChemSusChem, vol. 5, 2012, pp. 266-269, 4 pages total.
Pan et al., "New Biobased High Functionality Polyols and Their Use in Polyurethane Coatings," ChemSusChem, vol. 5, 2012, pp. 419-429, 11 pages total.

Patil et al., "Enantioselective bioreduction of cyclic alkanones by whole cells of Candida Species", Biocatalysis and Biotransformation, Mar. 25, 2013, vol. 31, No. 3, pp. 123-131.
Petersen et al., "The Oxygen-Mediated Synthesis of 1,3-Butadiynes in Continuous Flow: Using Teflon AF-2400 to Effect Gas/Liquid Contact," ChemSusChem, vol. 5, 2012, pp. 274-277, 4 pages total.
Phukan et al., "Biocatalytic Preparative Method of Asymmetric Alcohols Using Lycopersicumesculentum (Tomato)", International Journal of ChemTech Research, Jan.-Mar. 2012, vol. 4, No. 1, pp. 203-207.
Pivovarova et al., "Synthesis and Mesomorphic Properties of N-(4-Metoxibenziliden)-4'-Butylaniline Derivatives With Fluorine Atoms in the Side Chain", Ukrainskii Khimiche skii Zhurnal (Russian Edition), 1987, vol. 53, No. 12, pp. 1299-1302.
Pollard et al., "Synthesis of Chiral sec-Alcohols by Ketone Reduction", Practical Methods for Biocatalysis and Biotransformations, Chapter 9, Dec. 15, 2009, pp. 273-294.
Reviews page, Chemsuschem, vol. 5, 2012, p. 439, 1 page total.
Schätzle et al., "Tetrahydroxynaphthalene Reductase: Catalytic Properties of an Enzyme Involved in Reductive Asymmetric Naphthol Dearomatization", Angew. Chem. Int. Ed., Feb. 3, 2012, vol. 51, No. 11, pp. 2643-2646.
Shen et al., "Palladium-Catalyzed Coupling of Ammonia and Lithium Amide with Aryl Halides", J. Am. Chem. Soc., Jul. 12, 2006, vol. 128, No. 31, pp. 10028-10029.
Sorgedrager et al., "Asymmetric Carbonyl Reductions with Microbial Ketoreductases", Advanced Synthesis & Catalysis, Oct. 7, 2008, vol. 350 (14+15), pp. 2322-2328.
Spaccini et al., "Organocatalyzed Epoxidation of Alkenes in Continuous Flow using a Multi-Jet Oscillating Disk Reactor," ChemSusChem, vol. 5, 2012, pp. 261-265, 5 pages total.
Stampfer et al., "Biocatalytic Asymmetric Hydrogen Transfer Employing Rhodococcus ruber DSM 44541", J. Org. Chem., Dec. 5, 2002, vol. 68, No. 2, pp. 402-406.
Stjernlöf et al., "5-, 6-, 7- And 8-amino-2-(N,N-di-n-propylamino)-1,2,3,4-tetrahydronaphthalenes: centrally acting DA and 5-HT1A agonists"; European Journal of Medicinal Chemistry, 1993, vol. 28, No. 9, pp. 693-701.
Surry et al., "Selective Palladium-Catalyzed Arylation of Ammonia: Synthesis of Anilines as Well as Symmetrical and Unsymmetrical Di- and Triarylamines", J. Am. Chem. Soc., Aug. 2, 2007; vol. 129, No. 34, pp. 10354-10355.
Swizdor et al., "Asymmetric reduction of tetralones and their methoxy derivatives by Fusarium culmorum", Biocatalysis and Biotransformation, vol. 27, No. 3, May-Jun. 2009, pp. 179-185.
Swizdor et al., "Didymosphaeria igniaria: a new microorganism useful for the enantioselective reduction of aryl-aliphatic ketones", Journal of Industrial Microbiology and Biotechnology, vol. 37, No. 11, available online Jun. 11, 2010, pp. 1121-1130.
Tang et al., "Hollow Carbon Nanospheres with a High Rate Capability for Lithium-Based Batteries," ChemSusChem, vol. 5, 2012, pp. 400-403, 4 pages total.
Van Den Broek et al., "Prilezhaev Dihydroxylation of Olefins in a Continuous Flow Process," ChemSusChem, vol. 5, 2012, pp. 289-292, 4 pages total.
Vitale et al., "Screening on the use of Kluyveromyces marxianus CBS 6556 growing cells as enantioselective biocatalysts for ketone reductions", Tetrahedron: Asymmetry, Dec. 15, 2011, vol. 22, No. 23, pp. 1985-1993.
Wiles et al., "Solid-Supported Gallium Triflate: An Efficient Catalyst for the Three-Component Ketonic Strecker Reaction," ChemSusChem, vol. 5, 2012, pp. 332-338, 7 pages total.
Wirth, "Flow Chemistry: Enabling Technology in Drug Discovery and Process Research," ChemSusChem, vol. 5, 2012, pp. 215-216, 2 pages total.
Written Opinion of the International Searching Authority for PCT/JP2020/022827 (PCT/ISA/237) mailed on Aug. 18, 2020.
Xia et al., "A Very Simple Copper-Catalyzed Synthesis of Anilines by Employing Aqueous Ammonia", Angew. Chem. Int. Ed., Dec. 22, 2008, vol. 48, No. 2, pp. 337-339.

(56) References Cited

OTHER PUBLICATIONS

Yamada et al., "Development of Polymeric Palladium-Nanoparticle Membrane-Installed Microflow Devices and their Application in Hydrodehalogenation," ChemSusChem, vol. 5, 2012, pp. 293-299, 7 pages total.

Yang et al., "Synthesis of Furfural from Xylose, Xylan, and Biomass Using AlCl3 6H2O in Biphasic Media via Xylose Isomerization to Xylulose," ChemSusChem, vol. 5, 2012, pp. 405-410, 6 pages total.

Zakzeski et al., "Solid Acid-Catalyzed Cellulose Hydrolysis Monitored by In Situ ATR-IR Spectroscopy," ChemSusChem, vol. 5, 2012, pp. 430-437, 8 pages total.

Zhu et al., "A recombinant ketoreductase tool-box. Assessing the substrate selectivity and stereoselectivity toward the reduction of β-ketoesters", Tetrahedron, Nov. 7, 2005, vol. 62, pp. 901-905.

Chinese Office Action and Search Report for Chinese Application No. 202080058490.4, dated Aug. 2, 2023, with an English translation.

Pujala et al., "Discovery of Pyrazolopyrimidine Derivatives as Novel Dual Inhibitors of BTK and PI3Kσ", ACS Medicinal Chemistry Letters, vol. 7, Oct. 28, 2016, pp. 1161-1166 (48 pages total).

Chinese Office Action for corresponding Chinese Application No. 202080058490.4, dated Jan. 4, 2024, with English translation.

Blotny et al., "Synthesis of 5,7- and 6,7-Dinitro-2-Tetralones," Synthetic Communications, vol. 28, No. 20, 1998, pp. 3865-3875.

Extended European Search Report for European Application No. 24184274.9, dated Nov. 13, 2024.

Korean Office Action for Korean Application No. 10-2022-7004193, dated Dec. 18, 2024, with an English translation.

\* cited by examiner

[Fig. 1]
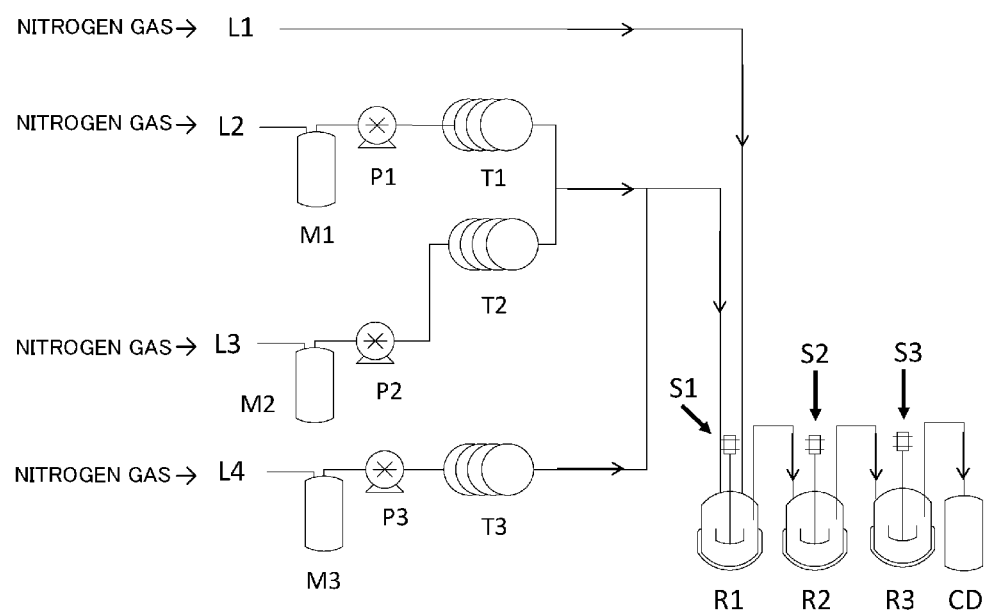

[Fig. 2]
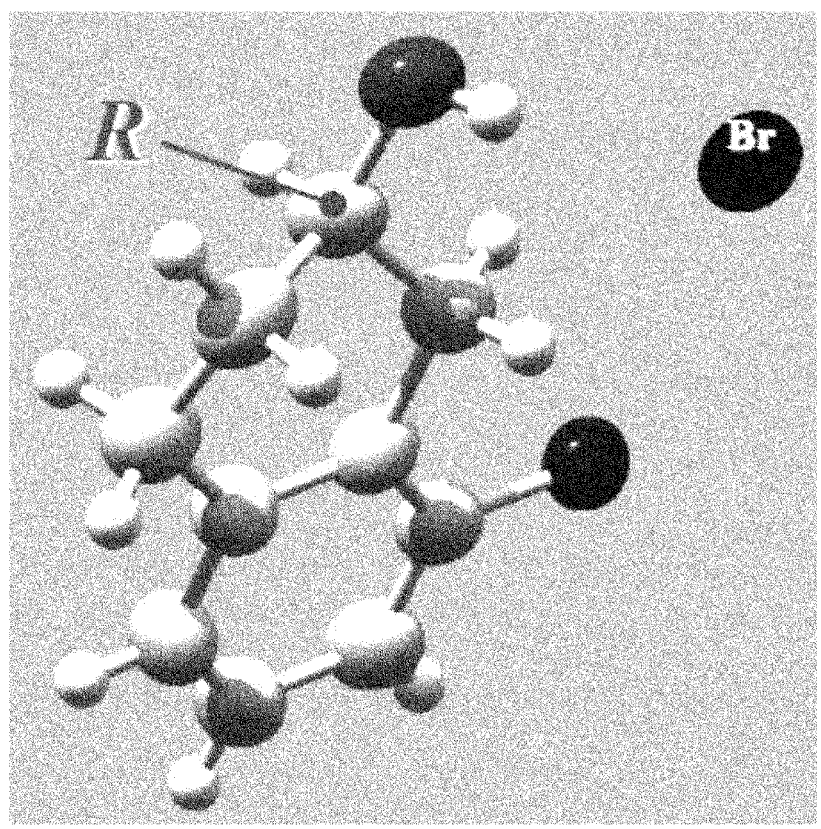

[Fig. 3]
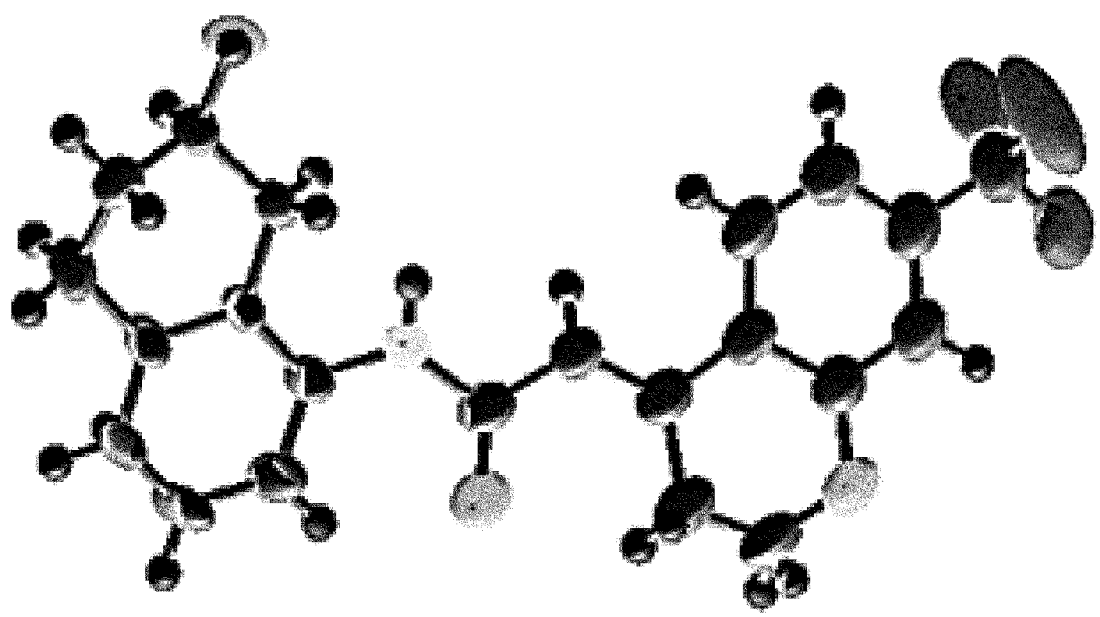

METHOD FOR PRODUCING HETEROCYCLIDENE ACETAMIDE DERIVATIVE

CROSS REFERENCE TO RELATED APPLICATIONS

This application is Continuation of PCT International Application No. PCT/JP2020/022827, filed on Jun. 10, 2020, which claims priority under 35 U.S.C. 119(a) to patents application Nos. 201910783254.8, filed in China on Aug. 23, 2019; PCT/JP2019/036451, filed in Japan on Sep. 18, 2019; and 202010355546.4, filed in China on Apr. 29, 2020, all of which are hereby expressly incorporated by reference into the present application.

TECHNICAL FIELD

The present invention relates to a new method for producing (E)-2-(7-trifluoromethylchroman-4-ylidene)-N-((7R)-7-hydroxy-5,6,7,8-tetrahydronaphthalen-1-yl)acetamide represented by Formula (I) which is a heterocyclidene acetamide derivative. Furthermore, the present invention relates to a new method for producing (R)-8-amino-1,2,3,4-tetrahydronaphthalen-2-ol represented by Formula (B) or a salt thereof, which is an intermediate useful for producing the compound represented by Formula (I).

BACKGROUND ART (E)-2-(7-trifluoromethylchroman-4-ylidene)-N-((7R)-7-hydroxy-5,6,7,8-tetrahydronaphthalen-1-yl)acetamide represented by Formula (I) is a transient receptor potential vanilloid 1 (TRPV1) antagonist, and is anticipated as a preventive and/or therapeutic agent for diseases involving the TRPV1 receptor (for example, pain (for example, neuropathic pain, diabetic neuralgia, postoperative pain, osteoarthrosis, rheumatoid arthritis pain, inflammatory pain, cancer pain, migraine and the like), nervous disorders, nerve damage, neurodegeneration, chronic obstructive pulmonary disease, asthma, rhinitis, inflammation of mucous membranes such as in the eyes, nervous skin disease, inflammatory skin disease, allergic disease, urinary incontinence, urge incontinence, overactive bladder, cystitis, pruritus, and the like) (Patent Literature 1).

[C1]

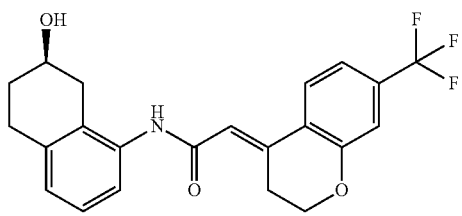

WO 2007/010383 (Patent Literature 1) discloses a method for producing the compound represented by Formula (I). In the document, the compound represented by Formula (I) is produced in steps of <Step 1> to <Step 3> shown in the following (scheme A).

<Step 1> A compound represented by Formula (IM-k) is obtained by performing a condensation reaction using 8-amino-3,4-dihydronaphthalen-2(1H)-one (Formula (IM-3)) produced according to a method known from a document (for example, WO 2005/040100 (Patent Literature 2) and the like) and (E)-2-(7-(trifluoromethyl)chroman-4-ylidene)acetic acid (Formula (CA-1) in CAS No. 920334-15-2, Non Patent Literature 1) and a condensing agent (1-ethyl-3-(3-dimethylaminopropyl)carbodiimide hydrochloride (EDCI.HCl)).

<Step 2> The compound represented by Formula (IM-k) is reduced with sodium borohydride to obtain a compound represented by Formula (I-Rac).

<Step 3> The compound represented by Formula (I-Rac) is optically resolved on an optically active column to obtain a compound represented by Formula (I), and a compound represented by Formula (I-S) which is an isomer thereof.

However, in this production method, the compound represented by Formula (I) is obtained by performing the column resolution in the final step, and it is difficult to reuse the compound represented by Formula (I-S) obtained after the column resolution.

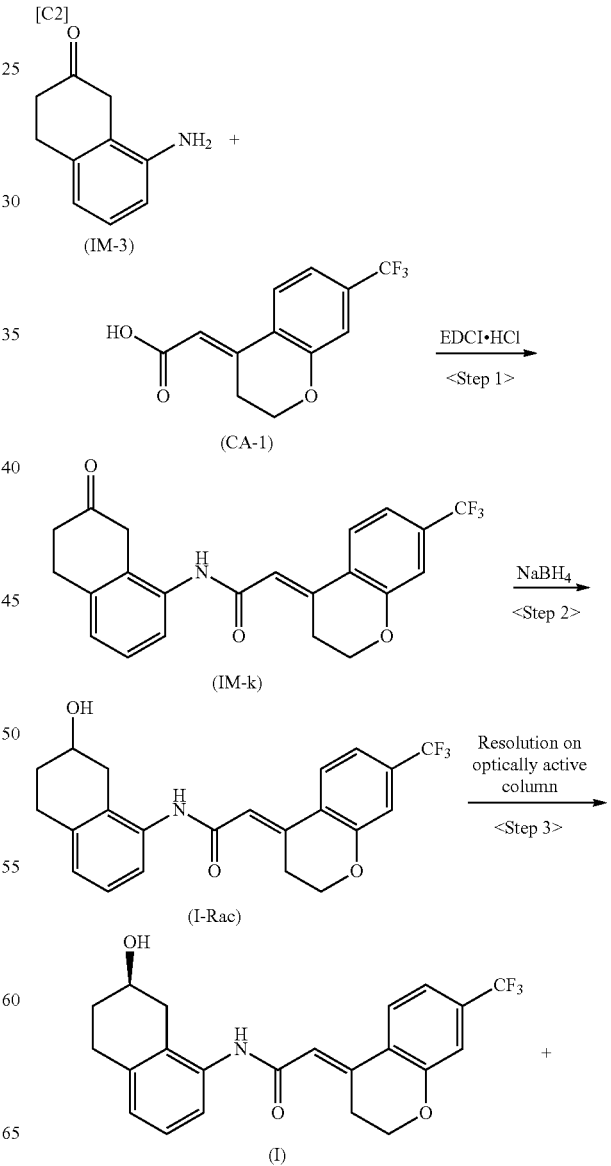

(Scheme A)

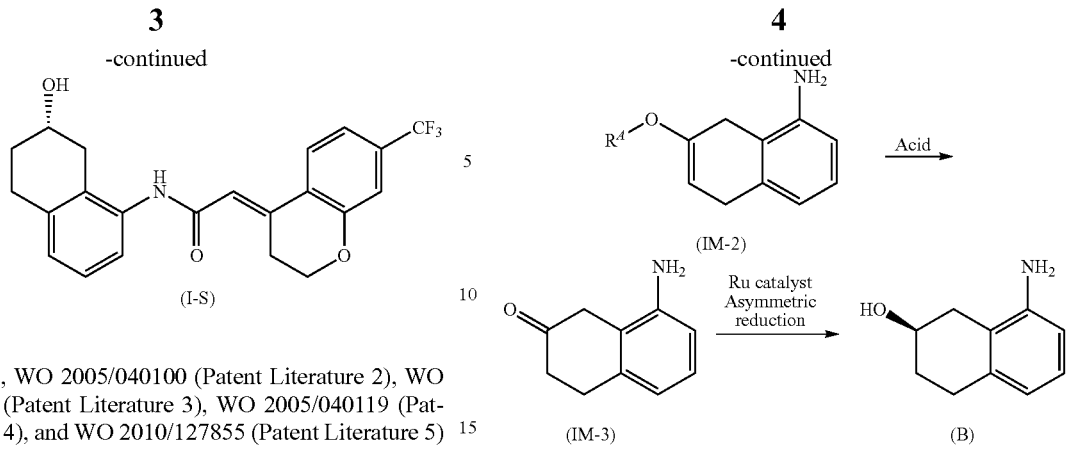

Meanwhile, WO 2005/040100 (Patent Literature 2), WO 2003/095420 (Patent Literature 3), WO 2005/040119 (Patent Literature 4), and WO 2010/127855 (Patent Literature 5) disclose methods for producing the compound represented by Formula (B), which corresponds to a partial structural formula of Formula (I).

[C3]

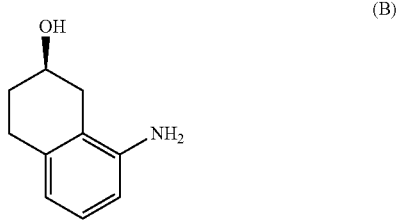

In these literatures, 8-amino-3,4-dihydronaphthalen-2(1H)-one (Formula (IM-3)) is obtained through reactions of alkylation of a phenol group, Birch reduction, and deprotection of an alkyl group using 8-aminonaphthalen-2-ol (Formula (SM-1)) as a starting material, and thereby the compound represented by Formula (B) is produced by asymmetrically reduction of it in the presence of a Ru catalyst (scheme 1).

However, in these production methods, the Birch reduction is used in one step, and the metal (Ru) catalyst is used in the asymmetric reduction in the final step, therefore a step of reducing a residual rate of the metal (Ru) in the obtained compound is required.

(Scheme 1)

[C4]

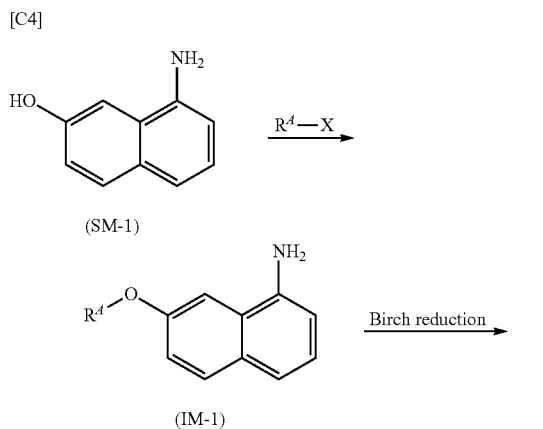

$R^A$ = alkyl group (Me group, Et group, etc.)
X = halogen atom

Furthermore, WO 2009/050289 (Patent Literature 6), WO 2010/045401 (Patent Literature 7), and WO 2010/045402 (Patent Literature 8) also disclose methods for producing the compound represented by Formula (B). In these literatures, the compound represented by Formula (B) is produced by a resolution using an optically active column after induced into racemic 8-amino-1,2,3,4-tetrahydronaphthalen-2-ol (Formula A) by selectively reducing a naphthalene ring using 8-aminonaphthalen-2-ol (Formula (SM-1)) as a starting material (scheme 2).

However, in this production method, it is difficult to reuse other isomers (S-forms) obtained after the column resolution.

(Scheme 2)

[C5]

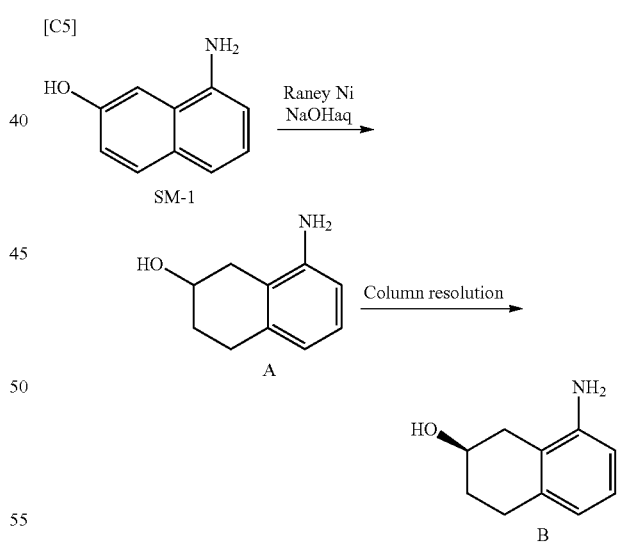

Furthermore, WO 2009/055749 (Patent Literature 9) also discloses a method for producing the compound represented by Formula (B). In this literature, the compound represented by Formula (B) is produced by column resolution of the diastereomer obtained after diastereomeric resolution of a chiral auxiliary introduced racemate represented by Formula (A) (scheme 3).

However, also in this production method, it is difficult to reuse other isomers (S-forms) obtained after the column resolution.

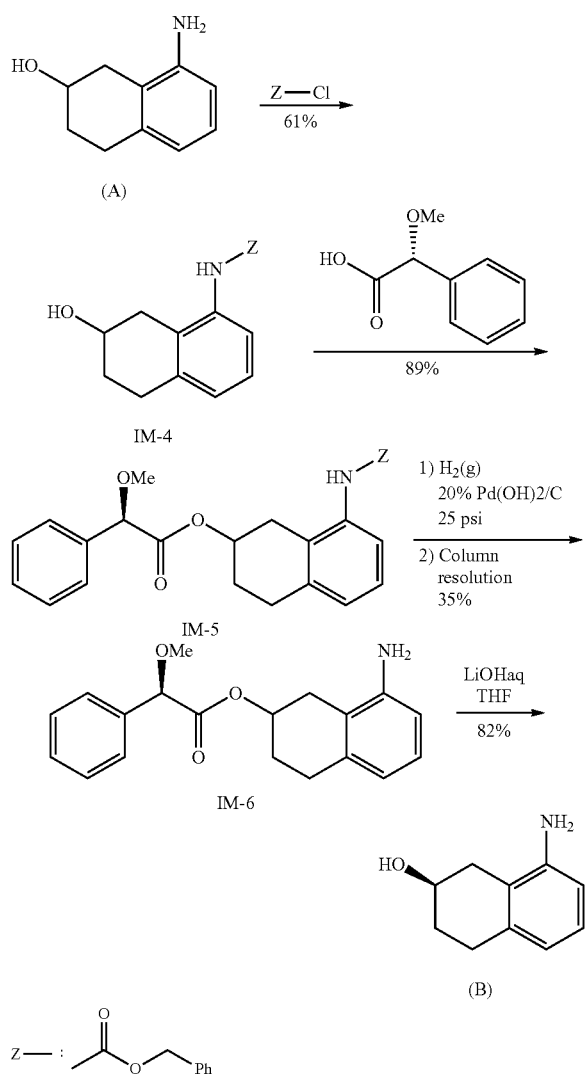

(Scheme 3)

The methods for producing the compound represented by Formula (B) disclosed in the respective literatures have issues such as types of reactions in the production process, reagents to be used, and difficulty in reuse of other isomers obtained after resolving a racemate or diastereoisomer on a column. Therefore, an improved production method is required for large-scale synthesis or industrial production of the compound represented by Formula (B). That is, when considering large-scale synthesis or industrial production of the compound represented by Formula (B), it is required to find a new production method different from the production methods described in the respective literatures. Since a production method for large-scale synthesis of the compound represented by Formula (B) in a high yield and high optical purity has not yet been found, it is thought that the above-mentioned issues in the production of the compound represented by Formula (B) can be solved if a method for a large scale synthesis of the compound represented by Formula (B) in fewer steps, high chemical yield, and high optical purity is found.

U.S. Pat. No. 5,136,103 (Patent Literature 10) and the like disclose a method for oxidizing a secondary alcohol to a ketone using 2,2,6,6-tetramethylpiperidine-1-oxyl radical (TEMPO) as an oxidant. However, a TEMPO oxidation reaction in which 1,2,3,4-tetrahydronaphthalene (for example, tert-butyl-(7-hydroxy-5,6,7,8-tetrahydronaphthalen-1-yl)carbamate and the like) which has a substituted amino group and a hydroxyl group in a molecule is used as a raw material is not known. Furthermore, a TEMPO oxidation reaction by flow chemistry (flow reaction) in which the compound is used as a raw material is also not known.

U.S. Pat. No. 5,225,339 (Patent Literature 11) and U.S. Pat. No. 5,342,767 (Patent Literature 12) disclose reduction of ketones by a reductase derived from *Lactobacillus* kefir, but an enzymatic reduction adapted to keto compounds such as protecting group-substituted amino-3,4-dihydronaphthalen-2(1H)-one or β-tetralone is not disclosed.

Advanced Synthesis & Catalysis, 350 (14+15), p 2322-2328, 2008 (Non Patent Literature 2) discloses enzymatic reduction of ketones of α- or β-tetralone (reductase: derived from *Lactobacillus* kefir). However, it is clearly stated that a reductive reaction of ketones of β-tetralone does not proceed when a reductase derived from *Lactobacillus* kefir is used.

WO 2018/205948 (Patent Literature 13) discloses 8-bromo-1,2,3,4-tetrahydronaphthalen-2-ol (CAS No. 444619-84-5, Non Patent Literature 3) and its production method, but (R)-8-bromo-1,2,3,4-tetrahydronaphthalen-2-ol, which is a chiral form thereof, and its production method are not known.

CAS Registry discloses 8-fluoro-1,2,3,4-tetrahydronaphthalen-2-ol (CAS No. 1823867-35-1, Non Patent Literature 4), but (R)-8-fluoro-1,2,3,4-tetrahydronaphthalen-2-ol, which is a chiral form thereof, and its production method are not known. Furthermore, CAS Registry discloses 8-chloro-1,2,3,4-tetrahydronaphthalen-2-ol (CAS No. 1823929-47-0, Non Patent Literature 5), but (R)-8-chloro-1,2,3,4-tetrahydronaphthalen-2-ol, which is a chiral form thereof, and its production method are not known.

Bioorganic & Medicinal Chemistry Letters, 18 (6), p 1830-1834, 2008 (Non Patent Literature 6) discloses a method for producing 8-amino-6-fluoro-1,2,3,4-tetrahydronaphthalen-2-ol (yield 18%) by an amination reaction of 8-bromo-6-fluoro-1,2,3,4-tetrahydronaphthalen-2-ol with a Pd catalyst ($Pd_2(dba)_3$) and tert-butyl carbamate, and subsequently deprotection of a Boc group.

CITATION LIST

Patent Literature

[Patent Literature 1] WO 2007/010383
[Patent Literature 2] WO 2005/040100
[Patent Literature 3] WO 2003/095420
[Patent Literature 4] WO 2005/040119
[Patent Literature 5] WO 2010/127855
[Patent Literature 6] WO 2009/050289
[Patent Literature 7] WO 2010/045401
[Patent Literature 8] WO 2010/045402
[Patent Literature 9] WO 2009/055749
[Patent Literature 10] U.S. Pat. No. 5,136,103
[Patent Literature 11] U.S. Pat. No. 5,225,339
[Patent Literature 12] U.S. Pat. No. 5,342,767
[Patent Literature 13] WO 2018/205948

Non Patent Literature

[Non Patent Literature 1] CAS No. 920334-15-2
[Non Patent Literature 2] Advanced Synthesis & Catalysis, 350 (14+15), p 2322-2328, 2008
[Non Patent Literature 3] CAS No. 444619-84-5
[Non Patent Literature 4] CAS No. 1823867-35-1
[Non Patent Literature 5] CAS No. 1823929-47-0
[Non Patent Literature 6] Bioorganic & Medicinal Chemistry Letters, 18(6), p 1830-1834, 2008

SUMMARY OF INVENTION

Technical Problem

Under such circumstances, a new method for producing the above-mentioned compound represented by Formula (I) has been required.

Solution to Problem

The inventors of the present invention have repeatedly conducted extensive research in order to solve the above-described problems. As a result, the inventors have found a new method for easily producing the compound represented by Formula (I) in a high yield, and completed the present invention based on this finding. That is, the inventors have found a new method for producing the compound represented by Formula (I) by a condensation reaction of a carboxylic acid represented by Formula (CA-1) and an amino alcohol represented by Formula (B) or a salt thereof using DMT-MM (4-(4,6-dimethoxy-1,3,5-triazin-2-yl)-4-methylmorpholinium chloride) (CAS No: 3945-69-5) as a condensation agent (Scheme B).

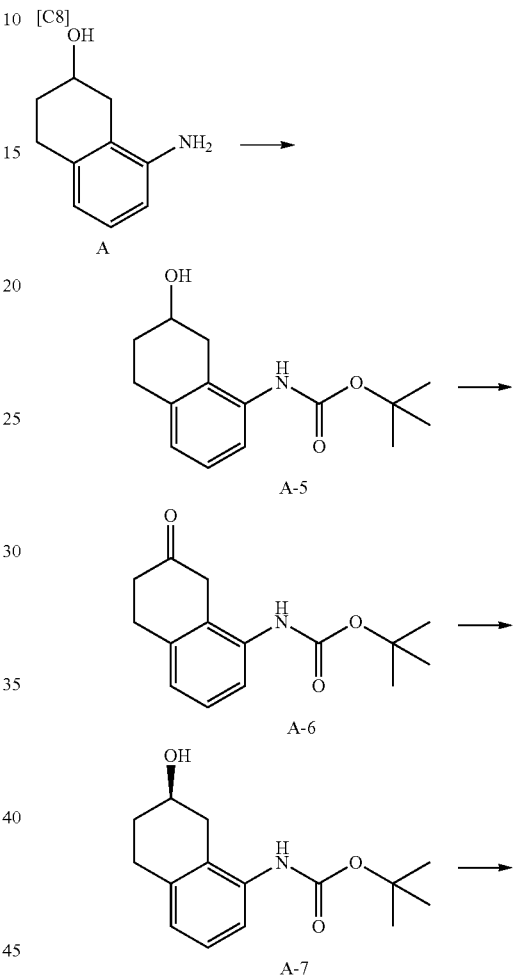

The inventors have further found a new method for producing the compound represented by Formula (B) or a salt thereof, which is an intermediate useful for producing the compound represented by Formula (I), and completed the present invention based on this finding (Scheme C-1).

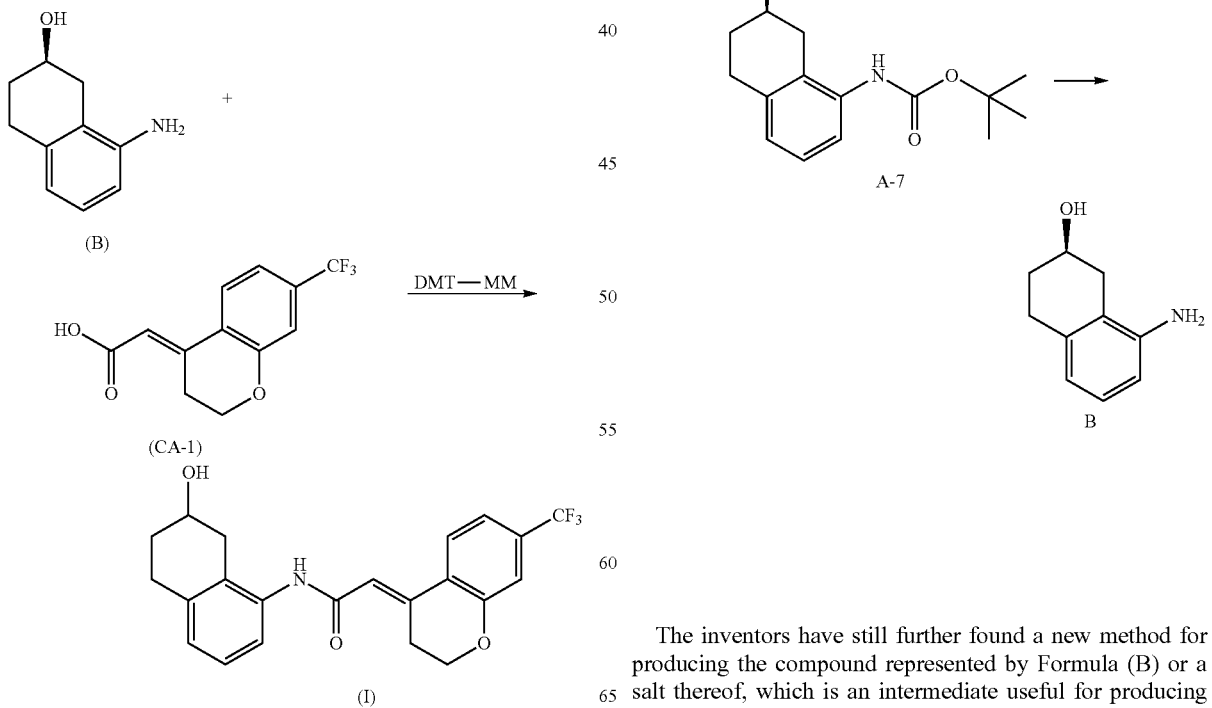

The inventors have still further found a new method for producing the compound represented by Formula (B) or a salt thereof, which is an intermediate useful for producing the compound represented by Formula (I), and completed the present invention based on this finding (Scheme C-2).

(Scheme C-2)

[C9]

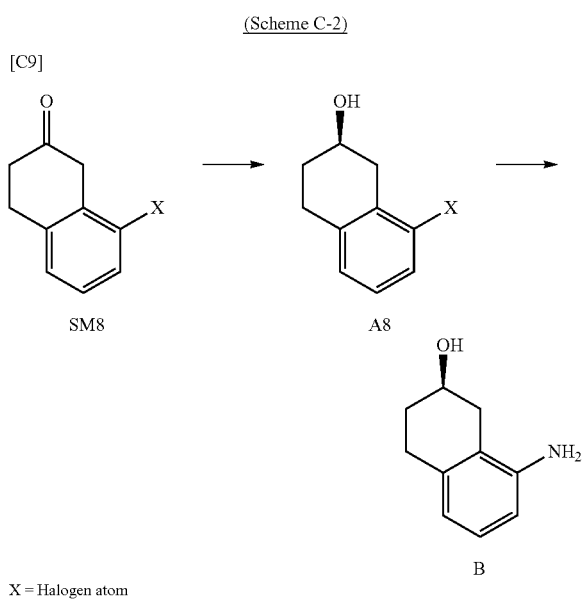

X = Halogen atom

Effect of the Invention

The present invention provides a new method for producing the compound represented by Formula (I), or the compound represented by Formula (B) or a salt thereof. The present invention preferably provides an efficient production method suitable for large-scale synthesis or industrial production of the compound represented by Formula (I), or the compound represented by Formula (B) or a salt thereof. Production methods according to some aspects of the present invention are methods that enable production of the compound represented by Formula (I), or the compound represented by Formula (B) or a salt thereof in a high yield and industrially advantageously, and therefore these methods are highly useful industrially. Furthermore, some other aspects provide new compounds represented by Formulas (A-7) and (A8) which are raw materials for obtaining the compound represented by Formula (B) and a salt thereof.

BRIEF DESCRIPTION OF DRAWINGS

FIG. 1 is an example of a reaction device used in flow chemistry;

FIG. 2 is a figure showing a crystal structure of an HBr salt of a compound represented by Formula (B); and FIG. 3 is a figure showing a crystal structure of a compound represented by Formula (I).

DESCRIPTION OF EMBODIMENTS

Aspects of the Present Invention

A method for producing a compound represented by Formula (I) is provided. Some aspects are a method for producing the compound represented by Formula (I) by using a compound represented by Formula (A) as a starting material. Some other aspects are a method for producing the compound represented by Formula (I) by using a compound represented by Formula (A-5) as a starting material. Still other aspects are a method for producing the compound represented by Formula (I) by using a compound represented by Formula (A-6) as a starting material. Still other aspects are a method for producing the compound represented by Formula (I) by using a compound represented by Formula (A-7) as a starting material.

Still other aspects are a method for producing the compound represented by Formula (I) by using a compound represented by Formula (SM8) as a starting material. Still other aspects are a method for producing the compound represented by Formula (I) by using a compound represented by Formula (SM8-BR) as a starting material. Still other aspects are a method for producing the compound represented by Formula (I) by using a compound represented by Formula (A8) as a starting material. Still other aspects are a method for producing the compound represented by Formula (I) by using a compound represented by Formula (A8-BR) as a starting material. Still other aspects are a method for producing the compound represented by Formula (I) by using a compound represented by Formula (B) as a starting material.

Furthermore, a method for producing the compound represented by Formula (B) or a salt thereof is also provided. Some aspects are a method for producing the compound represented by Formula (B) or a salt thereof by using the compound represented by Formula (A) as a starting material. Some other aspects are a method for producing the compound represented by Formula (B) or a salt thereof by using the compound represented by Formula (A-5) as a starting material. Still other aspects are a method for producing the compound represented by Formula (B) or a salt thereof by using the compound represented by Formula (A-6) as a starting material. Still other aspects are a method for producing the compound represented by Formula (B) or a salt thereof by using the compound represented by Formula (A-7) as a starting material.

Still other aspects are a method for producing the compound represented by Formula (B) or a salt thereof by using the compound represented by Formula (SM8) as a starting material. Still other aspects are a method for producing the compound represented by Formula (B) or a salt thereof by using the compound represented by Formula (SM8-BR) as a starting material. Still other aspects are a method for producing the compound represented by Formula (B) or a salt thereof by using the compound represented by Formula (A8) as a starting material. Still other aspects are a method for producing the compound represented by Formula (B) or a salt thereof by using the compound represented by Formula (A8-BR) as a starting material.

Further still other aspects are a method for producing the compound represented by Formula (A-6) by using the compound represented by Formula (A-5) or Formula (A-7) as a starting material. Further still other aspects are a method for producing the compound represented by Formula (A-7) by using the compound represented by Formula (A-6) as a starting material. Further still other aspects are the compound represented by Formula (A-7).

Still other aspects are a method for producing the compound represented by Formula (A8) by using the compound represented by Formula (SM8) as a starting material. Still other aspects are a method for producing the compound represented by Formula (A8-BR) by using the compound represented by Formula (SM8-BR) as a starting material. Still other aspects are the compound represented by Formula (A8) and the compound represented by Formula (A8-BR).

Hereinafter, each of the aspects will be specifically described.

[1] A first aspect is a method for producing a compound represented by Formula (B) or a salt thereof, the method comprising: tert-butoxycarbonylating an amino group of a compound represented by Formula (A) to obtain a compound represented by Formula (A-5); causing an oxidation reaction of the compound represented by Formula (A-5) to obtain a compound represented by Formula (A-6); asymmetrically reducing the compound represented by Formula (A-6) to obtain a compound represented by Formula (A-7); and deprotecting a tert-butoxycarbonyl group of the compound represented by Formula (A-7) to obtain the compound represented by Formula (B) or a salt thereof.

[2] A second aspect is a method for producing a compound represented by Formula (B) or a salt thereof, the method comprising: causing an oxidation reaction of a compound represented by Formula (A-5) to obtain a compound represented by Formula (A-6); asymmetrically reducing the compound represented by Formula (A-6) to obtain a compound represented by Formula (A-7); and deprotecting a tert-butoxycarbonyl group of the compound represented by Formula (A-7) to obtain the compound represented by Formula (B) or a salt thereof.

Formula (B)
[C10]

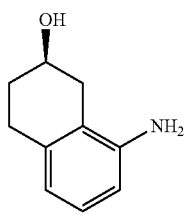

(B)

Formula (A)
[C11]

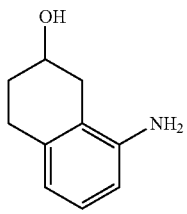

(A)

Formula (A-5)
[C12]

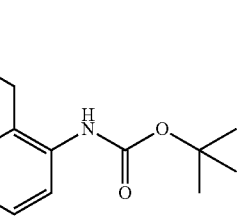

(A-5)

Formula (A-6)
[C13]

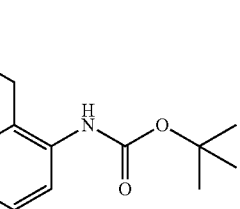

(A-6)

Formula (A-7)
[C14]

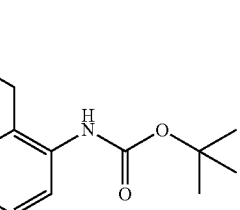

(A-7)

Formula (B)
[C15]

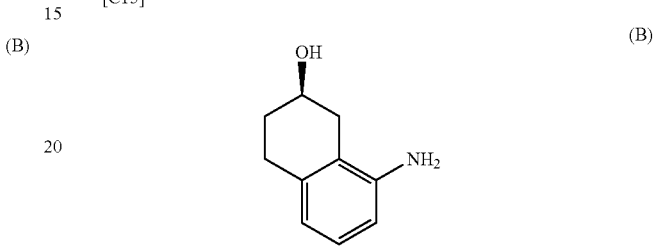

(B)

Formula (A-5)
[C16]

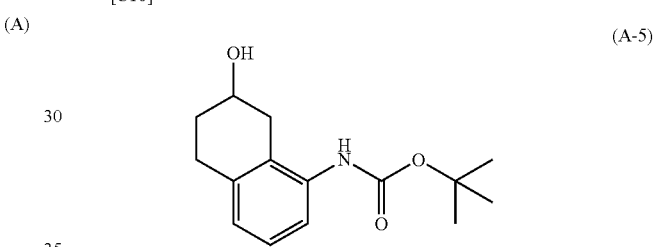

(A-5)

Formula (A-6)
[C17]

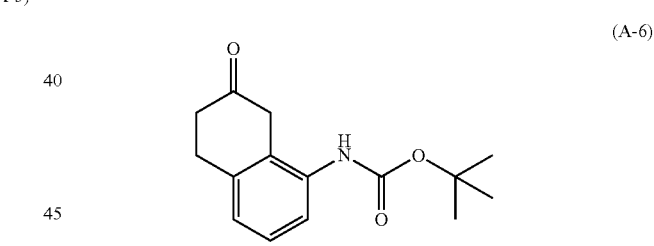

(A-6)

Formula (A-7)
[C18]

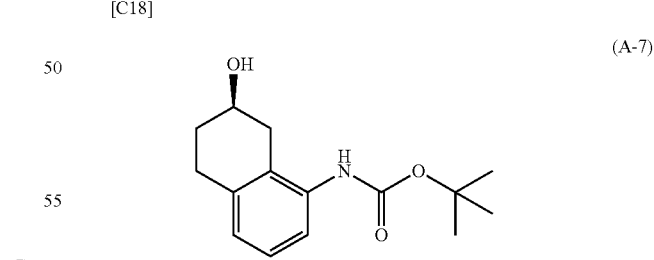

(A-7)

[3] A third aspect is a method for producing a compound represented by Formula (B) or a salt thereof, the method comprising: asymmetrically reducing a compound represented by Formula (A-6) to obtain a compound represented by Formula (A-7); and deprotecting a tert-butoxycarbonyl group of the compound represented by Formula (A-7) to obtain the compound represented by Formula (B) or a salt thereof.

Formula (B)
[C19]

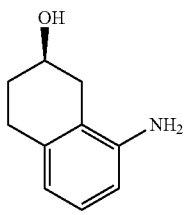

(B)

Formula (A-6)
[C20]

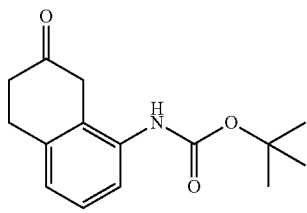

(A-6)

Formula (A-7)
[C21]

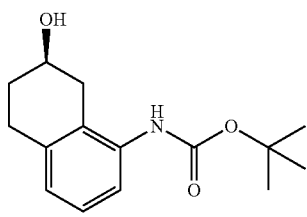

(A-7)

[4] A fourth aspect is a method for producing a compound represented by Formula (B) or a salt thereof, the method comprising: deprotecting a tert-butoxycarbonyl group of a compound represented by Formula (A-7) to obtain the compound represented by Formula (B) or a salt thereof.

Formula (B)
[C22]

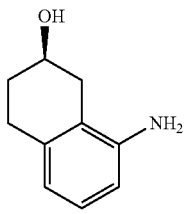

(B)

Formula (A-7)
[C23]

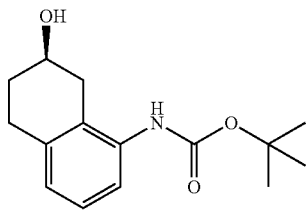

(A-7)

[4B] A 4B-th aspect is a method for producing a salt of a compound represented by Formula (B), the method comprising: adding an acid to the compound represented by Formula (B) to obtain the salt of the compound represented by Formula (B).

Formula (B)
[C24]

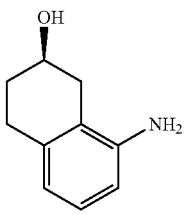

(B)

[4B-1] In the above aspect [4B], the acid used in obtaining a salt of the compound represented by Formula (B) is preferably an inorganic acid or an organic acid, is more preferably an inorganic acid, and is even more preferably hydrobromic acid.

[5] A fifth aspect is a method for producing a compound represented by Formula (A-6), the method comprising: causing an oxidation reaction of a compound represented by Formula (A-5) to obtain a compound represented by Formula (A-6).

Formula (A-6)
[C25]

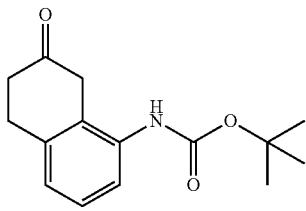

(A-6)

Formula (A-5)
[C26]

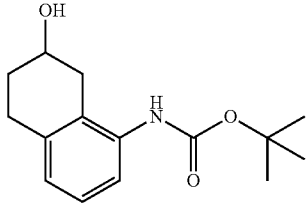

(A-5)

[6] A sixth aspect is a method for producing a compound represented by Formula (A-7), the method comprising: asymmetrically reducing a compound represented by Formula (A-6) to obtain the compound represented by Formula (A-7).

Formula (A-7)
[C27]

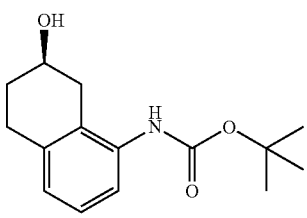

Formula (A-6)
[C28]

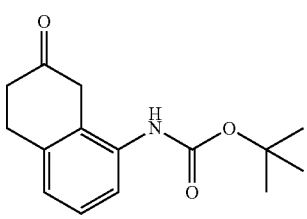

[7] A seventh aspect is a method for producing a compound represented by Formula (I), the method comprising: causing a condensation reaction of a compound represented by Formula (B) or a salt thereof and a compound represented by Formula (CA-1) using DMT-MM as a condensation agent to obtain the compound represented by Formula (I).

Formula (I)
[C29]

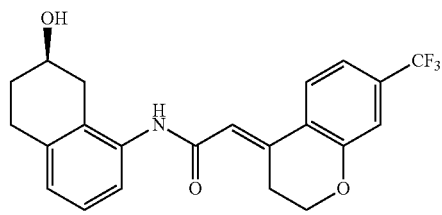

Formula (B)
[C30]

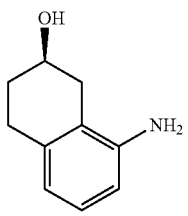

Formula (CA-1)
[C31]

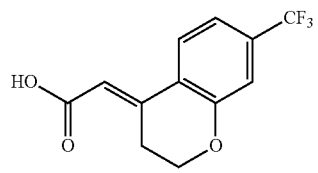

[8] An eighth aspect is a method for producing a compound represented by Formula (I), the method comprising: tert-butoxycarbonylating an amino group of a compound represented by Formula (A) to obtain a compound represented by Formula (A-5); causing an oxidation reaction of the compound represented by Formula (A-5) to obtain a compound represented by Formula (A-6); asymmetrically reducing the compound represented by Formula (A-6) to obtain a compound represented by Formula (A-7); deprotecting a tert-butoxycarbonyl group of the compound represented by Formula (A-7) to obtain a compound represented by Formula (B) or a salt thereof, and causing a condensation reaction of the compound represented by Formula (B) or a salt thereof and a compound represented by Formula (CA-1) using DMT-MM as a condensation agent to obtain the compound represented by Formula (I).

Formula (I)
[C32]

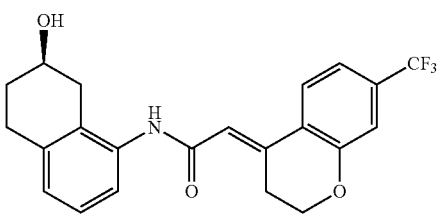

Formula (A)
[C33]

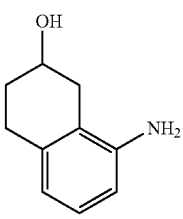

Formula (A-5)
[C34]

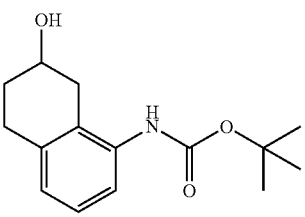

Formula (A-6)
[C35]

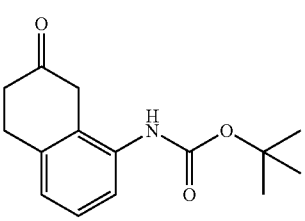

Formula (A-7)
[C36]

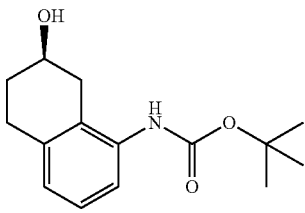
(A-7)

Formula (B)
[C37]

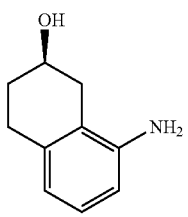
(B)

Formula (CA-1)
[C38]

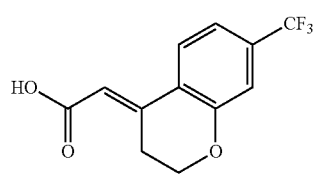
(CA-1)

[9] A ninth aspect is a method for producing a compound represented by Formula (I), the method comprising: causing an oxidation reaction of a compound represented by Formula (A-5) to obtain a compound represented by Formula (A-6); asymmetrically reducing the compound represented by Formula (A-6) to obtain a compound represented by Formula (A-7); deprotecting a tert-butoxycarbonyl group of the compound represented by Formula (A-7) to obtain a compound represented by Formula (B) or a salt thereof, and causing a condensation reaction of the compound represented by Formula (B) or a salt thereof and a compound represented by Formula (CA-1) using DMT-MM as a condensation agent to obtain the compound represented by Formula (I).

Formula (I)
[C39]

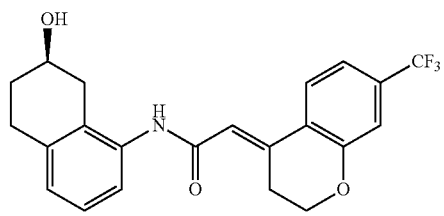
(I)

Formula (A-5)
[C40]

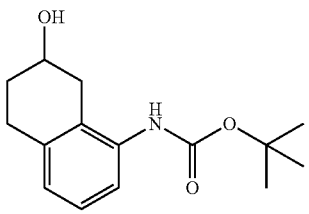
(A-5)

Formula (A-6)
[C41]

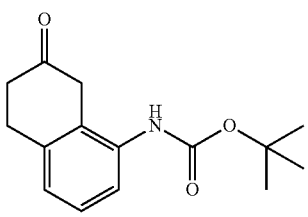
(A-6)

Formula (A-7)
[C42]

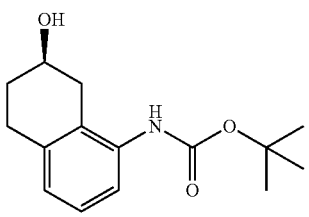
(A-7)

Formula (B)
[C43]

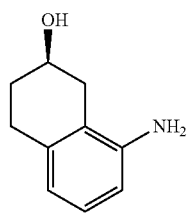
(B)

Formula (CA-1)
[C44]

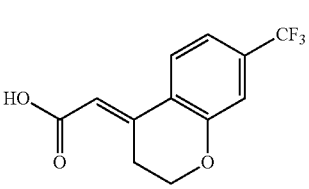
(CA-1)

[10] A tenth aspect is a method for producing a compound represented by Formula (I), the method comprising: asymmetrically reducing a compound represented by Formula (A-6) to obtain a compound represented by Formula (A-7); deprotecting a tert-butoxycarbonyl group of the compound represented by Formula (A-7) to obtain a compound represented by Formula (B) or a salt thereof, and causing a condensation reaction of the compound represented by Formula (B) or a salt thereof and a compound represented by Formula (CA-1) using DMT-MM as a condensation agent to obtain the compound represented by Formula (I).

Formula (I)
[C45]

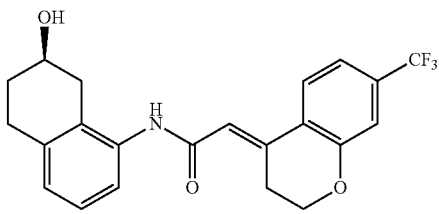
(I)

Formula (A-6)
[C46]

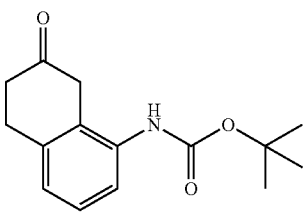
(A-6)

Formula (A-7)
[C47]

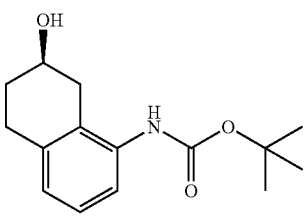
(A-7)

Formula (B)
[C48]

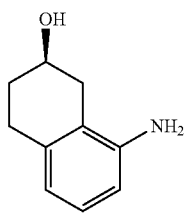
(B)

Formula (CA-1)
[C49]

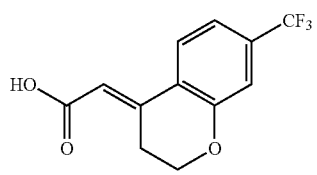
(CA-1)

[11] An eleventh aspect is a method for producing a compound represented by Formula (I), the method comprising: deprotecting a tert-butoxycarbonyl group of a compound represented by Formula (A-7) to obtain a compound represented by Formula (B) or a salt thereof, and causing a condensation reaction of the compound represented by Formula (B) or a salt thereof and a compound represented by Formula (CA-1) using DMT-MM as a condensation agent to obtain the compound represented by Formula (I).

Formula (I)
[C50]

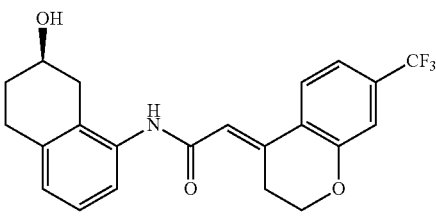
(I)

Formula (A-7)
[C51]

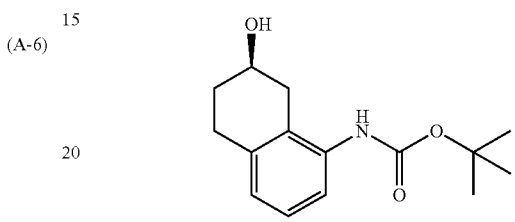
(A-7)

Formula (B)
[C52]

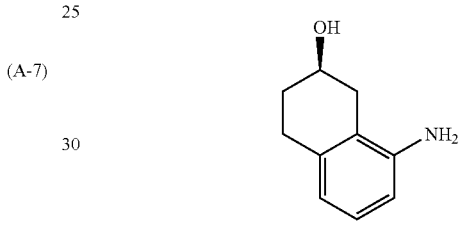
(B)

Formula (CA-1)
[C53]

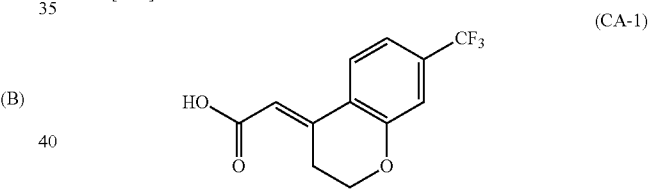
(CA-1)

[12] A twelfth aspect is a compound represented by Formula (A-7).

[C54]

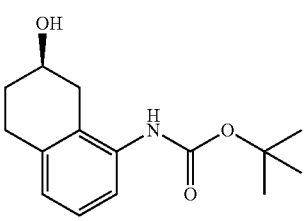
(A-7)

In each of the above aspects, "deprotecting a tert-butoxycarbonyl group of the compound represented by Formula (A-7) to obtain the compound represented by Formula (B) or a salt thereof" may further comprise:
  desalting the salt of the compound represented by Formula (B), which is obtained by deprotecting a tert-butoxycarbonyl group of the compound represented by Formula (A-7), to obtain the compound represented by Formula (B); or converting the compound represented by Formula (B), which is obtained by deprotecting a tert-butoxycarbonyl group of the compound represented by Formula (A-7), to a salt thereof to obtain the salt of the compound represented by Formula (B).

[13] A thirteenth aspect is a method for producing a compound represented by Formula (B), the method comprising: asymmetrically reducing a keto group of a compound represented by Formula (SM8) to obtain a compound represented by Formula (A8); and reacting the compound represented by Formula (A8) with ammonia water in the presence of a catalyst to obtain the compound represented by Formula (B).

Formula (B)
[C55]

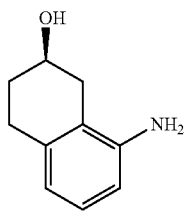

(B)

Formula (SM8)
[C56]

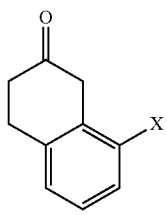

(SM8)

[in Formula (SM8), X is a halogen atom.]

Formula (A8)
[C57]

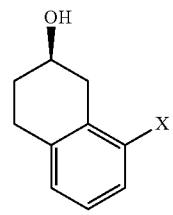

(A8)

[13-1] In the above aspect [13], each X in the compound represented by Formula (SM8) and the compound represented by Formula (A8) is preferably a fluorine atom, a chlorine atom, or a bromine atom, and is more preferably a bromine atom.

[13-2] In the above aspect [13], the catalyst is preferably a Pd catalyst or a Cu catalyst, is more preferably a Cu catalyst, and is even more preferably $Cu_2O$.

[13-3] A 13-3-th aspect is a method for producing a salt of the compound represented by Formula (B) in the above aspect [13], the method comprising: adding an inorganic acid or an organic acid to the compound represented by Formula (B) to obtain the salt of the compound represented by Formula (B). The inorganic acid or organic acid used for obtaining the salt of the compound represented by Formula (B) is preferably an inorganic acid, is more preferably hydrochloric acid or hydrobromic acid, and is even more preferably hydrobromic acid.

In the present specification, unless otherwise specified, "halogen atom" refers to, for example, a fluorine atom, a chlorine atom, a bromine atom, an iodine atom, and the like.

[14] A fourteenth aspect is a method for producing a compound represented by Formula (B), the method comprising: reacting a compound represented by Formula (A8) with ammonia water in the presence of a catalyst to obtain the compound represented by Formula (B).

Formula (B)
[C58]

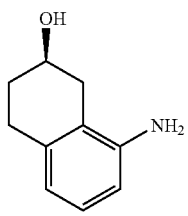

(B)

Formula (A8)
[C59]

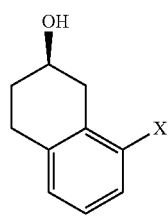

(A8)

[in Formula (A8), X is a halogen atom.]

[14-1] In the above aspect [14], X in the compound represented by Formula (A8) is preferably a fluorine atom, a chlorine atom, or a bromine atom, and is more preferably a bromine atom.

[14-2] In the above aspect [14], the catalyst is preferably a Pd catalyst or a Cu catalyst, is more preferably a Cu catalyst, and is even more preferably $Cu_2O$.

[14-3] A 14-3-th aspect is a method for producing a salt of the compound represented by Formula (B) in the above aspect [14], the method comprising: adding an inorganic acid or an organic acid to the compound represented by Formula (B) to obtain the salt of the compound represented by Formula (B). The inorganic acid or organic acid used for obtaining the salt of the compound represented by Formula (B) is preferably an inorganic acid, is more preferably hydrochloric acid or hydrobromic acid, and is even more preferably hydrobromic acid.

[15] A fifteenth aspect is a method for producing a compound represented by Formula (A8), the method comprising: asymmetrically reducing a keto group of a compound represented by Formula (SM8) to obtain the compound represented by Formula (A8).

Formula (A8)
[C60]

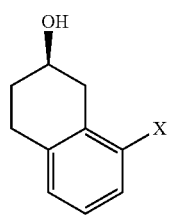
(A8)

[in Formula (A8), X is a halogen atom.]

Formula (SM8)
[C61]

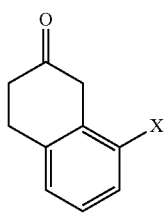
(SM8)

[in Formula (SM8), X is a halogen atom.]

[15-1] In the above aspect [15], each X in the compound represented by Formula (SM8) and the compound represented by Formula (A8) is preferably a fluorine atom, a chlorine atom, or a bromine atom, and is more preferably a bromine atom.

[16] A sixteenth aspect is a compound represented by Formula (A8).

[C62]

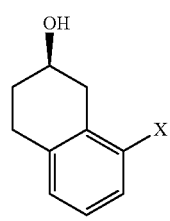
(A8)

[in Formula (A8), X is a halogen atom.]

[16-1] In the above aspect [16], X in the compound represented by Formula (A8) is preferably a fluorine atom, a chlorine atom, or a bromine atom, and is more preferably a bromine atom.

[17] A seventeenth aspect is a method for producing a compound represented by Formula (I), the method comprising: asymmetrically reducing a keto group of a compound represented by Formula (SM8) to obtain a compound represented by Formula (A8); reacting the compound represented by Formula (A8) with ammonia water in the presence of a catalyst to obtain a compound represented by Formula (B); and causing a condensation reaction of the compound represented by Formula (B) and a compound represented by Formula (CA-1) using DMT-MM as a condensation agent to obtain the compound represented by Formula (I).

Formula (I)
[C63]

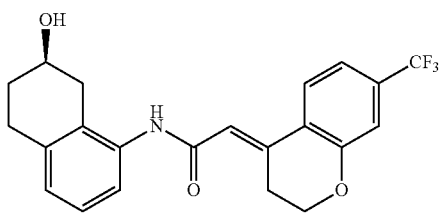
(I)

Formula (SM8)
[C64]

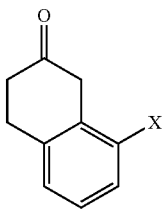
(SM8)

[in Formula (SM8), X is a halogen atom.]

Formula (A8)
[C65]

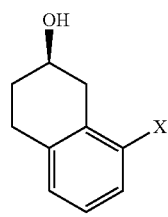
(A8)

[in Formula (A8), X is a halogen atom.]

Formula (B)
[C66]

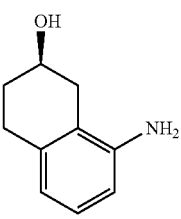
(A8)

Formula (CA-1)
[C67]

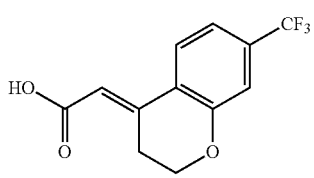
(CA-1)

[17-1] In the above aspect [17], each X in the compound represented by Formula (SM8) and the compound represented by Formula (A8) is preferably a fluorine atom, a chlorine atom, or a bromine atom, and is more preferably a bromine atom.

[17-2] In the above aspect [17], the catalyst is preferably a Pd catalyst or a Cu catalyst, is more preferably a Cu catalyst, and is even more preferably $Cu_2O$.

[18] An eighteenth aspect is a method for producing a compound represented by Formula (I), the method comprising: asymmetrically reducing a keto group of a compound represented by Formula (SM8) to obtain a compound represented by Formula (A8); reacting the compound represented by Formula (A8) with ammonia water in the presence of a catalyst to obtain a compound represented by Formula (B); adding an acid to the compound represented by Formula (B) to obtain a salt of the compound represented by Formula (B); and causing a condensation reaction of the salt of the compound represented by Formula (B) and a compound represented by Formula (CA-1) using DMT-MM as a condensation agent to obtain the compound represented by Formula (I).

Formula (I)
[C68]

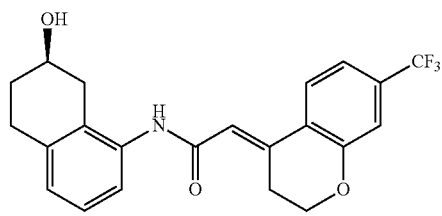
(I)

Formula (SM8)
[C69]

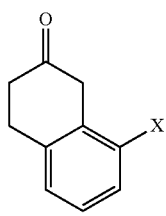
(SM8)

[in Formula (SM8), X is a halogen atom.]

Formula (A8)
[C70]

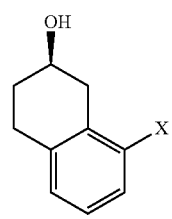
(A8)

[in Formula (A8), X is a halogen atom.]

Formula (B)
[C71]

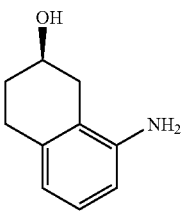
(B)

Formula (CA-1)
[C72]

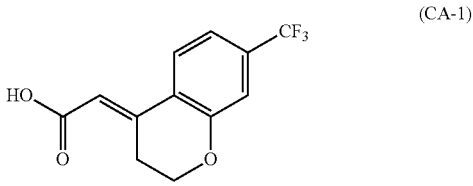
(CA-1)

[18-1] In the above aspect [18], each X in the compound represented by Formula (SM8) and the compound represented by Formula (A8) is preferably a fluorine atom, a chlorine atom, or a bromine atom, and is more preferably a bromine atom.

[18-2] In the above aspect [18], the catalyst is preferably a Pd catalyst or a Cu catalyst, is more preferably a Cu catalyst, and is even more preferably $Cu_2O$.

[18-3] In the above aspect [18], the acid used in obtaining a salt of the compound represented by Formula (B) is preferably an inorganic acid or an organic acid, is more preferably an inorganic acid, is even more preferably hydrochloric acid or hydrobromic acid, and is particularly preferably hydrobromic acid.

[19] A nineteenth aspect is a method for producing a compound represented by Formula (I), the method comprising: reacting a compound represented by Formula (A8) with ammonia water in the presence of a catalyst to obtain a compound represented by Formula (B); and causing a condensation reaction of the compound represented by Formula (B) and a compound represented by Formula (CA-1) using DMT-MM as a condensation agent to obtain the compound represented by Formula (I).

Formula (I)
[C73]

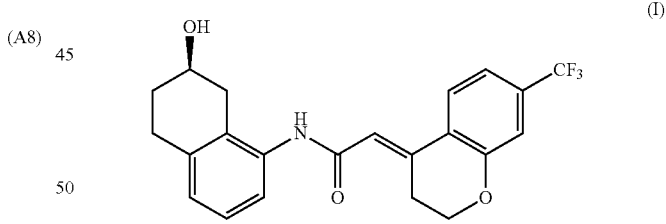
(I)

Formula (A8)
[C74]

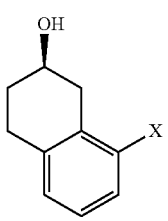
(A8)

[in Formula (A8), X is a halogen atom.]

Formula (B)
[C75]

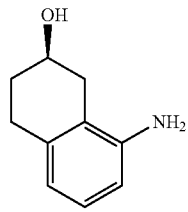
(B)

Formula (CA-1)
[C76]

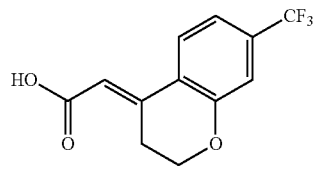
(CA-1)

[19-1] In the above aspect [19], each X in the compound represented by Formula (SM8) and the compound represented by Formula (A8) is preferably a fluorine atom, a chlorine atom, or a bromine atom, and is more preferably a bromine atom.

[19-2] In the above aspect [19], the catalyst is preferably a Pd catalyst or a Cu catalyst, is more preferably a Cu catalyst, and is even more preferably $Cu_2O$.

[20] A twentieth aspect is a method for producing a compound represented by Formula (I), the method comprising: reacting a compound represented by Formula (A8) with ammonia water in the presence of a catalyst to obtain a compound represented by Formula (B); adding an acid to the compound represented by Formula (B) to obtain a salt of the compound represented by Formula (B); and causing a condensation reaction of the salt of the compound represented by Formula (B) and a compound represented by Formula (CA-1) using DMT-MM as a condensation agent to obtain the compound represented by Formula (I).

Formula (I)
[C77]

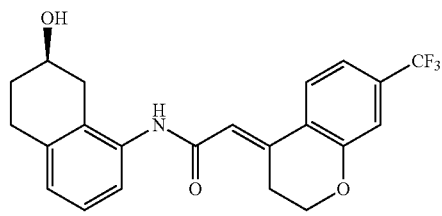
(I)

Formula (A8)
[C78]

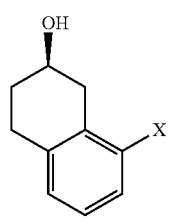
(A8)

[in Formula (A8), X is a halogen atom.]

Formula (B)
[C79]

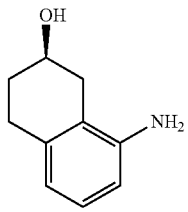
(B)

Formula (CA-1)
[C80]

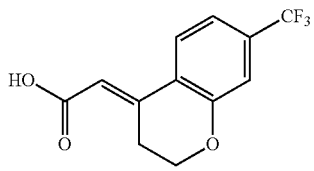
(CA-1)

[20-1] In the above aspect [20], each X in the compound represented by Formula (SM8) and the compound represented by Formula (A8) is preferably a fluorine atom, a chlorine atom, or a bromine atom, and is more preferably a bromine atom.

[20-2] In the above aspect [20], the catalyst is preferably a Pd catalyst or a Cu catalyst, is more preferably a Cu catalyst, and is even more preferably $Cu_2O$.

[20-3] In the above aspect [20], the acid used in obtaining a salt of the compound represented by Formula (B) is preferably an inorganic acid or an organic acid, is more preferably an inorganic acid, is even more preferably hydrochloric acid or hydrobromic acid, and is particularly preferably hydrobromic acid.

Hereinafter, each of the reactions in the above-described aspects will be described in detail.

<Step of Producing Compound Represented by Formula (A-5)>

The compound represented by Formula (A-5) is obtained by tert-butoxycarbonylating an amino group of the compound represented by Formula (A).

Examples of tert-butoxycarbonylating agents include di-tert-butyl dicarbonate ($Boc_2O$), 2-(tert-butoxycarbonyloxyimino)-2-phenylacetonitrile (Boc-ON), N-tert-butoxycarbonylimidazole, 2-(tert-butoxycarbonylthio)-4,6-dimethylpyrimidine, 1-tert-butoxycarbonyl-1,2,4-triazole, tert-butyl phenyl carbonate, tert-butyl carbazate, N-(tert-butoxycarbonyloxy)phthalimide, and the like. Di-tert-butyl dicarbonate ($Boc_2O$) and 2-(tert-butoxycarbonyloxyimino)-2-phenylacetonitrile (Boc-ON) are preferable, and di-tert-butyl dicarbonate ($Boc_2O$) is more preferable. A usage amount of a tert-butoxycarbonylating agent is generally 1.0 to 2.0 molar equivalents, is preferably 1.1 to 1.8 molar equivalents, and is more preferably 1.3 to 1.65 molar equivalents, with respect to 1 molar equivalent of the compound represented by Formula (A).

The reaction may be performed in the presence of a solvent. As the solvent, it is possible to use for example, a solvent not involved in the reaction such as dichloromethane, acetonitrile, diethyl ether, tetrahydrofuran, 1,2-dimethoxyethane, 1,4-dioxane, tert-butyl ether, toluene, water and the like, or a mixed solvent thereof. The solvent can be appropriately selected depending on the type of tert-butoxycarbonylating agent to be used. Tetrahydrofuran, 1,4-dioxane, a mixed solvent of tetrahydrofuran-water, and a mixed solvent of 1,4-dioxane-water are preferable, and tetrahydrofuran, a mixed solvent of tetrahydrofuran-water, and a mixed solvent of 1,4-dioxane-water are more preferable.

The reaction may be performed in the presence of a base. As the base, it is possible to use bases such as sodium hydrogen carbonate, potassium carbonate, sodium carbonate, triethylamine, N,N-diisopropylethylamine, pyridine and the like. The base can be appropriately selected depending on the type of tert-butoxycarbonylating agent to be used. Sodium hydrogen carbonate, triethylamine, and pyridine are preferable, and sodium hydrogen carbonate is more preferable.

A usage amount of the base is, for example, 1.0 to 4.0 molar equivalents, is preferably 1.0 to 3.5 molar equivalents, and is more preferably 1.0 to 3.2 molar equivalents, with respect to 1 molar equivalent of the compound represented by Formula (A).

Regarding a reaction temperature, the reaction can be performed within, for example, a range of −78° C. to a temperature at which the solvent is refluxed, a range of −78° C. to room temperature, a range of 0° C. to a temperature at which the solvent is refluxed, or a range of 0° C. to room temperature. The reaction temperature can be appropriately selected depending on the type of tert-butoxycarbonylating agent to be used. A reaction temperature is preferably within a range of 20° C. to 55° C.

<Step of Producing Compound Represented by Formula (A-6)>

The compound represented by Formula (A-6) is obtained by causing an oxidation reaction of the compound represented by Formula (A-5) or the compound represented by Formula (A-7).

Examples of oxidation reactions include Swern oxidation, PCC oxidation (chromate oxidation), Dess-Martin oxidation, TPAP oxidation, TEMPO oxidation, and the like. TEMPO oxidation is preferable.

The TEMPO oxidation is generally a reaction in which TEMPO and a reoxidant are combined as an oxidizing agent to oxidize a substrate such as alcohol. In addition, the TEMPO oxidation can also be performed in the presence of a base.

In the oxidation reaction, for example, a batch method, and flow chemistry (a reaction in flow mode using a continuous stirred tank reactor (CSTR)) are used.

A usage amount of the oxidant in the oxidation reaction is generally 1.0 to 2.2 molar equivalents, is preferably 1.2 to 2.1 molar equivalents, and is more preferably 1.4 to 2.0 molar equivalents, with respect to 1 molar equivalent of the compound represented by Formula (A-5) or the compound represented by Formula (A-7).

A usage amount of TEMPO in the TEMPO oxidation is generally 0.01 to 1.0 molar equivalents, is preferably 0.05 to 0.7 molar equivalents, and is more preferably 0.5 molar equivalents, with respect to 1 molar equivalent of the compound represented by Formula (A-5) or the compound represented by Formula (A-7).

Examples of reoxidants in the TEMPO oxidation include sodium hypochlorite (NaClO), iodobenzene diacetate, and the like. A usage amount of sodium hypochlorite in the TEMPO oxidation is generally 1.0 to 2.5 molar equivalents, is preferably 1.1 to 2.2 molar equivalents, and is more preferably 1.2 to 2.0 molar equivalents, with respect to 1 molar equivalent of the compound represented by Formula (A-5) or the compound represented by Formula (A-7).

The TEMPO oxidation can be performed in the presence of a base, and for example, a usage amount of $NaHCO_3$ as a base is generally 1.0 to 5.0 molar equivalents, is preferably 2.0 to 4.5 molar equivalents, and is more preferably 4.0 molar equivalents, with respect to 1 molar equivalent of the compound represented by Formula (A-5) or the compound represented by Formula (A-7).

A usage amount of KBr in the TEMPO oxidation is generally 0.01 to 0.30 molar equivalents, is preferably 0.02 to 0.25 molar equivalents, and is more preferably 0.05 to 0.2 molar equivalents, with respect to 1 molar equivalent of the compound represented by Formula (A-5) or the compound represented by Formula (A-7).

The oxidation reaction (for example, the TEMPO oxidation) may be performed in the presence of a solvent. As the solvent, it is possible to use, for example, a solvent not involved in the reaction such as dichloromethane, 1,2-dichloroethane, chloroform, acetonitrile, acetone, water and the like, or a mixed solvent thereof. The solvent can be appropriately selected depending on the type of oxidation reaction to be used. In the TEMPO oxidation, dichloromethane, acetonitrile, acetone, water, or a mixed solvent thereof is preferable; dichloromethane, acetonitrile, acetone, water, dichloromethane-water, acetonitrile-water, or acetone-water is more preferable; and dichloromethane, water, or dichloromethane-water is even more preferable.

Regarding an oxidation reaction (for example, a reaction temperature in the TEMPO oxidation), the reaction can be performed within, for example, a range of −78° C. to a temperature at which the solvent is refluxed, a range of −78° C. to room temperature, a range of 0° C. to a temperature at which the solvent is refluxed, or a range of 0° C. to room temperature. The reaction temperature can be appropriately selected depending on the type of oxidation reaction to be used. In the TEMPO oxidation, a reaction temperature is preferably within a range of −2° C. to 5° C.

It is also possible to use a reducing agent such as $Na_2S_2O_4$ (aqueous solution) to remove TEMPO after the TEMPO oxidation reaction.

<Step of Producing Compound Represented by Formula (A-7)>

The compound represented by Formula (A-7) is obtained by asymmetrically reducing the ketone compound represented by Formula (A-6).

Examples of asymmetric reductions include asymmetric reduction using a chemical catalyst or the like, asymmetric reduction using a biocatalyst (yeast, fungus, mold, enzyme, and the like), and the like. Asymmetric reduction using an enzyme is preferable, asymmetric reduction using a ketone reductase (ketoreductase: KRED) as an enzyme is more preferable, and asymmetric reduction using a ketone reductase derived from *Lactobacillus* sp. as an enzyme is particularly preferable. The asymmetric reduction using a ketone reductase is performed using a ketone reductase, a coenzyme, and a coenzyme regeneration system. Typical examples of coenzymes for ketone reductases include NADP. Furthermore, as a typical example of a coenzyme regeneration system that regenerates NADP, which is a coenzyme, oxidation of glucose by glucose dehydrogenase (GDH) is known. Furthermore, the asymmetric reduction using a ketone reductase is preferably performed in a solvent in the presence of a buffer solution.

A usage amount of the reducing agent in the asymmetric reduction, for example, in the asymmetric reduction using a chemical catalyst or the like, is generally 1.0 to 2.2 molar equivalents, and is preferably 1.2 to 2.0 molar equivalents, with respect to 1 molar equivalent of the compound represented by Formula (A-6).

In the asymmetric reduction using an enzyme, a usage amount of the enzyme is generally 1.0 to 25 times, is preferably 5 to 20 times, and is more preferably 10 times an amount of 1 g of the compound represented by Formula (A-6).

In the asymmetric reduction using a ketone reductase derived from *Lactobacillus* sp., a usage amount of the enzyme is generally 1.0 to 25 times, is preferably 5 to 20 times, and is more preferably 10 times an amount of 1 g of the compound represented by Formula (A-6).

D-glucose may be used in the asymmetric reduction using an enzyme. When D-glucose is used, a usage amount of D-glucose is generally 1.0 to 5.0 times, is preferably 1.5 to 3.5 times, and is more preferably 2.0 times an amount of 1 g of the compound represented by Formula (A-6).

In the asymmetric reduction using an enzyme, glucose dehydrogenase (GDH) may be used. When glucose dehydrogenase (GDH) is used, a usage amount of glucose dehydrogenase (GDH) is generally 0.01 to 0.5 times, is preferably 0.05 to 0.2 times, and is more preferably 0.05 times or 0.2 times an amount of 1 g of the compound represented by Formula (A-6).

In the asymmetric reduction using an enzyme, a coenzyme may be used, and for example, nicotinamide adenine dinucleotide phosphate (NADP) may be used. When nicotinamide adenine dinucleotide phosphate (NADP) is used, a usage amount nicotinamide adenine dinucleotide phosphate (NADP) is generally 0.01 to 0.5 times, is preferably 0.025 to 0.1 times, and is more preferably 0.025 times or 0.1 times an amount of 1 g of the compound represented by Formula (A-6).

The asymmetric reduction may be performed in the presence of a solvent. As the solvent, it is possible to use, for example, a solvent not involved in the reaction such as alcohol-based solvents such as methanol, ethanol, propanol, butanol and the like; hydrocarbon-based solvents such as heptane, hexane, octane, toluene and the like; ether-based solvents such as tetrahydrofuran, 1,4-dioxane, butyl ether and the like; polar solvents such as acetonitrile, dimethyl sulfoxide, dimethylformamide and the like; and water, or a mixed solvent thereof. The solvent can be appropriately selected depending on the type of enzyme to be used.

In the asymmetric reduction using an enzyme, as the buffer solution, it is possible to use, for example, buffer solutions such as a phosphate buffer solution, a potassium phosphate buffer solution (which can be prepared from, for example, reagents such as $K_2HIPO_4 \cdot 3H_2O$, $KH_2PO_4$ and the like), a Tris/HCl buffer solution, a sodium tetraborate-hydrochloric acid buffer solution, a triethanolamine buffer solution and the like. The buffer solution can be appropriately selected depending on the type of enzyme to be used.

In the asymmetric reduction using a ketone reductase derived from *Lactobacillus* sp., the solvent is preferably dimethyl sulfoxide, toluene, water, or a mixed solvent thereof, and is more preferably toluene, water, or a mixed solvent of toluene-water.

In the asymmetric reduction using an enzyme, a usage amount of the organic solvent is generally 1.0 to 15 times, is preferably 2 to 13 times, and is more preferably 5.0 times an amount of 1 g of the compound represented by Formula (A-6).

In the asymmetric reduction using an enzyme, a usage amount of the buffer solution is generally 10 to 40 times, is preferably 15 to 30 times, and is more preferably 30 times an amount of 1 g of the compound represented by Formula (A-6).

In the asymmetric reduction using an enzyme, a pH of a reaction solution is generally 6.0 to 7.5, is preferably 6.0 to 6.5, 6.5 to 7.0, or 6.0 to 7.0, and is more preferably 6.0 to 7.0.

A reaction temperature when performing the asymmetric reduction can be appropriately selected from a reaction temperature within, for example, a range of −78° C. to a temperature at which the solvent is refluxed, a range of −78° C. to room temperature, a range of 0° C. to a temperature at which the solvent is refluxed, a range of 0° C. to room temperature, and the like. A reaction temperature is preferably within a range of 0° C. to room temperature.

A reaction temperature when performing the asymmetric reduction using an enzyme is generally within a range of temperatures at which the enzyme is not deactivated, and it is preferably within a range of 20° C. to 60° C., is more preferably within a range of 20° C. to 25° C. or a range of 50° C. to 60° C., and is even more preferably within a range of 20° C. to 25° C.

<Step of Producing Compound Represented by Formula (B) or Salt Thereof from Formula (A-7)>

The compound represented by Formula (B) or a salt thereof is obtained by deprotecting a tert-butoxycarbonyl group of the chiral alcohol compound represented by Formula (A-7), by desalting the salt of the compound represented by Formula (B) obtained by deprotecting the tert-butoxycarbonyl group, or by converting the compound represented by Formula (B) obtained by deprotecting the tert-butoxycarbonyl group to its salt.

Examples of reagents used for deprotecting the tert-butoxycarbonyl group generally include acidic reagents, and the reagent is preferably hydrogen chloride (which is hydrochloric acid, or which is generated in a solvent system using acetyl chloride and an alcohol solvent such as methanol, ethanol, propanol, and the like), hydrogen bromide, and trifluoroacetic acid; is more preferably hydrogen chloride (which is hydrochloric acid, or which is generated in a solvent system using acetyl chloride and an alcohol solvent such as methanol, ethanol, propanol, and the like) and trifluoroacetic acid; and is particularly preferably hydrogen chloride (which is hydrochloric acid, or which is generated in a solvent system using acetyl chloride and an alcohol solvent such as methanol, ethanol, propanol, and the like).

Deprotection of the tert-butoxycarbonyl group may be performed in the presence of a solvent. Examples of solvents for deprotecting the tert-butoxycarbonyl group include solvents not involved in the reaction such as halogen-based solvents such as dichloromethane, chloroform, 1,2-dichloroethane and the like; alcohol-based solvents such as methanol, ethanol, propanol, butanol and the like; hydrocarbon-based solvents such as heptane, hexane, octane, toluene and the like; ether-based solvents such as tetrahydrofuran, 1,4-dioxane, butyl ether and the like; polar solvents such as acetone, acetonitrile, dimethyl sulfoxide, dimethylformamide and the like; and water, or a mixed solvent thereof, and halogen-based solvents such as dichloromethane, chloroform, 1,2-dichloroethane and the like, and alcohol-based solvents such as methanol, ethanol, propanol, butanol and the like are preferable, and propanol (n-propanol) is more preferable.

A reaction temperature when deprotecting the tert-butoxycarbonyl group can be appropriately selected from a reaction temperature within, for example, a range of −78° C. to a temperature at which the solvent is refluxed, a range of −78° C. to room temperature, a range of 0° C. to a temperature at which the solvent is refluxed, a range of 0° C. to room temperature, and the like. A reaction temperature is preferably within a range of 0° C. to 55° C.

It is possible to desalt the salt of the compound represented by Formula (B) by using a base. As the base for desalting the salt of the compound represented by Formula (B), it is possible to use bases such as sodium hydrogen carbonate, potassium carbonate, sodium carbonate, triethylamine, N,N-diisopropylethylamine, pyridine and the like, and sodium hydrogen carbonate, potassium carbonate, and sodium carbonate are preferable, and sodium hydrogen carbonate is more preferable.

Desalting of the salt of the compound represented by Formula (B) can be performed in the presence of a solvent. Examples of solvents for desalting the salt of the compound represented by Formula (B) include solvents not involved in the reaction such as halogen-based solvents such as dichloromethane, chloroform, 1,2-dichloroethane and the like; ether-based solvents such as tetrahydrofuran, 1,4-dioxane, butyl ether and the like; polar solvents such as ethyl acetate, isopropyl acetate, acetonitrile, dimethyl sulfoxide, dimethylformamide and the like; and water, or a mixed solvent thereof, and ethyl acetate, isopropyl acetate, water, and a mixed solvent of ethyl acetate-water or isopropyl acetate-water are preferable, and a mixed solvent of ethyl acetate-water is more preferable.

<Step of Producing the Salt from Compound Represented by Formula (B)>

The compound represented by Formula (B) can be converted to a salt using an organic acid or an inorganic acid. As an acid for converting the compound represented by Formula (B) to a salt thereof, it is possible to use, for example, acids such as hydrochloric acid, hydrobromic acid, hydriodic acid, nitric acid, sulfuric acid, phosphoric acid, formic acid, acetic acid, trifluoroacetic acid, propionic acid, butyric acid, valeric acid, enanthic acid, capric acid, myristic acid, palmitic acid, stearic acid, lactic acid, sorbic acid, mandelic acid, oxalic acid, malonic acid, succinic acid, fumaric acid, maleic acid, malic acid, tartaric acid, citric acid, benzoic acid, salicylic acid, phthalic acid, cinnamic acid, glycolic acid, pyruvic acid, oxylic acid, salicylic acid, N-acetylcysteine, methanesulfonic acid, benzenesulfonic acid, p-toluenesulfonic acid, aspartic acid, glutamic acid and the like, and hydrochloric acid, hydrobromic acid, nitric acid, sulfuric acid, phosphoric acid, acetic acid, phthalic acid, fumaric acid, oxalic acid, tartaric acid, maleic acid, citric acid, succinic acid, methanesulfonic acid, and p-toluenesulfonic acid are preferable, hydrochloric acid and hydrobromic acid are more preferable, and hydrobromic acid is even more preferable.

The conversion of the compound represented by Formula (B) into a salt thereof can be performed in the presence of a solvent. Examples of solvent for converting the compound represented by Formula (B) to a salt thereof include solvents not involved in the reaction such as halogen-based solvents such as dichloromethane, chloroform, 1,2-dichloroethane and the like; ether-based solvents such as tetrahydrofuran, 1,4-dioxane, butyl ether and the like; alcohol-based solvents such as methanol, ethanol and the like; polar solvents such as ethyl acetate, isopropyl acetate, acetonitrile, dimethyl sulfoxide, dimethylformamide and the like; and water, or a mixed solvent thereof, and a solvent not involved in the reaction such as dichloromethane, chloroform, 1,2-dichloroethane, tetrahydrofuran, 1,4-dioxane, methanol, ethanol, ethyl acetate, and water, or a mixed solvent thereof is preferable, and ethyl acetate, water, or ethyl acetate-water is more preferable.

<Step of Producing Compound Represented by Formula (A8)>

The compound represented by Formula (A8) is obtained by asymmetrically reducing the ketone compound represented by Formula (SM8).

Examples of asymmetric reductions include asymmetric reduction using a chemical catalyst or the like, asymmetric reduction using a biocatalyst (yeast, fungus, mold, enzyme, and the like), and the like. Asymmetric reduction using an enzyme is preferable, asymmetric reduction using a ketone reductase (KRED: ketoreductase) as an enzyme is more preferable, and asymmetric reduction using a ketone reductase derived from *Escherichia coli* sp. as an enzyme is particularly preferable. The asymmetric reduction using a ketone reductase is performed using a ketone reductase, a coenzyme, and a coenzyme regeneration system. Typical examples of coenzymes for ketone reductases include NADP. Furthermore, as a typical example of a coenzyme regeneration system that regenerates NADP, which is a coenzyme, oxidation of glucose by glucose dehydrogenase (GDH) is known. Furthermore, the asymmetric reduction using a ketone reductase is preferably performed in a solvent in the presence of a buffer solution.

A usage amount of the reducing agent in the asymmetric reduction, for example, in the asymmetric reduction using a chemical catalyst or the like, is generally 1.0 to 2.2 molar equivalents, and is preferably 1.2 to 2.0 molar equivalents, with respect to 1 molar equivalent of the compound represented by Formula (SM8).

In the asymmetric reduction using an enzyme, a usage amount of the enzyme is generally 0.01 to 0.1 times, is preferably 0.02 to 0.07 times, and is more preferably 0.047 to 0.05 times an amount of 1 g of the compound represented by Formula (SM8).

In the asymmetric reduction using a ketone reductase (KRED) derived from *Escherichia coli* sp., a usage amount of the enzyme is 0.01 to 0.1 times, is preferably 0.02 to 0.07 times, and is more preferably 0.047 to 0.05 times an amount of 1 g of the compound represented by Formula (SM8).

D-glucose may be used in the asymmetric reduction using an enzyme. When D-glucose is used, a usage amount of D-glucose is generally 1.0 to 5.0 times, is preferably 1.5 to 3.5 times, and is more preferably 1.9 to 2.0 times an amount of 1 g of the compound represented by Formula (SM8).

In the asymmetric reduction using an enzyme, glucose dehydrogenase (GDH) may be used. When glucose dehydrogenase (GDH) is used, a usage amount of glucose dehydrogenase (GDH) is generally 0.01 to 0.1 times, is preferably 0.01 to 0.05 times, and is more preferably 0.019 to 0.02 times an amount of 1 g of the compound represented by Formula (SM8).

In the asymmetric reduction using an enzyme, nicotinamide adenine dinucleotide phosphate (NADP) may be used. When nicotinamide adenine dinucleotide phosphate (NADP) is used, a usage amount nicotinamide adenine dinucleotide phosphate (NADP) is generally 0.001 to 0.1 times, is preferably 0.005 to 0.05 times, and is more preferably 0.009 to 0.01 times an amount of 1 g of the compound represented by Formula (SM8).

The asymmetric reduction may be performed in the presence of a solvent. As the solvent, it is possible to use, for example, a solvent not involved in the reaction such as alcohol-based solvents such as methanol, ethanol, propanol, butanol and the like; hydrocarbon-based solvents such as heptane, hexane, octane, toluene and the like; ether-based solvents such as tetrahydrofuran, 1,4-dioxane, butyl ether and the like; polar solvents such as acetone, acetonitrile, dimethyl sulfoxide, dimethylformamide and the like; and water, or a mixed solvent thereof, and the solvent can be appropriately selected depending on the type of enzyme to be used.

In the asymmetric reduction using an enzyme, as the buffer solution, it is possible to use, for example, buffer solutions such as a phosphate buffer solution, a potassium phosphate buffer solution (which can be prepared from, for example, reagents such as $K_2HPO_4$ $3H_2O$ and $KH_2PO_4$), a Tris/HCl buffer solution, a sodium tetraborate-hydrochloric acid buffer solution, a triethanolamine buffer solution and the like, and the buffer solution can be appropriately selected depending on the type of enzyme to be used.

In the asymmetric reduction using a ketone reductase (KRED) derived from *Escherichia coli* sp., the solvent is preferably dimethyl sulfoxide, water, or a mixed solvent of dimethyl sulfoxide-water.

In the asymmetric reduction using a ketone reductase (KRED) derived from *Escherichia coli* sp., a usage amount of the organic solvent is generally 1.0 to 10 times, is preferably 2 to 5 times, and is more preferably 2.5 to 3.0 times an amount of 1 g of the compound represented by Formula (SM8).

In the asymmetric reduction using a ketone reductase (KRED) derived from *Escherichia coli* sp., a usage amount of the buffer solution is generally 10 to 40 times, is preferably 15 to 30 times, and is more preferably 28 to 30 times an amount of 1 g of the compound represented by Formula (SM8).

In the asymmetric reduction using an enzyme, a pH of a reaction solution is generally 6.0 to 7.5, and is preferably 6.5 to 7.0.

A reaction temperature when performing the asymmetric reduction can be appropriately selected from a reaction temperature within, for example, a range of −78° C. to a temperature at which the solvent is refluxed, a range of −78° C. to room temperature, a range of 0° C. to a temperature at which the solvent is refluxed, a range of 0° C. to room temperature, and the like. A reaction temperature is preferably within a range of 0° C. to room temperature.

A reaction temperature when performing the asymmetric reduction using an enzyme is generally within a range of temperatures at which the enzyme is not deactivated, and it is preferably within a range of 20° C. to 60° C., is more preferably within a range of 20° C. to 35° C., and is even more preferably within a range of 20° C. to 30° C.

Unless otherwise specified in the present specification, when Formula (SM8) is referred to, it includes low-order formulas thereof (for example, Formula (SM8-FL), Formula (SM8-CL), Formula (SM8-BR), Formula (SM8-ID), and the like). Similarly, unless otherwise specified in the present specification, when Formula (A8) is referred to, it includes low-order formulas thereof (for example, Formula (A8-FL), Formula (A8-CL), Formula (A8-BR), Formula (A8-ID), and the like).

Furthermore, Formula (SM8-FL) is a compound in which X=fluorine atom in the compound represented by Formula (SM8). Formula (SM8-CL) is a compound in which X=chlorine atom in the compound represented by Formula (SM8). Formula (SM8-BR) is a compound in which X=bromine atom in the compound represented by Formula (SM8). Formula (SM8-ID) is a compound in which X=iodine atom in the compound represented by Formula (SM8).

Furthermore, Formula (A8-FL) is a compound in which X=fluorine atom in the compound represented by Formula (A8). Formula (A8-CL) is a compound in which X=chlorine atom in the compound represented by Formula (A8). Formula (A8-BR) is a compound in which X=bromine atom in the compound represented by Formula (A8). Formula (A8-ID) is a compound in which X=iodine atom in the compound represented by Formula (A8).

<Step of Producing Compound Represented by Formula (B) from Formula (A8)>

The compound represented by Formula (B) is obtained by causing an amination reaction of the compound represented by Formula (A8) in the presence of a metal catalyst using ammonia (ammonia water (for example, 25%, 28%, 30%, and the like)). A concentration (%) of ammonia water is w/w % or w/v %.

Examples of catalysts for the amination reaction of the compound represented by Formula (A8) using ammonia for a nitrogen source include a Pd catalyst, a Cu catalyst, and the like. Examples of Pd catalysts include a $Pd_2(dba)_3$ $PdCl_2$-Josiphos complex and the like, and examples of Cu catalysts include CuI, $Cu(OAc)_2$, $Cu_2O$, CuO, CuBr, CuCl, $CuSO_4$, $CuFe_2O_4$, and the like, and a Cu catalyst is preferable, and $Cu_2O$ is more preferable.

Examples of solvents for the amination reaction include solvents such as dimethyl sulfoxide, N,N-dimethylformamide, N-methylpyrrolidone (NMP), 1,4-dioxane, acetonitrile, toluene, a mixed solvent thereof and the like, where N-methylpyrrolidone (NMP) is preferable.

A base may be present in the amination reaction, and examples of bases include bases such as potassium carbonate, potassium phosphate, cesium carbonate, N,N-diisopropylethylamine, triethylamine and the like.

The amination reaction is performed by sealed tube heating using a sealed tube reactor (made of, for example, stainless steel, glass, or the like). When a heating reaction is performed, heating above a boiling point of a solvent or reagent used is generally not performed, and heating is performed in a closed system using a sealed tube reactor or the like when the reaction is performed at a temperature higher than a boiling point of a solvent or reagent used.

Examples of solvents that can be used when performing the amination reaction and their boiling points are as follows: dimethyl sulfoxide (boiling point 189° C.), N,N-dimethylformamide (boiling point 153° C.), N-methylpyrrolidone (NMP) (boiling point 202° C.), 1,4-dioxane (boiling point 101° C.), acetonitrile (boiling point 82° C.), and toluene (boiling point 110.6° C.). Furthermore, a boiling point of ammonia water is 37.7° C. for 25% ammonia water and 24.7° C. for 32% ammonia water.

A reaction temperature when performing the amination reaction can be appropriately selected from, for example, a reaction temperature within a range of 100° C. to 250° C., a range of 100° C. to 200° C., a range of 100° C. to 150° C., and the like. A reaction temperature is preferably within a range of 100° C. to 120° C.

In the amination reaction, when $Cu_2O$ is used, a usage amount of the metal catalyst is generally 0.1 to 1.0 molar equivalents, is preferably 0.2 to 0.8 molar equivalents, and is more preferably 0.5 to 0.7 molar equivalents, with respect to 1 molar equivalent of the compound represented by Formula (A8).

In the amination reaction, a usage amount of the organic solvent is generally 0.1 to 30 times, and is preferably 0.5 to 20 times an amount of 1 g of the compound represented by Formula (A8).

In the amination reaction, a usage amount of the ammonia water is generally 1.0 to 50 times, is preferably 2.5 to 30 times, and is more preferably 2.5 to 3.5 times an amount of 1 g of the compound represented by Formula (A8).

Unless otherwise specified, a numerical value range described in the present specification also includes ±10% values of that values. For example, when the phrase "0.1 to 1.0 molar equivalents" is referred to, it means 0.1±0.01 to 1.0±0.1 molar equivalents, and when the phrase "0.1 to 30 times an amount . . . " is referred to, it means 0.1±0.01 to 30±3 times.

<Step of Producing Compound Represented by Formula (I)>

The compound represented by Formula (I) is obtained by a condensation reaction of the compound represented by Formula (B) or a salt thereof and the compound represented by Formula (CA-1) while using DMT-MM as a condensation agent.

The condensation reaction may be performed in the presence of a solvent. Examples of solvents include solvents not involved in the reaction such as alcohol-based solvents such as methanol, ethanol, propanol, isopropanol, butanol and the like; ether-based solvents such as tetrahydrofuran, 1,4-dioxane, butyl ether and the like; and water, or a mixed solvent thereof, and alcohol-based solvents, water, or a mixed solvent thereof is preferable; methanol, ethanol, isopropanol, water, or a mixed solvent thereof is more preferable; methanol, ethanol, or isopropanol is even more preferable; and methanol or isopropanol is particularly preferable.

In the condensation reaction, a usage amount of the carboxylic acid compound represented by Formula (CA-1) is generally 0.5 to 2.0 molar equivalents, is preferably 0.5 to 1.5 molar equivalents, and is more preferably 0.7 to 1.25 molar equivalents, with respect to 1 molar equivalent of the compound represented by Formula (B) or a salt thereof. As will be described later, the inventors of the present invention have found that use of DMT-MM for a condensation agent enables a selective condensation reaction of a carboxyl group of the compound represented by Formula (CA-1) and an amino group of the compound represented by Formula (B), and that, therefore, it is not required to protect hydroxyl groups of the compound represented by Formula (B) in the condensation reaction.

In the condensation reaction, a salt of the compound represented by Formula (B) is preferably an HCl salt or an HBr salt.

In the condensation reaction, a usage amount of DMT-MM as a condensation agent is generally 1.0 to 2.0 molar equivalents, is preferably 1.1 to 1.8 molar equivalents, and is more preferably 1.2 to 1.5 molar equivalents, with respect to 1 molar equivalent of the compound represented by Formula (B) or a salt thereof.

When a salt of the compound represented by Formula (B) is used in the condensation reaction, a base may be added. Examples of bases include organic bases such as triethylamine, N,N-diisopropylethylamine, pyridine and the like; and inorganic bases such as lithium hydroxide (lithium hydroxide monohydrate), sodium hydroxide, potassium hydroxide, lithium carbonate, sodium carbonate, potassium carbonate and the like. Triethylamine, N,N-diisopropylethylamine, pyridine, sodium carbonate, or potassium carbonate is preferable, and triethylamine is more preferable.

An amount of base that can be added when the salt of the compound represented by Formula (B) is used in the condensation reaction is generally 1.0 to 2.5 molar equivalents, is preferably 1.05 to 2.3 molar equivalents, and is more preferably 1.05 to 2.1 molar equivalents, with respect to 1 molar equivalent of a salt of the compound represented by Formula (B).

In the condensation reaction, a usage amount of the solvent is generally 5.0 to 100 times, is preferably 5 to 40 times, and is more preferably 5 to 30 times an amount of 1 g of the compound represented by Formula (B) or a salt thereof.

A reaction temperature when performing the condensation reaction can be appropriately selected from a reaction temperature within, for example, a range of −78° C. to a temperature at which the solvent is refluxed, a range of −78° C. to room temperature, a range of 0° C. to a temperature at which the solvent is refluxed, a range of 0° C. to room temperature, and the like. A reaction temperature is preferably within a range of 0° C. to room temperature.

8-amino-1,2,3,4-tetrahydronaphthalen-2-ol [CAS No. 624729-66-4] represented by Formula (A) in the above-described aspect [1] can be produced by selectively reducing a naphthalene ring using 8-aminonaphthalen-2-ol (Formula (SM-1)) as a starting material according to a production method known from a literature, for example, a production method below which is disclosed in WO 2009/050289 (Patent Literature 6).

(Scheme 4-1)

[C81]

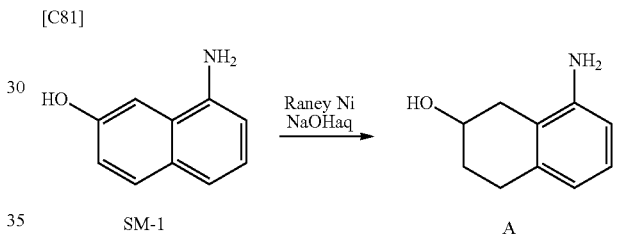

SM-1    A (E)-2-(7-(trifluoromethyl)chroman-4-ylidene)acetic acid [CAS No. 920334-15-2] represented by Formula (CA-1) in the above-described aspects [7] to [11] and the above-described aspects [17] to [20] can be produced by performing several steps using 3-hydroxybenzotrifluoride (Formula (CA-SM)) as a starting material according to a production method known from a literature, for example, a production method below which is disclosed in WO 2007/010383 (Patent Literature 1).

(Scheme 4-2)

[C82]

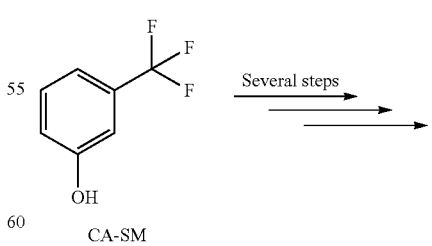

CA-SM

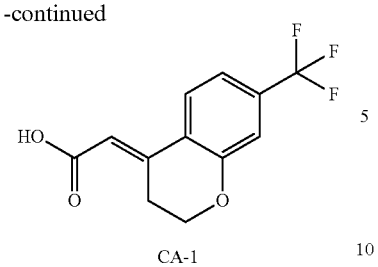

CA-1

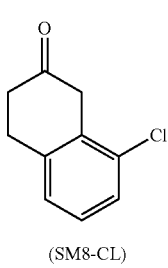

(SM8-CL)

For the compound represented by Formula (SM8) in the above-described aspects [13], [15], [17], and [18], a commercially available compound can be used. Alternatively, it can be obtained according to a production method known from a literature using a commercially available compound.

In the compound represented by Formula (SM8), the compound in which X=fluorine atom (Formula (SM8-FL)) can be produced according to, for example, a production method of (Scheme 4-3) below which is disclosed in European Patent Application Publication No. 343830.

In the compound represented by Formula (SM8), the compound in which X=bromine atom (Formula (SM8-BR)) can be produced according to, for example, a production method of (Scheme 4-5) below which is disclosed in Journal of Medicinal Chemistry, 36(17), p 2485-93, 1993 and European Journal of Medicinal Chemistry (1993), 28(9), p 693-701.

(Scheme 4-3)

[C83]

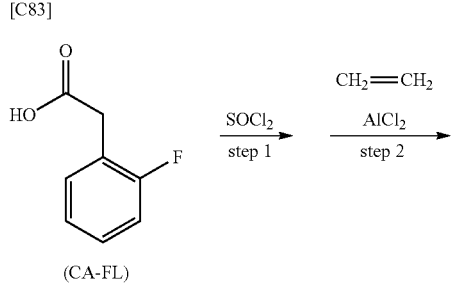

(CA-FL)

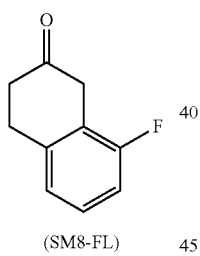

(SM8-FL)

In the compound represented by Formula (SM8), the compound in which X=chlorine atom (Formula (SM8-CL)) can be produced according to, for example, a production method of (Scheme 4-4) below which is disclosed in European Patent Application Publication No. 343830.

(Scheme 4-5)

[C85]

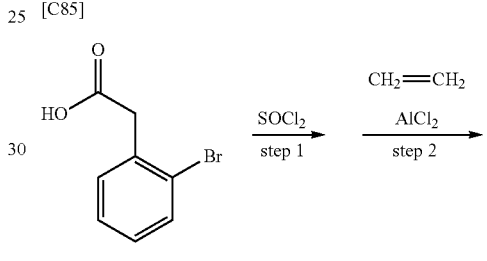

(CA-BR)

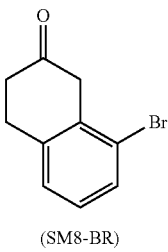

(SM8-BR)

In Formula (SM8), the compound in which X=iodine atom (Formula (SM8-ID)) can be produced according to the production methods for Formula (SM8-FL), Formula (SM8-CL), and Formula (SM8-BR) (Scheme 4-6).

(Scheme 4-4)

[C84]

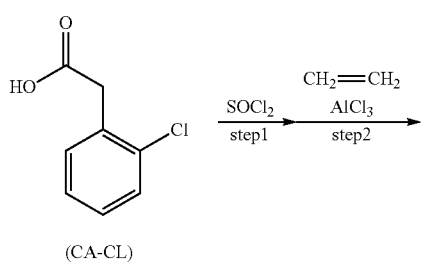

(CA-CL)

(Scheme 4-6)

[C86]

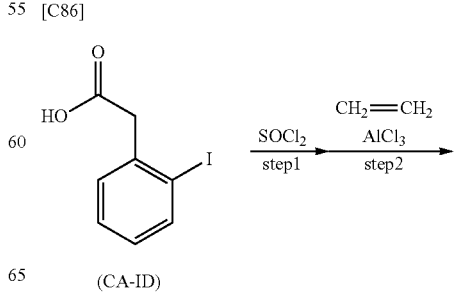

(CA-ID)

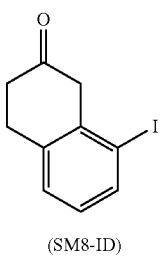

(SM8-ID)

A raw material compound of each of the steps in the production method can be used in the next step as a reaction solution itself or as a crude product. Furthermore, the raw material compound can also be isolated from a reaction mixture according to a conventional method, and it can be easily purified by a known method, for example, a separation methods such as extraction, concentration, neutralization, filtration, distillation, recrystallization, chromatography and the like.

When a mixed solvent is used in the above-described reactions, it can be used by mixing two or more kinds of solvents in an appropriate ratio, for example, in a ratio of 1:1 to 1:10 as a volume ratio or a weight ratio.

Unless otherwise specified, a reaction time for each of the steps in the production method is not limited as long as it is a time that enables the reaction to proceed sufficiently. For example, a reaction time may be any of 0.1 hours, 0.5 hours, 1 hour, 1.5 hours, 2 hours, 3 hours, 4 hours, 5 hours, 10 hours, 12 hours, 18 hours, 24 hours, 36 hours, 48 hours, 60 hours, 72 hours, or 115 hours, and it may be a time within a range of the lower limit value and the upper limit value of these times.

Regarding the reaction temperature, a temperature when the phrase "range of −78° C. to a temperature at which the solvent is refluxed" is referred to means a temperature within a range of −78° C. to a temperature at which the solvent (or a mixed solvent) used for the reaction is refluxed. For example, when methanol is used as the solvent, the phrase "−78° C. to a temperature at which the solvent is refluxed" means a temperature within a range of −78° C. to a temperature at which methanol is refluxed.

The same applies to when the phrase "0° C. to a temperature at which the solvent is refluxed" is referred to, and it means a temperature within a range of 0° C. to a temperature at which the solvent (or a mixed solvent) used for the reaction is refluxed. A lower limit value of the temperature is, for example, −78° C. or 0° C. as described above, but it also may be other temperatures such as 20° C., 23° C., 25° C., 40° C., 50° C., 70° C., 80° C., 90° C., 100° C., 150° C. and the like.

Regarding the reaction temperature, the lower limit value and the upper limit value of the reaction temperature may be, for example, ±1° C., ±2° C., ±3° C., ±4° C., and ±5° C. of the respective temperatures.

Unless otherwise specified, in the production method of the present specification, "room temperature" means a temperature of a laboratory, an experimental laboratory, or the like, and "room temperature" in examples of the present specification generally indicates a temperature from about 1° C. to about 30° C. (defined by the Japanese Pharmacopoeia). It preferably indicates a temperature of generally from about 5° C. to about 30° C., more preferably indicates a temperature of generally from about 15° C. to about 25° C., and even more preferably indicates a temperature of 20° C.±3° C.

The compounds in the present specification may form an acid addition salt depending on the type of substituent. Such a salt is not particularly limited as long as it is a pharmaceutically acceptable salt, and examples thereof include a salt of an inorganic acid, a salt of an organic acid, and the like. Preferred examples of salts of inorganic acids include salts of hydrochloric acid, hydrobromic acid, hydriodic acid, nitric acid, sulfuric acid, phosphoric acid, and the like. Preferred examples of salts of organic acids include salts of aliphatic monocarboxylic acids such as formic acid, acetic acid, trifluoroacetic acid, propionic acid, butyric acid, valeric acid, enanthic acid, capric acid, myristic acid, palmitic acid, stearic acid, lactic acid, sorbic acid, mandelic acid and the like; salts of aliphatic dicarboxylic acids such as oxalic acid, malonic acid, succinic acid, fumaric acid, maleic acid, malic acid, tartaric acid and the like; salts of aliphatic tricarboxylic acids such as citric acid and the like; salts of aromatic monocarboxylic acids such as benzoic acid, salicylic acid and the like; salts of aromatic dicarboxylic acids such as phthalic acid and the like; salts of organic carboxylic acids such as cinnamic acid, glycolic acid, pyruvic acid, oxylic acid, salicylic acid, N-acetylcysteine and the like; salts of organic sulfonic acids such as methanesulfonic acid, benzenesulfonic acid, p-toluenesulfonic acid and the like; and acid addition salts of acidic amino acids such as aspartic acid, glutamic acid and the like.

The salt described above can be obtained according to a conventional method, for example, by mixing a solution containing an appropriate amount of an acid with the compound described in the present specification to form desired salts, and then fractionating the salts and collecting them by filtration; or by distilling off the mixed solvent. Furthermore, the compound in the present specification or a salt thereof can form a solvate with a solvent such as water, ethanol, glycerol and the like. As a review article on salts, Handbook of Pharmaceutical Salts: Properties, Selection, and Use. Stahl & Wermuth (Wiley-VCH, 2002) has been published, and this book includes detailed description.

As shown in (Scheme 5) below, using the compound represented by Formula (A) as a starting material, the compound represented by Formula (B) or a salt thereof can be produced via the compounds of Formulas (A-5), (A-6), and (A-7).

(Scheme 5)

[C87]

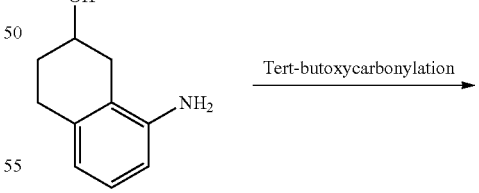

(A)

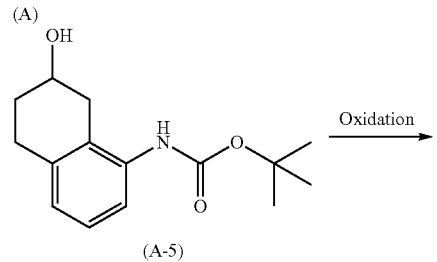

(A-5)

-continued

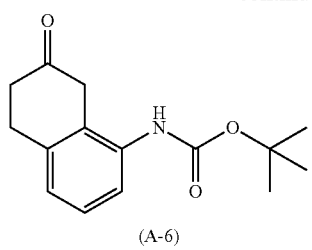

(A-6)

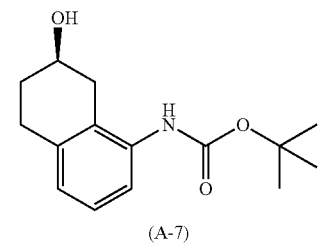

(A-7)

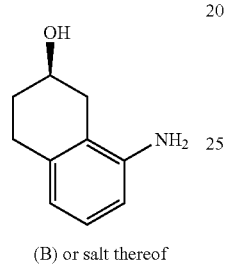

(B) or salt thereof

Furthermore, as shown in (Scheme 6) below, the compound represented by Formula (B) or a salt thereof can be produced by a method according to (Scheme 5) described above by changing a protecting group of an amino group of the compound represented by Formula (A) to a protecting group, which is other than a tert-butoxycarbonyl group, for example, a protecting group $P^1$ such as carbamate-based protecting groups such as a methoxycarbonyl group, an ethoxycarbonyl group, a benzyloxycarbonyl group, a 2,2,2-trichloroethoxycarbonyl group, a 9-fluorenylmethyloxycarbonyl group, an allyloxycarbonyl group and the like; sulfonyl-based protecting groups such as a methanesulfonyl group, an ethanesulfonyl group, a benzenesulfonyl group, a tosyl group, a nitrobenzenesulfonyl group and the like; and alkylcarbonyl-based or arylcarbonyl-based protecting groups such as an acetyl group, an ethylcarbonyl group, a trifluoroacetyl group, a benzoyl group and the like.

(Scheme 6)

[C88]

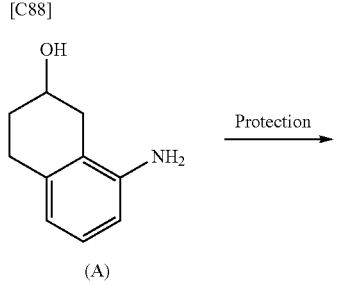

(A)

-continued

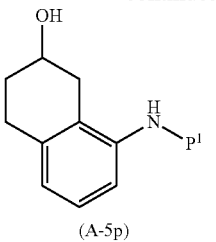

(A-5p)

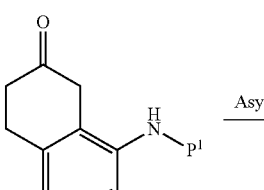

(A-6p)

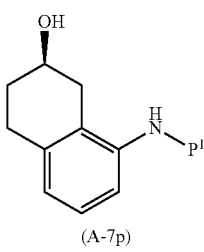

(A-7p)

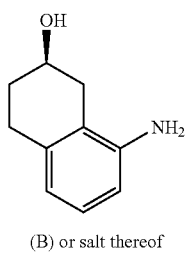

(B) or salt thereof $P^1$ = methoxycarbonyl group, ethoxycarbonyl group, benzyloxycarbonyl group, 2,2,2-trichloroethoxycarbonyl group, 9-fluorenylmethyloxycarbonyl group, allyloxycarbonyl group, methanesulfonyl group, ethanesulfonyl group, benzenesulfonyl group, tosyl group, nitrobenzenesulfonyl group, acetyl group, ethylcarbonyl group, trifluoroacetyl group, benzoyl group, etc.

Conditions for protection of the compound represented by Formula (A) by the protecting group $P^1$ or deprotection of the protecting group $P^1$ of the compound represented by Formula (A-7p) can be selected according to the type of protecting group $P^1$ by a method known from a literature, for example, a protection and deprotection method disclosed in the book, "Protective Groups in Organic Synthesis, 4th Edition, 2007, John Wiley & Sons, Greene et al."

As shown in (Scheme 7) below, using the compound represented by Formula (SM8) as a starting material, the compound represented by Formula (B) can be produced via the compound represented by Formula (A8).

(Scheme 7)

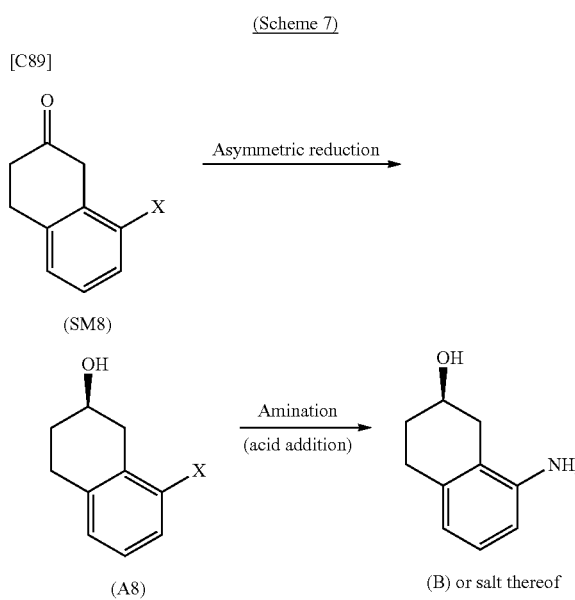

(Scheme 8)

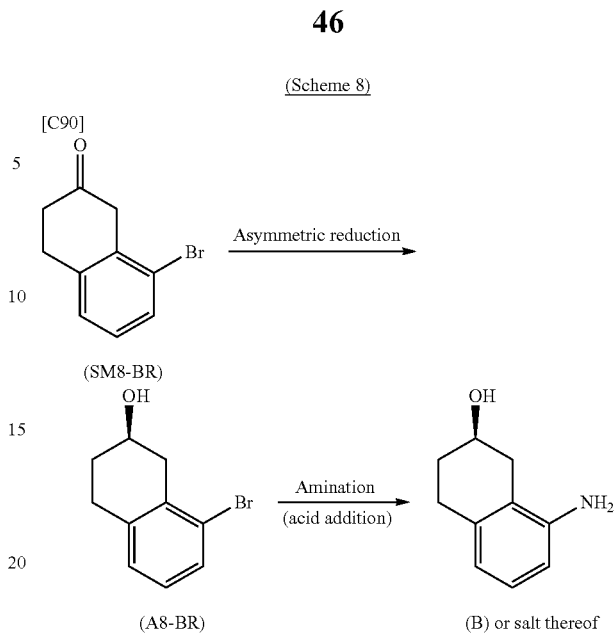

Furthermore, as shown in (Scheme 8) below, using the compound represented by Formula (SM8-BR) as a starting material, the compound represented by Formula (B) can be produced via the compound represented by Formula (A8-BR).

As shown in (Scheme 9) below, using the compound represented by Formula (A) as a starting material, the compound represented by Formula (I) can be produced via the compound represented by Formula (B). In (Scheme 9), the compound represented by Formula (B-HA) represents a salt of an acid HA of the compound represented by Formula (B), where HA represents an acid.

(Scheme 9)

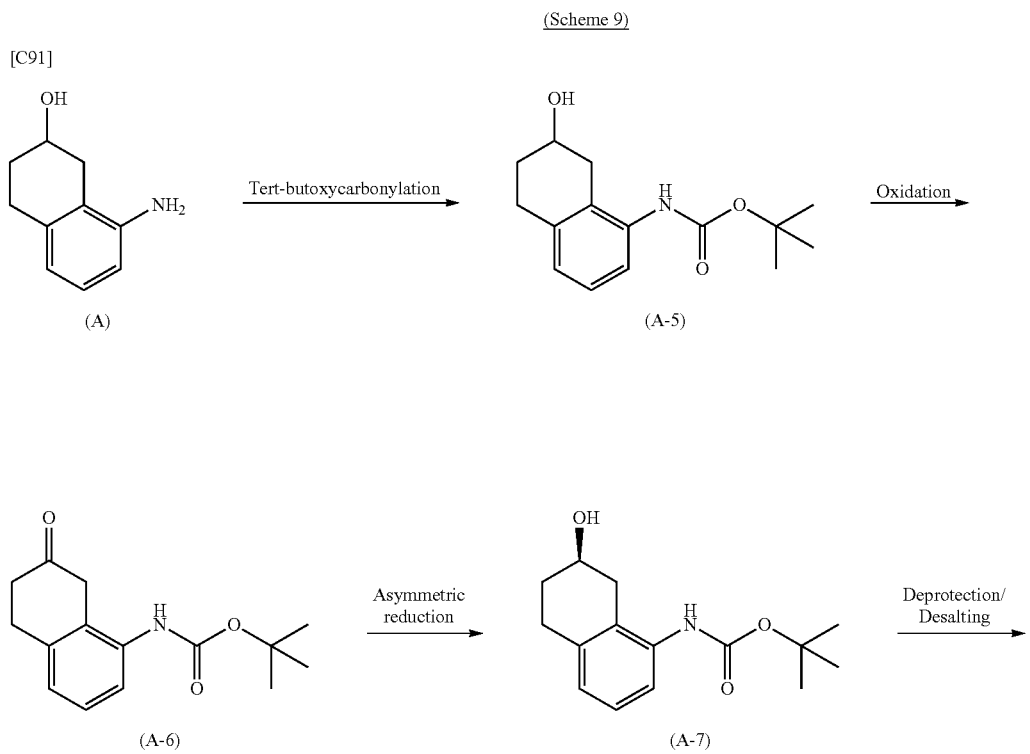

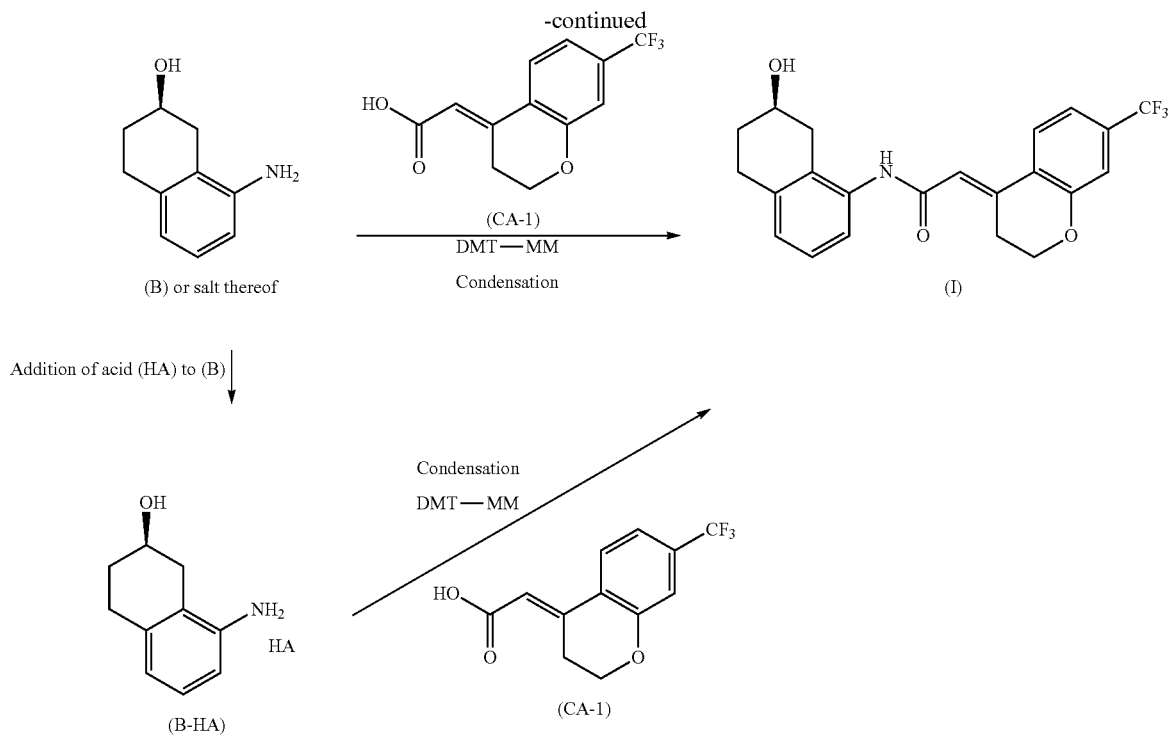

Furthermore, as shown in (Scheme 10) below, using the compound represented by Formula (A) as a starting material, the compound represented by Formula (I) can be produced via the compound represented by Formula (B). The definition of a substituent P¹ in (Scheme 10) is the same as the definition in (Scheme 6) described above. In (Scheme 10), the compound represented by Formula (B-HA) represents a salt of an acid HA of the compound represented by Formula (B), where HA represents an acid.

(Scheme 10)

[C92]

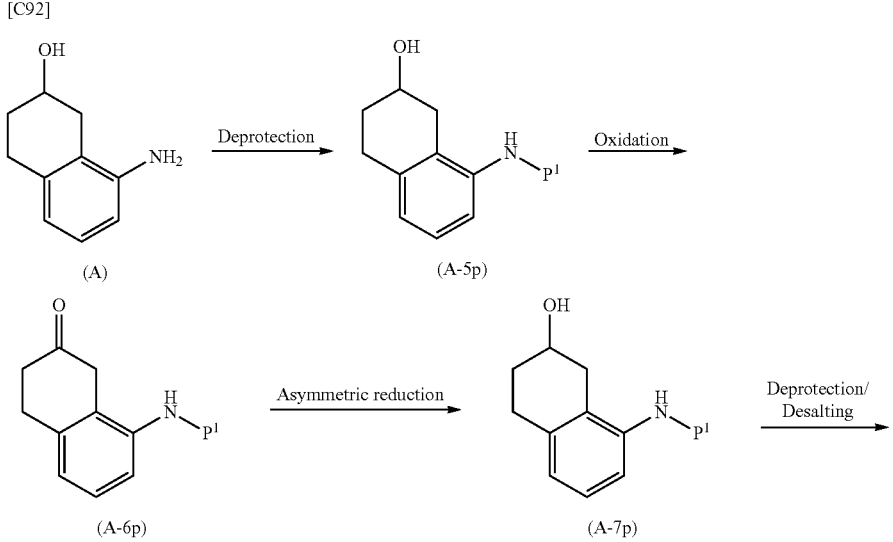

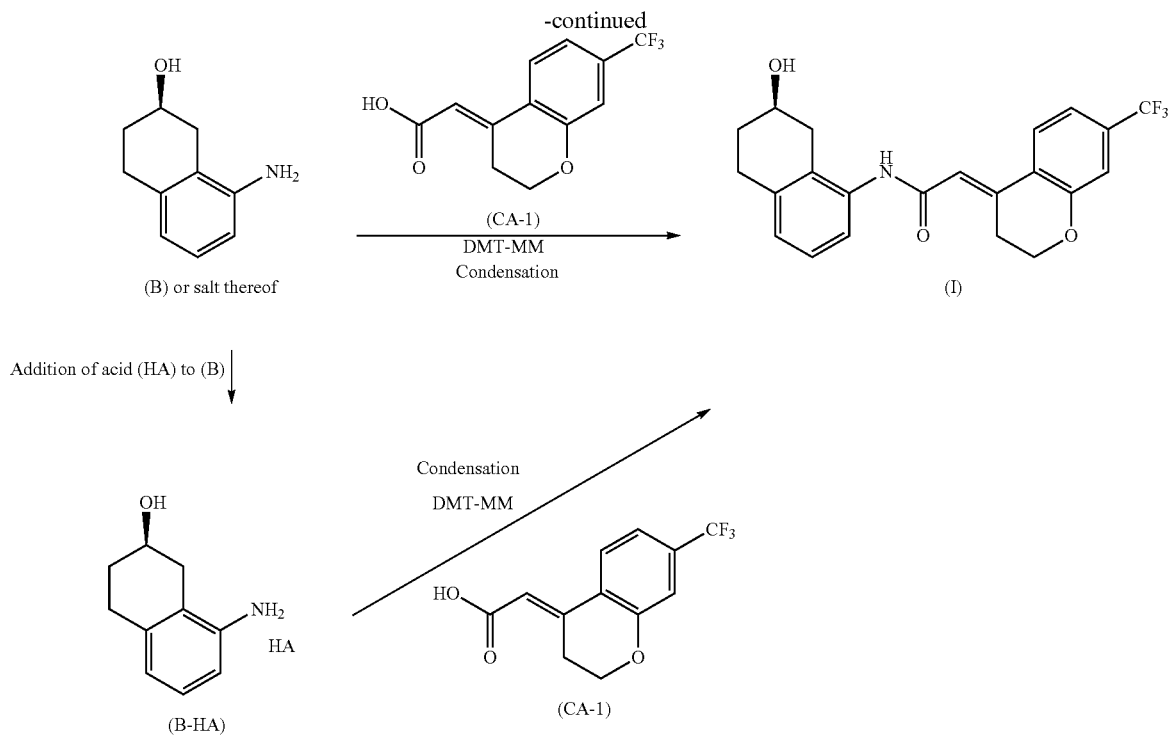
Furthermore, as shown in (Scheme 11) below, using the compound represented by Formula (SM8) as a starting material, the compound represented by Formula (I) can be produced via the compound represented by Formula (B). In (Scheme 11), the compound represented by Formula (B-HA) represents a salt of an acid HA of the compound represented by Formula (B), where HA represents an acid.
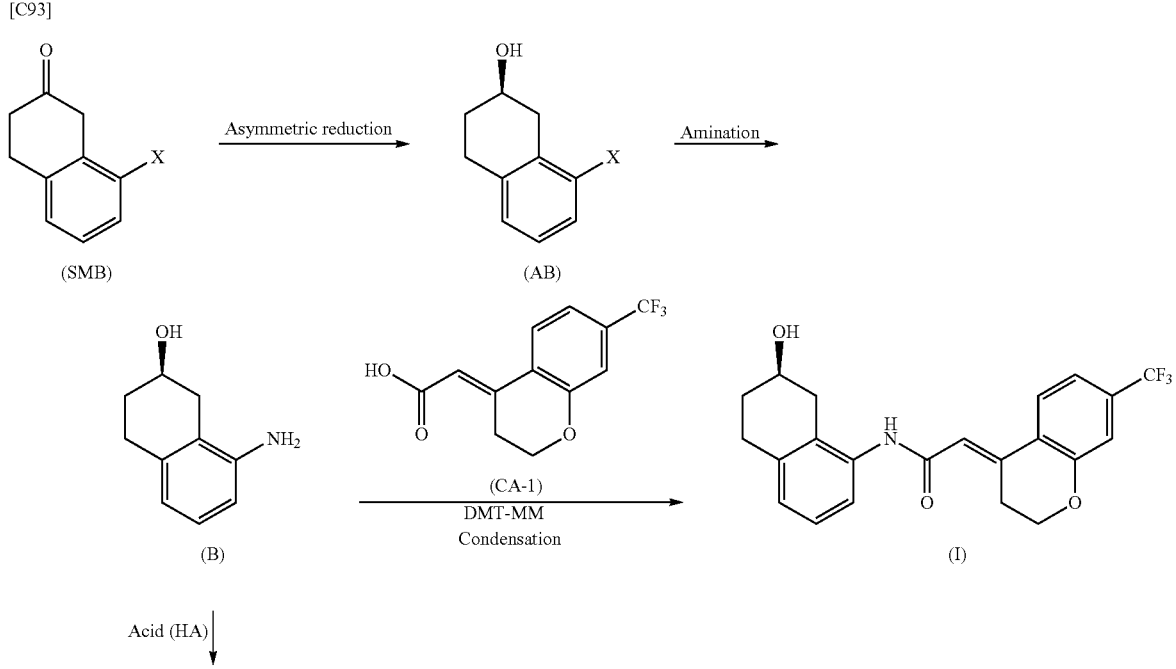

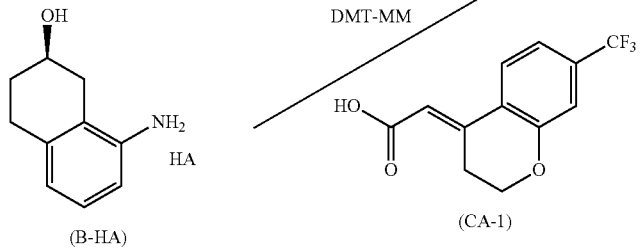

Furthermore, as shown in (Scheme 12) below, using the compound represented by Formula (SM8-BR) as a starting material, the compound represented by Formula (I) can be produced via the compound represented by Formula (B). In (Scheme 12), the compound represented by Formula (B-HA) represents a salt of an acid HA of the compound represented by Formula (B), where HA represents an acid.

In the present specification, the compounds of Formula (A), Formula (A-5), and Formula (A-5p) which are racemates include an (R) form and an (S) form. This means that, for example, Formula (A-5) includes Formula (A-5S) and Formula (A-5R) (=Formula (A-7)).

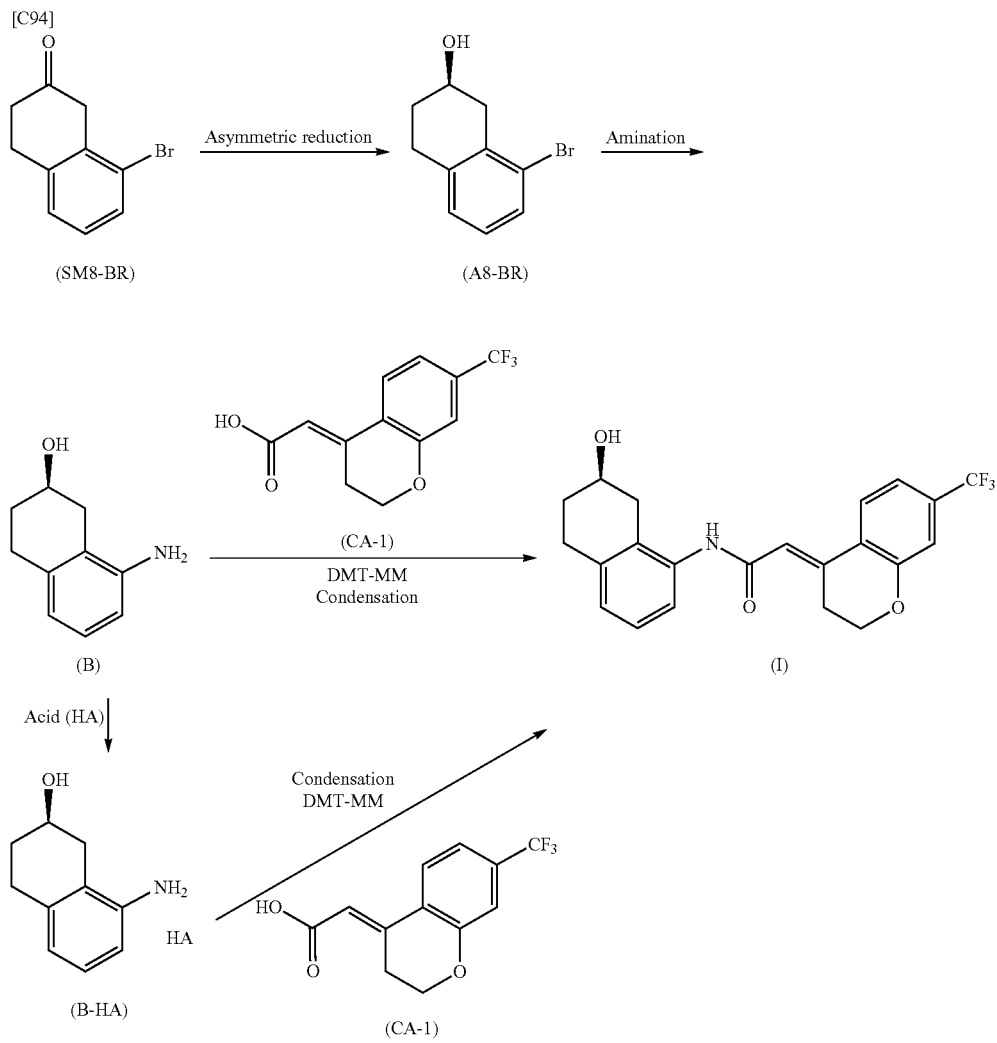

[C95]

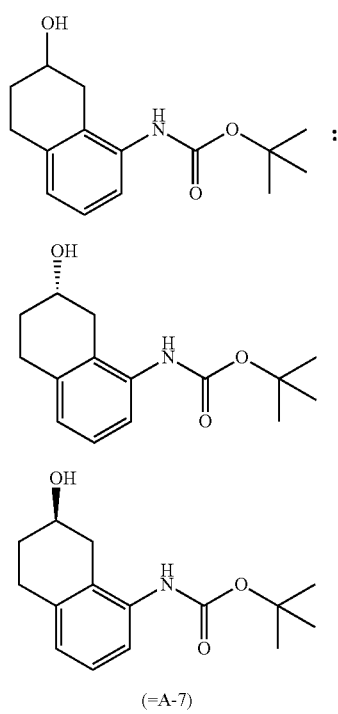

[Asymmetric Reduction of Ketones]

Various reactions are known as a method for converting a keto group in a molecule to a chiral alcohol group. For example, there is a method in which a keto group is converted to a racemic alcohol group using a reducing agent (sodium borohydride, lithium aluminum hydride (LAH), borane-tetrahydrofuran ($BH_3$-THF), and the like), and thereafter, induced to a chiral alcohol group by a method such as a fractional recrystallization method (a method in which a crystalline diastereomer is obtained by ionic bonding of an optical resolution agent to a racemate, and this crystalline diastereomer is fractionated by recrystallization and neutralized if desired to obtain a free chiral compound), a diastereomer method (refer to WO 2009/055749), and a chiral column method (refer to WO 2009/050289).

Furthermore, the following reactions are known: an asymmetric reductive reaction using a transition metal catalyst (for example, Ru, Rh and the like) (WO 2009/050289; Organometallics 10, p 500-, 1991; and the like), an asymmetric reductive reaction in which $Al(CH_3)_3$ and BINOL as a ligand are combined (Angew. Chem. Int. Ed., 41, p 1020-, 2002), an asymmetric reductive reaction using a chiral Ru (BINAP) catalyst (J. Am. Chem. Soc. 110, p 629-, 1988), an asymmetric reductive reaction using oxazaborolidine (J. Am. Chem. Soc. 109, p 5551-, 1987), an asymmetric reductive reaction using a biocatalyst (yeast, fungus, mold, enzyme, and the like) (refer to Table 1), and the like.

In some aspects, the asymmetric reduction is preferably performed using a biocatalyst. The asymmetric reduction using a biocatalyst has advantages in that not only it has high stereoselectivity, an organic solvent and/or water can be used as a reaction solvent, the reaction proceeds under mild conditions (normal temperature, normal pressure), and it is cheaper than a chemical catalyst, and the like, but also it is a reaction that has been attracting attention in recent years for being an environmentally friendly reaction because an amount of waste after the reaction can be reduced, and is also a useful reaction for easily obtaining a chiral compound.

Generally, in the asymmetric reductive reaction using an enzyme, a chemical yield (%) and an optically active yield (ee %) of a chiral compound to be obtained vary depending on reaction specificity (selectivity for type of enzyme-specific reaction), substrate specificity (selectivity for type of substrate), and reaction conditions (reaction temperature, pH, solvent, reaction time, and the like). Many enzymes have very high reaction specificity, and reactions catalyzed by one enzyme are limited, but there are various enzymes, i.e., enzymes with higher substrate specificity or enzymes with lower substrate specificity. Accordingly, for example, when a keto group is asymmetrically reduced to a chiral alcohol group, even if an enzyme from which a favorable chemical yield and optically active yield are obtained from compounds having a similar structure to that of a substrate (ketone compound) to be used is selected and an enzymatic reaction is performed under the same conditions, a desired chiral alcohol compound may not be obtained at the same chemical yield and optically active yield.

For example, biocatalysts, which can selectively reduce a keto group of β-tetralone [CAS number: 530-93-8] to a chiral alcohol, shown in Table 1 are known.

TABLE 1

| Biocatalyst | Origin | Disclosure document |
| --- | --- | --- |
| Enzyme | Magnaporthe grisea expressed in Escherichia coli BL21 | Angewandte Chemie, International Edition, 51(11), p2643-2646, 2012 |
| | whole cells of Kluyveromyces marxianus CBS 6556 | Tetrahedron Asymmetry, 22(23), p1985-1993, 2011 |
| | Thermoanaerobacter ethanolicus (TeSADH) | Practical Methods for Biocatalysis and Biotransformations, p284-287, 2010 |
| | whole cells of Didymosphaeria igniaria KCH6670 | Journal of Industrial Microbiology & Biotechnology, 37(11), p1121-1130, 2010 |
| | Paracoccus pantotrophus DSM 11072 overexpressed in E.coli | ChemSusChem, 1(5), p431-436, 2008 |
| | Ralstonia sp. DSM 6428 (RasADH) | Journal of Organic Chemistry, 73(15), p6003-6005, 2008 |
| | Sphingobium yanoikuyae | Organic Letters, 10(11), p2155-2158, 2008 |
| | Thermoanaerobacter ethanolicus expressed in Escherichia coli | WO 2008/013949 |
| | Thermoanaerobacter ethanolicus W110A | Angewandte Chemie, International Edition, 46(17), p3091-3094, 2007 |

TABLE 1-continued

| Biocatalyst | Origin | Disclosure document |
|---|---|---|
| | Rhodococcus ruber DSM 44541 | Organic Letters, 9(11), p2163-2166, 2007 |
| | W110A TESADH. | Journal of Organic Chemistiy, 72(1), p30-34, 2007 |
| | Lactobacillus kefir. sp | Advanced Synthesis & Catalysis, 350(14 + 15), p2322-2328, 2008 |
| Yeast | Candida viswanathii | Biocatalysis and Biotransformation, 31(3), p123-131, 2013 |
| Fungus | Absidia cylindrospora KCh 336 | Current Microbiology, 65(2), p189-194, 2012 |
| | Lyophilised cells of Comamonas sp. | Tetrahedron: Asymmetry, 19(16), p1954-1958, 2008 |
| | Rhodococcus ruber DSM 44541 | Journal of Organic Chemistiy, 68(2), p402-406, 2003 |
| | Saccharomyces montanus cbs 6771 | Tetrahedron: Asymmetry, 7(10), p2983-2996, 1996 |
| Mold | Aspergillus ochraceus atcc 1009. | Tetrahedron: Asymmetry, 7(10), p2983-2996, 1996 |
| | Mucor racemosus | |
| | rhizopus arrhizus atcc 11145 | |
| Cell culture solution | Lycoperiscumesculentum (tomato) | International Journal of ChemTech Research, 4(1), p203-207, 2012 |
| Plant | Daucas Carota root ext | U.S. Patent Application Publication No. 2004-0082043 |
| | Coryneum betulinum KCh 6534 | Current Microbiology, 65(2), p189-194, 2012 |
| | Fusarium culmorum | Biocatalysis and Biotransformation, 27(3), p179-185, 2009 |

[Flow Chemistry]

For synthetic reactions, there are generally a flow method (flow chemistry) and a batch method. The flow chemistry is a continuous synthesis method using a reaction device that sends a liquid from a vessel containing two or more different kinds of solutions (for example, raw material+solvent, reagent+solvent, and the like) through a tube to a reactor, and then to a recovery drum, at a constant flow rate using a pump.

The flow chemistry can be used when converting the compound represented by Formula (A-5) to the compound represented by Formula (A-6) by an oxidation reaction. FIG. 1 shows an example of a reaction device used in the flow chemistry. The reaction device shown in FIG. 1 has nitrogen inlets (L1, L2, L3, L4); a vessel (M1) containing a raw material, TEMPO, and dichloromethane; a vessel (M2) containing KBr, NaHCO$_3$, and water; a vessel (M3) containing 5.0 wt % NaClO; pumps (P1, P2, P3); pre-cooling tubes (T1, T2, T3); stirrers (S1, S2, S3); and reactor (R1, R2, R3).

The reaction device of FIG. 1 is used as follows, for example. First, a raw material (the compound represented by Formula (A-5)), TEMPO, and dichloromethane are put in the vessel M1, KBr, sodium hydrogen carbonate, and water are put in the vessel M2, and 5.0 wt % NaClO is put in the vessel M3. While flowing nitrogen gas from the respective nitrogen inlets L1, L2, L3, L4, the reagents are flowed from the respective vessels M1, M2, M3 at a predetermined flow rate using the respective pumps P1, P2, P3, then are passed through the respective pre-cooling tubes T1, T2, T3, then are sequentially passed through the reactor R1, the reactor R2, and the reactor R3, and thereby are poured into a recovery drum CD. Then, a target product (the compound represented by Formula (A-6)) is obtained from the recovery drum CD.

The flow chemistry can also be applied to reactions which is difficult to keep safety by a normal batch method (refer to a review article on flow chemistry ChemSusChem, 5(2), Special Issue; Flow Chemistry, p 213-439, Feb. 13, 2012).

The batch method is a general synthetic reaction and is a method of purifying a product obtained after performing a reaction using a reactor. The batch method has the advantage in that a compound can be synthesized in several steps.

In the flow method (flow chemistry), a reaction is performed in flow mode using, for example, a continuous stirred tank reactor (CSTR) as a reaction device. In the flow method, because the reaction can be performed in a small reactor, a reaction efficiency is high and reaction conditions can be precisely controlled, so a target product can be stably supplied.

[Amination Reaction]

A method (amination reaction) of converting a halogen atom of a halogenated aryl to an amino group can be performed in the presence of a metal catalyst and in the presence or absence of a ligand using, as a nitrogen source, a compound represented by NHR$^A$R$^B$ (where R$^A$ and R$^B$ each independently represent a hydrogen atom, or a substituent such as a methyl group, an ethyl group, a benzyl group, and the like), R$^C$CONH$_2$ (where R$^C$ independently represents a substituent such as a methyl group, an ethyl group, a benzyl group, a methoxy group, an ethoxy group, a tert-butoxy group, a benzyloxy group, and the like), or the like.

For an amination reaction of a halogenated aryl using ammonia as a nitrogen source, for example, the following method using a metal catalyst is known as a method known from a literature, but a method is not limited thereto. Pd$_2$(dba)$_3$ (J. Am. Chem. Soc., 129(34), p 10354-10355, 2007), PdCl$_2$-Josiphos complex (J. Am. Chem. Soc., 128 (31), p 10028-10029, 2006), CuI (Chem. Commun., 26, p 3052-3054, 2008; J. Org. Chem., 74(12), p 4542-4546, 2009), Cu(OAc)$_2$ (Angew. Chem. Int. Ed., 48(2), p 337-339, 2009), Cu$_2$O (Ukrainskii Khimiche skii Zhurnal (Russian Edition), 53(12), P 1299-302, 1987).

For example, for an amination reaction to 8-halo-1,2,3, 4-tetrahydronaphthalen-2-ol in which a secondary alcohol is present in a molecule, an amination reaction using Pd$_2$(dba)$_3$ as a metal catalyst and tert-butyl carbamate as a nitrogen source is known, but examples using other metal catalysts are not known.

In some aspects, the amination reaction is preferably a reaction that enables direct introduction of an amino group by ammonia. Alternatively, it is also possible to introduce an amino group by deprotecting a protecting group after substitution with, for example, a protected amino compound such as NHR$^{A1}$R$^{B1}$ (where R$^{A1}$ is a hydrogen atom, and R$^{B1}$ represents a protecting group of an amino group such as a benzyl group, a 4-methoxybenzyl, and the like), and R$^C$CONH$_2$ (where R$^C$ independently represents a substituent such as a methyl group, an ethyl group, a benzyl group, a methoxy group, an ethoxy group, a tert-butoxy group, a benzyloxy group, and the like). However, since the amination reaction using a protected amino compound requires a step of deprotecting a protecting group, the reaction that enables direct introduction of an amino group by ammonia is preferable when considering large-scale synthesis or industrial production.

[Condensation Reaction]

In general, regarding a condensation reaction of a compound having a carboxyl group and a compound having an amino group, an amide bond can be formed by performing a condensation reaction using, for example, a condensation agent such as 1,3-dicyclohexylcarbodiimide (DCC), 1-ethyl-3-(3'-dimethylaminopropyl)carbodiimide hydrochloride (WSC HCl), benzotriazol-1-yloxytris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), and the like (refer to, for example, Experimental Chemistry Course 22, 4th Edition, Organic Synthesis IV: Acids, Amino Acids, Peptides, pp. 193-309, 1992, Maruzen; and the like).

As a result of the examination on the condensation agent, the inventors of the present invention have found that the compound represented by Formula (I) can be easily produced in a high yield by using particularly DMT-MM as a condensation agent in a condensation reaction of the compound represented by Formula (B) which has both a hydroxyl group and an anilinic amino group and heterocyclidene acetic acid represented by Formula (CA-1) which has a carboxyl group.

All publications cited in the present specification, such as prior art documents, unexamined patent publications, patent publications, and other patent documents, are incorporated in the present specification by reference in their entirety. The present specification includes disclosures of the scope of claims, specifications, and drawings of Chinese Patent Application No. 201910783254.8 (filed on Aug. 23, 2019), International Patent Application No. PCT/JP2019/036451 (filed on Sep. 18, 2019), and Chinese Patent Application No. 202010355546.4 (filed on Apr. 29, 2020), which are the basis for claiming priority of the present application.

EXAMPLES

Hereinafter, the present invention will be specifically described with reference to examples, but the present invention is not limited thereto.

Bruker AVANCE III 400 MHz NMR spectrometer (equipped with a 5 mm Bruker PABBO Z-gradient probe and TOPSPIN 3.5 software) was used for measurement of nuclear magnetic resonance (NMR) spectra of the compounds represented by Formula (A-5), Formula (A-6), Formula (A-7), and Formula (B). Furthermore, JEOL JNM-LA300 FT-NMR (JEOL Ltd.) was used for measurement of nuclear magnetic resonance (NMR) spectra of a bromate salt of the compound represented by Formula (B) and the compound represented by Formula (I).

The compounds represented by Formula (A-5), Formula (A-6), Formula (A-7), and Formula (B) were measured by high-performance liquid chromatography (HPLC) under the following conditions.

TABLE 2

[HPLC analysis conditions for compound represented by Formula (A-5), Formula (A-6), and Formula (A-7)]

| | |
|---|---|
| Measuring instrument | Agilent 1260 HPLC with UV detector or equivalent |
| Column | Waters Xbridge C18, (150 mm × 4.6 mm, 3.5 μm) (PN: 186003034) |
| Measurement wavelength | 210 nm |
| Column temperature | 40° C. |
| Flow rate | 1.0 mL/min |
| Injection capacity | 5 μL |
| Sample concentration | Compound represented by Formula (A-5) or Formula (A-7): 0.2 mg/mL, Compound represented by Formula (A-6): 0.25 mg/mL |
| Performance time | 20 minutes |
| Data collection time | 20 minutes |
| Dilution agent | $CH_3CN$ |
| Mobile phase A | Aqueous solution of 5 mM $NH_4Ac$ (Preparation example: 770 mg of $NH_4Ac$ is accurately weighed in and thoroughly mixed with 2,000 mL of pure water, and the mixture is degassed by ultrasonic waves) |
| Mobile phase B | $CH_3CN$ |
| Gradient program | |

| Time (min) | Mobile phase A (%) | Mobile phase B (%) |
|---|---|---|
| Initial time | 95 | 5 |
| 12.00 | 10 | 90 |
| 14.00 | 10 | 90 |
| 15.00 | 95 | 5 |
| 20.00 | 95 | 5 |

Rebalancing time: 5 minutes

TABLE 3

[Retention time (RT) of each compound]

| Compound | RT (min) | Relative retention time (RRT) |
|---|---|---|
| Ethyl acetate | 5.8 | 0.62 |
| Compound represented by Formula (A) | 6.2 | 0.67 |
| Dichloromethane | 7.0 | 0.75 |
| Compound represented by Formula (A-5) or Formula (A-7) | 9.3 | 1.00 |
| TEMPO | 9.5 | 1.02 |
| Compound represented by Formula (A-6) | 9.8 | 1.05 |
| Toluene | 11.0 | 1.18 |

TABLE 4

[HPLC analysis conditions for compound represented by Formula (B)]

| | |
|---|---|
| Measuring instrument | Shimadzu LC-20A HPLC with UV detector |
| Column | ACE 3 C18 (150 mm × 4.6 mm, 3 μm) |
| Measurement wavelength | 213 nm |

TABLE 4-continued

[HPLC analysis conditions for compound represented by Formula (B)]

| | |
|---|---|
| Column temperature | 35° C. |
| Flow rate | 1.0 mL/min |
| Sample concentration | Compound represented by Formula B: 0.1 mg/mL, Hydrochloride salt of compound represented by Formula B: 0.12 mg/mL |
| Injection capacity | 5 μL |
| Mobile phase | Mobile phase A: aqueous solution of 5 mM NH$_4$Ac |
| | Mobile phase B: CH$_3$CN |
| Gradient program | Time (min) / Mobile phase A (%) / Mobile phase B (%) |
| | 0.01 / 95 / 5 |
| | 4.00 / 70 / 30 |
| | 10.0 / 10 / 90 |
| | 11.00 / 10 / 90 |
| | 12.00 / 95 / 5 |
| | 16.0 / stop / stop |
| Performance time | 16 minutes |
| Dilution agent | MeOH |

TABLE 5

[Retention time (RT) for each compound]

| Compound | RT (min) | Relative retention time (RRT) |
|---|---|---|
| Formula (B) | 7.0 | 1.00 |
| Formula (A-7) | 9.6 | 1.36 |
| Toluene | 11.0 | 1.57 |

TABLE 6

[Chiral analysis conditions by HPLC for compound represented by Formula (A-7)]

| | |
|---|---|
| Measuring instrument | Shimadzu LC-20A HPLC with UV detector or equivalent |
| Column | Daicel Chiralpak AD-H (250 × 4.6 mm, 5.0 μm) column, PN:19325 |
| Measurement wavelength | 230 nm |
| Column temperature | 35° C. |
| Flow rate | 1.0 mL/min |
| Injection capacity | 5 μL |
| Sample concentration | 2.5 mg/mL |
| Data collection time | 20 min |
| Performance time | 20 min |
| Dilution agent | EtOH |
| Mobile phase | Mixed solution of 0.1% diethylamine n-hexane/ethanol (9/1, v/v) (Preparation example: 900 mL of n-hexane and 100 mL of ethanol are thoroughly mixed, and next, 1 mL of diethylamine is added to and mixed with the mixed solution of n-hexane and ethanol) |
| Isocratic program | Time (min) / Formula (A-7) (%) |
| | 0.00 / 100 |
| | 20.00 / 100 |

TABLE 7

[Retention time (RT) for each compound]

| Compound | RT (min) | Relative retention time (RRT) |
|---|---|---|
| Compound represented by Formula (A-7) | 8.1 | 1.00 |
| Enantiomer of compound represented by Formula (A-7) | 9.9 | 1.22 |

Furthermore, a liquid chromatography-mass spectrometry (LC-Mass) spectrum of the bromate salt of the compound represented by Formula (B) and the compound represented by Formula (I) was measured by the following method.

[UPLC] Waters AQUITY UPLC system and BEH C18 column (2.1 mm×50 mm, 1.7 m) (Waters) were used, and a mobile phase and gradient conditions of acetonitrile:aqueous solution of 0.05% trifluoroacetic acid=5:95 (0 minutes) to 95:5 (1.0 minute) to 95:5 (1.6 minutes) to 5:95 (2.0 minutes) were used.

In $^1$H-NMR data, s means singlet, d means doublet, t means triplet, q means quartet, m means multiplet, brs means broad as the pattern of NMR signals, J means coupling constant, Hz means Hertz, DMSO-d$_6$ is deuterated dimethyl sulfoxide, and CDCl$_3$ means deuterated chloroform. In $^1$H-NMR data, signals, which cannot be confirmed because of being broadband signals, such as protons of a hydroxyl group (OH), an amino group (NH$_2$), and an amide group (CONH), are not described in the data.

In LC-Mass data, M means molecular weight, RT means retention time, and [M+H]$^+$ means molecular ion peak.

(Examples 1a to 1d) Synthesis of tert-butyl(7-hydroxy-5,6,7,8-tetrahydronaphthalen-1-yl)carbamate (A-5)

[C96]

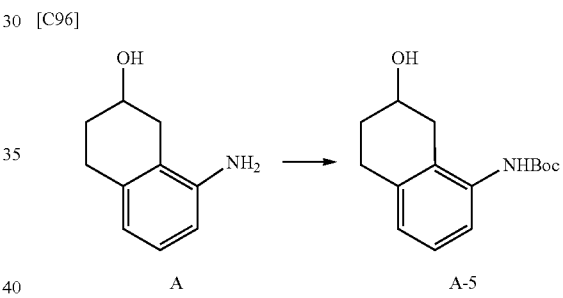

Example 1a

Di-tert-butyl dicarbonate (Boc$_2$O) (0.74 g) was added to a solution of the compound represented by Formula A (produced according to a production method disclosed in WO 2009/050289) (0.5 g) and sodium hydrogen carbonate (0.154 g) in 1,4-dioxane (5 mL)-water (5 mL), and the mixture was stirred at a reaction temperature of 20° C. to 30° C. for 22 hours. Sodium hydrogen carbonate (0.104 g) was further added to the mixture, and the mixture was stirred at a reaction temperature of 20° C. to 30° C. for 18 hours. Di-tert-butyl dicarbonate (0.15 g) was further added to the mixture, and the mixture was stirred at a reaction temperature of 20° C. to 30° C. for 5 hours. Di-tert-butyl dicarbonate (0.15 g) was further added to the mixture, and the mixture was stirred at a reaction temperature of 20° C. to 30° C. for 16 hours. Di-tert-butyl dicarbonate (0.1 g) was further added to the mixture, and the mixture was further stirred at a reaction temperature of 20° C. to 30° C. for 1 hour. Ethyl acetate was added to the reaction solution, and the organic layer was fractionated. The aqueous layer was washed with ethyl acetate, and the organic layer was combined with the previously obtained organic layer, and then washed with brine. The organic layer was concentrated under reduced pressure, and the obtained residue was solidified with dichloromethane and n-heptane to obtain the title compound (0.46 g).

Example 1b

Di-tert-butyl dicarbonate (Boc$_2$O) (1.61 g) was added to a solution of the compound represented by Formula A (produced according to a production method disclosed in WO 2009/050289) (1.0 g) and sodium hydrogen carbonate (1.55 g) in tetrahydrofuran (10 mL)-water (10 mL), and the mixture was stirred at a reaction temperature of 45° C. to 55° C. for 17 hours. Di-tert-butyl dicarbonate (0.13 g) was further added to the mixture, and the mixture was stirred at a reaction temperature of 45° C. to 55° C. for 2 hours. After cooling the reaction solution to room temperature, methyl tert-butyl ether (MTBE) was added to the reaction solution, and a pH was adjusted to 5 to 6 with a 10 w/v % citric acid solution, then the organic layer was fractionated. The aqueous layer was extracted with methyl tert-butyl ether, and the organic layer was combined with the previously obtained organic layer, and then washed with water and brine. The organic layer was concentrated under reduced pressure, and the obtained residue was solidified with dichloromethane and n-heptane to obtain the title compound (1.34 g).

Example 1c

Di-tert-butyl dicarbonate (Boc$_2$O) (17.4 g) was added to a solution of the compound represented by Formula A (produced according to a production method disclosed in WO 2009/050289) (10 g) and sodium hydrogen carbonate (15.5 g) in tetrahydrofuran (100 mL)-water (100 mL), and the mixture was stirred at a reaction temperature of 45° C. to 55° C. for 17 hours. Di-tert-butyl dicarbonate (1.3 g) was further added to the mixture, and the mixture was stirred at a reaction temperature of 45° C. to 55° C. for 2 hours. Di-tert-butyl dicarbonate (1.3 g) was further added to the mixture, and the mixture was further stirred at a reaction temperature of 45° C. to 55° C. for 1 hour. After cooling the reaction solution to room temperature, methyl tert-butyl ether (MTBE) was added to the reaction solution, and a pH was adjusted to 5 to 6 with a 10% citric acid solution, then the organic layer was fractionated. The aqueous layer was extracted with methyl tert-butyl ether, and the organic layer was combined with the previously obtained organic layer, and then washed with water and brine. The organic layer was concentrated under reduced pressure, and the obtained residue was solidified with dichloromethane and n-heptane to obtain the title compound (15.1 g).

Example 1d

A solution of the compound represented by Formula A (produced according to a production method disclosed in WO 2009/050289) (218.5 g) in tetrahydrofuran (1.9 L) was adjusted to a temperature of 20° C. to 30° C., and an aqueous solution of sodium hydrogen carbonate (319 g (3.2 eq) of sodium carbonate, and 1.9 L of water) was added to the solution over 10 minutes at a temperature of 20° C. to 30° C. The temperature of the above mixed solution was set to 0° C. to 10° C., and di-tert-butyl dicarbonate (413 g) was added to the mixed solution over 15 minutes while maintaining the same temperature. A reaction temperature was set to 45° C. to 55° C., and the mixed solution was stirred at the same temperature for 18 hours. After cooling the reaction temperature to 20° C. to 30° C., methyl tert-butyl ether (1.9 L) was added to the reaction solution, and the mixed solution was stirred at 20° C. to 30° C. for 10 minutes. A 10% citric acid solution (2.5 L) was added to the mixed solution, and the organic layer was fractionated. The aqueous layer was extracted with methyl tert-butyl ether (1 L×2 times), and the organic layer was combined with the previously obtained organic layer, and then washed with water (1 L×2 times). After concentrating the organic layer under reduced pressure until it was about 500 mL, an operation of adding dichloromethane (1 L) and concentrate the organic layer under reduced pressure until the organic layer was about 500 mL was performed twice, then n-heptane (1 L) was added and the organic layer was concentrated under reduced pressure until the organic layer was about 500 mL, n-heptane (800 L) was added and the organic layer was concentrated under reduced pressure until the organic layer was about 600 mL, and dichloromethane (300 mL) and n-heptane (600 mL) were added and the organic layer was concentrated under reduced pressure until the organic layer was about 600 mL, then dichloromethane (1 L) was added, and activated carbon (21 g) was added thereto, and the mixed solution was stirred at 20° C. to 30° C. for 2 hours. Then, the mixed solution was filtered, and the filtrate was concentrated under reduced pressure until it was about 500 mL, then dichloromethane (800 mL) was added thereto, and the solution was concentrated under reduced pressure until it was about 500 mL. Dichloromethane (800 mL) was added and the solution was filtered to obtain a solid. The obtained solid was dried at 35° C. for 15 hours to obtain the title compound (303.3 g) as a grayish-black solid.

[Data of Physical Properties of Compound Represented by Formula (A-5)]

($^1$H NMR, 400 MHz, manufacturer: Bruker, DMSO-d$_6$, δ ppm)

8.36 (s, 1H), 7.09 (d, 1H, J=7 Hz), 7.03 (t, 1H, J=7 Hz), 6.87 (d, 1H, J=7 Hz), 4.78 (d, 1H, J=4 Hz), 3.90-3.84 (m, 1H), 2.89-2.81 (m, 2H), 2.75-2.65 (m, 1H), 2.42 (dd, 1H, J=7 Hz, 17 Hz), 1.90-1.80 (m, 1H), 1.62-1.53 (m, 1H), 1.46 (s, 9H)

(Examples 2a to 2f) Synthesis of tert-butyl(7-oxo-5,6,7,8-tetrahydronaphthalen-1-yl)carbamate (A-6)

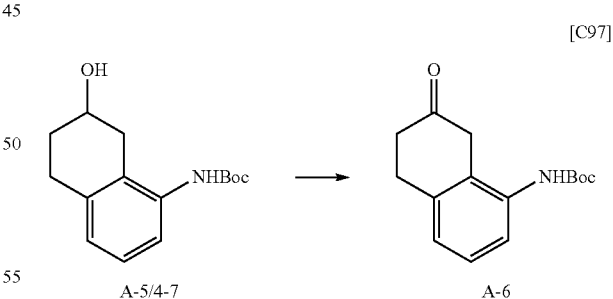

[C97]

A-5/4-7     A-6

Example 2a

Using tert-butyl (R)-(7-hydroxy-5,6,7,8-tetrahydronaphthalen-1-yl)carbamate (Formula (A-7)) (0.5 g) obtained from (R)-8-amino-1,2,3,4-tetrahydronaphthalen-2-ol in the same manner as in the methods of (Examples 1a to 1d), an oxidation reaction was performed under conditions of reagents shown in the following table, in a solvent (dichloromethane (12.5 mL)-water (7.5 mL)) at a reaction temperature (0° C. to 5° C.), and it was confirmed that the title compound was obtained (TPC purity using HPLC (TPC=in process control)).

TABLE 8

| No. | Reagent | | | | IPC purity A6 (%) | | | |
|---|---|---|---|---|---|---|---|---|
| | | | | 10% | Reaction time | | | |
| | TEMPO (eq) | NaHCO₃ (eq) | KBr (eq) | NaClO (eq) | 10 (min) | 30 (min) | 60 (min) | 18 (h) |
| 1 | 0.05 | 4 | 0.05 | 2 | 35.6 | 50.6 | 55.7 | 61.4 |
| 2 | 0.275 | 3 | 0.125 | 1.7 | 87.0 | 87.9 | 88.9 | 78.9 |
| 3 | 0.5 | 2 | 0.05 | 2 | 78.0 | 89.2 | 88.9 | 77.5 |
| 4 | 0.05 | 2 | 0.2 | 2 | 30.5 | 47.0 | 55.9 | 58.3 |
| 5 | 0.05 | 4 | 0.2 | 1.4 | 27.6 | 36.6 | 38.1 | 37.2 |
| 6 | 0.5 | 4 | 0.2 | 2 | 87.2 | 91.1 | 91.5 | 88.4 |
| 7 | 0.5 | 4 | 0.05 | 1.4 | 68.8 | 72.7 | 72.5 | 69.9 |
| 8 | 0.275 | 3 | 0.125 | 1.7 | 78.3 | 79.0 | 79.7 | 81.4 |
| 9 | 0.05 | 2 | 0.05 | 1.4 | 25.7 | 42.4 | 34.3 | 56.5 |
| 10 | 0.5 | 2 | 0.2 | 1.4 | 64.7 | 69.9 | 49.8 | 66.8 |

Example 2b

Using tert-butyl (R)-(7-hydroxy-5,6,7,8-tetrahydronaphthalen-1-yl)carbamate (Formula (A-7)) (0.5 g) obtained from (R)-8-amino-1,2,3,4-tetrahydronaphthalen-2-ol in the same manner as in the methods of (Examples 1a to 1d), an oxidation reaction was performed under conditions of reagents shown in the following table, at a reaction temperature (0° C. to 5° C.) to obtain the title compound (IPC purity using HPLC).

TABLE 9

| No. | Reagent | | | | Solvent Water: 15 times its volume Solvent: 10 times its volume | | IPC purity A6 (%) | | |
|---|---|---|---|---|---|---|---|---|---|
| | TEMPO (eq) | NaHCO₃ (eq) | KBr (eq) | 10% NaClO (eq) | | | Reaction time (min) | | |
| | | | | | | | 10 | 30 | 60 |
| 11 | 0.5 | 4 | 0.05 | 2 | Water 7.5 mL | Acetone 5 mL | 0 | 0 | 0.8 |
| 12 | 0.5 | 4 | 0.05 | 2 | Water 7.5 mL | CH₃CN 5 mL | 14.9 | 13.6 | 10.6 |

Example 2c

A solution of tert-butyl (R)-(7-hydroxy-5,6,7,8-tetrahydronaphthalen-1-yl)carbamate (Formula (A-7)) (10 g) which was obtained in the same manner as in the methods of (Examples 1a to 1d) in dichloromethane (250 mL, 25 times its volume)-water (150 mL, 15 times its volume) was cooled to −2° C. to 2° C., and TEMPO (0.5 eq), KBr (0.2 eq), NaHCO₃ (4.0 eq), and NaClO ((8.1%), 1.4 eq.) were added to the solution at the same temperature. When an IPC purity was immediately confirmed thereafter, it was confirmed that the reaction was completed with a purity of 95.5%. The reaction solution was worked up, and thereby the title compound was obtained (¹H-NMR yield 77.1%).

Example 2d

TEMPO oxidation was performed in flow mode using a continuous stirred tank reactor (CSTR) shown in FIG. 1. A solution (500 mL) of tert-butyl-(7-hydroxy-5,6,7,8-tetrahydronaphthalen-1-yl)carbamate (Formula (A-5)) (25 g) obtained in the same manner as in the methods of (Examples 1a to 1d) and TEMPO (0.5 eq) in dichloromethane was added into a vessel M1, and KBr (0.05 eq), sodium hydrogen carbonate (4 eq), and water (375 mL) were added into a vessel M2, and 5.0 wt % NaClO (1.3 eq) was added into a vessel M3. While flowing nitrogen gas from the respective nitrogen inlets L1, L2, L3, and L4, the reagents were flowed from the respective vessels M1, M2, and M3 at each flow rate of 13.67 mL/min, 9.83 mL/min, and 4.27 mL/min using the respective pumps P1, P2, and P3, then were passed through the respective pre-cooling tubes T1, T2, and T3 (temperature 0° C. to 5° C., tube length: 2 m, tube diameter: 1/16 SS), then were sequentially passed through the reactor R1, the reactor R2, and the reactor R3 (where each of the reactors 1, 2, and 3 had a capacity of 25 mL, and the respective reactors were cooled to 0° C. to 5° C.), and thereby were poured into a recovery drum CD (where a reaction time in each of the reactors was 0.9 minutes). A target product was obtained with an IPC purity of 96.5% of the reaction solution obtained from the recovery drum CD.

Example 2e

TEMPO oxidation was performed in flow mode using a continuous stirred tank reactor (CSTR) shown in FIG. 1. Tert-butyl (R)-(7-hydroxy-5,6,7,8-tetrahydronaphthalen-1-yl)carbamate (Formula (A-5)) (35 g) obtained in the same manner as in the methods of (Examples 1a to 1d), TEMPO (0.5 eq), and dichloromethane (700 mL) were added into a vessel M1, and KBr (0.05 eq), sodium hydrogen carbonate (4 eq), and water (525 mL) were added into a vessel M2, and 5.0 wt % NaClO (1.3 eq) was added into a vessel M3. While flowing nitrogen gas from the respective nitrogen inlets L1, L2, L3, and L4, the reagents were flowed from the respective vessels M1, M2, and M3 at each flow rate of 13.67 mL/min, 9.83 mL/min, and 4.27 mL/min using the respective pumps P1, P2, and P3, then were passed through the respective pre-cooling tubes T1, T2, and T3 (temperature 0° C. to 5° C., tube length: 2 m, tube diameter: 1/16 SS), then were sequentially passed through the reactor R1, the reactor R2, and the reactor R3 (where each of the reactors 1, 2, and 3 had a capacity of 25 mL, and the respective reactors were cooled to 0° C. to 5° C.), and thereby were poured into a recovery drum CD (where a reaction time in each of the reactors was 0.9 minutes, and it required 47 minutes to complete the flow). An IPC purity of the reaction solution (850 g) obtained from the recovery drum CD was 95.0%. An aqueous Na₂S₂O₄ solution (Na₂S₂O₄: 10 g, water: 250 mL) was added to the reaction solution, and the mixed solution was stirred for 30 minutes. After separating the organic layer and the aqueous layer, the organic layer was washed with water (300 mL×2 times). After concentrating the organic layer under reduced pressure to a volume of 1.5 to 2.5 v, n-heptane (30 to 50 mL) was added thereto and the mixture was stirred at room temperature for 1 hour, and n-heptane (200 mL) was added thereto and the mixture was stirred at room temperature for 16 hours. The resulting solid was collected by filtration and washed with n-heptane (70 mL), and thereby the title compound (25.2 g) was obtained as an off-white solid.

Example 2f

TEMPO oxidation was performed in flow mode using a continuous stirred tank reactor (CSTR) shown in FIG. 1. Tert-butyl-(7-hydroxy-5,6,7,8-tetrahydronaphthalen-1-yl)carbamate (Formula (A-5)) (276.6 g) obtained in the same manner as in the methods of (Examples 1a to 1d), TEMPO (82.588 g, 0.5 eq), and dichloromethane (5,535 mL, 20 v) were added into a vessel M1, and KBr (6.251 g), sodium hydrogen carbonate (352.943 g), and water (4,149 mL) were added into a vessel M2, and 5.0 wt % NaClO (1.849 L) was added into a vessel M3. While flowing nitrogen gas from the respective nitrogen inlets L1, L2, L3, and L4, the reagents were flowed from M1, M2, and M3 at each flow rate of 13.67 mL/min, 9.83 mL/min, and 4.27 mL/min using the respective pumps P1, P2, and P3, then were passed through the respective pre-cooling tubes T1, T2, and T3 (temperature 0° C. to 5° C., tube length: 2 m, tube diameter: 1/16 SS), then were sequentially passed through the reactor R1, the reactor R2, and the reactor R3 (where each of the reactors 1, 2, and 3 had a capacity of 25 mL, and the respective reactors were cooled to 0° C. to 5° C.), and thereby were poured into a recovery drum CD (where a reaction time in each of the reactors in flow mode was 0.9 minutes, and it required 410 minutes to complete the flow). A 3.7% $Na_2S_2O_4$ solution (2,597 g) was added to 6,845 g of the obtained reaction mixed solution, and the mixed solution was stirred for 30 minutes. After separating the organic layer and the aqueous layer, the organic layer was washed with water (3 L×2 times). After concentrating the organic layer under reduced pressure to a volume of 2.5 v, n-heptane (205 mL) and one fragment of the already obtained compound represented by Formula A-6 were added thereto and the mixture was stirred at room temperature for 1 hour. Furthermore, n-heptane (2.1 L) was added thereto, and the resulting solid was collected by filtration, washed with n-heptane (800 mL), and dried under reduced pressure for 13 hours to obtain the title compound (190 g) as a brown solid.

[Data of Physical Properties of Compound Represented by Formula (A-6)]

($^1$H NMR, 400 MHz, manufacturer: Bruker, $CDCl_3$, δ ppm)

7.42 (d, 1H, J=7 Hz), 7.14 (t, 1H, J=7 Hz), 6.97 (d, 1H, J=7 Hz), 6.12 (s, 1H), 3.41 (s, 2H), 3.01 (t, 2H, J=6 Hz), 2.51 (dd, 2H, J=6 Hz, 7 Hz), 1.44 (s, 9H)

(Examples 3a to 3g) Synthesis of tert-butyl (R)-(7-hydroxy-5,6,7,8-tetrahydronaphthalen-1-yl)carbamate (A-7)

[C98]

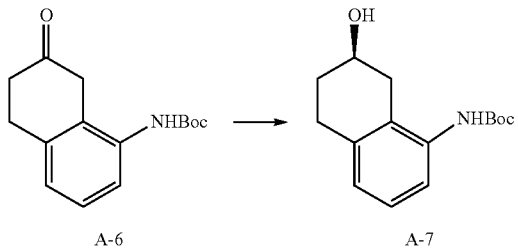

Example 3a

KRED (ketone reductase derived from *Lactobalius* sp., 2.0 g), D-glucose (0.2 g), glucose dehydrogenase (GDH) (0.02 g), nicotinamide adenine dinucleotide phosphate (NADP) (0.01 g), and a phosphate buffer solution (3.0 mL, prepared by adding 21.25 g of $K_2HIPO_4$ and 10.62 g $KH_2PO_4$ to 1,000 mL of water) were mixed into a glass flask (capacity 8 mL) and stirred to prepare a mixed solution A. A mixed solution obtained by dissolving the compound (0.1 g) of Formula (A-6) obtained in the same manner as in the methods of (Examples 2a to 2f) in dimethyl sulfoxide (DMSO) (0.2 mL) was added into the previously prepared mixed solution A. The mixture was stirred at a reaction temperature of 23° C. (20° C. to 25° C.) for 43 hours (at 250 rpm in an orbital shaker). Some parts of the reaction solution were sampled and subjected to HPLC analysis, and it was confirmed that the title compound was obtained.

KRED used in Examples 3a to 3g is a ketone reductase derived from *Lactobacillus* sp. (EnzymeWorks, Inc., product number: EW-KRED-172).

Example 3b

KRED (ketone reductase derived from *Lactobalius* sp., 20 g), D-glucose (2 g), glucose dehydrogenase (GDH) (0.2 g), nicotinamide adenine dinucleotide phosphate (NADP) (0.1 g), and a buffer solution (prepared by adding 0.86 g of $K_2HPO_4$ $3H_2O$ and 0.3 g of $KH_2PO_4$ to 30 mL of water) were mixed into a reactor and stirred to prepare a mixed solution B. A mixed solution obtained by dissolving the compound (1 g) of Formula (A-6) obtained in the same manner as in the methods of (Examples 2a to 2f) in toluene (13 mL) was added into the previously prepared mixed solution B. The mixture was stirred at a reaction temperature of 23° C. (20° C. to 25° C.) for 15 hours. The reaction solution was filtered using a Celite, and the aqueous layer and the organic layer were separated, then the aqueous layer was extracted with toluene (30 mL), and the organic layer was combined with the previously obtained organic layer, and then washed with water (30 mL×2 times), then concentrated to obtain the title compound (0.5 g, optical purity 99.9% ee) as a brown oil.

Example 3c

An investigation of the amount of KRED and a pH were performed under reaction conditions shown in the table below. The compound represented by Formula (A-6) was obtained in the same manner as in the methods of (Examples 2a to 2f). A buffer solution was prepared from $K_2HPO_4$ $3H_2O$ and $KH_2PO_4$ in the same manner as in Example 3b.

TABLE 10

| | | | Conditions | | | | | IPC |
|---|---|---|---|---|---|---|---|---|
| | | | Enzyme | | Solvent | Reaction step | | purity |
| No. | A-6 (g) | pH | (times = times its weight) | D-glucose | (times = times its volume) | Temp. (° C.) | Time (h) | A7 (%) |
| 1 | 0.5 | 6.5-7.0 | KRED 5 times GDH 0.2 times NADP 0.1 times | 2.0 times | Toluene 13 times Buffer solution 30 times | 20 to 25 | 112 | 93.8 |
| 2 | 0.5 | 6.5-7.0 | KRED 10 times GDH 0.2 times NADP 0.1 times | 2.0 times | Toluene 13 times Buffer solution 30 times | 20 to 25 | 112 | 97.3 |
| 3 | 0.5 | 6.0-6.5 | KRED 5 times GDH 0.2 times NADP 0.1 times | 2.0 times | Toluene 13 times Buffer solution 30 times | 20 to 25 | 40 | 83.1 |
| 4 | 0.5 | 6.5-7.0 | KRED 5 times GDH 0.2 times NADP 0.1 times | 2.0 times | Toluene 13 times Buffer solution 30 times | 20 to 25 | 40 | 90.1 |
| 5 | 0.5 | 7.0-7.5 | KRED 5 times GDH 0.2 times NADP 0.1 times | 2.0 times | Toluene 13 times Buffer solution 30 times | 20 to 25 | 40 | 84.5 |

Example 3d

An investigation of the amount of the solvent was performed under reaction conditions shown in the table below. The compound represented by Formula (A-6) was obtained in the same manner as in the methods of (Examples 2a to 2f). A buffer solution was prepared from $K_2HPO_4$ $3H_2O$ and $KH_2PO_4$ in the same manner as in Example 3b.

TABLE 11

| | | | Conditions | | | | | IPC |
|---|---|---|---|---|---|---|---|---|
| | | | Enzyme | | Solvent | Reaction step | | purity |
| No. | A-6 (g) | pH | (times = times its weight) | D-glucose | (times = times its volume) | Temp. (° C.) | Time (h) | A7 (%) |
| 1 | 0.5 | 6.5-7.0 | KRED 10 times GDH 0.2 times NADP 0.1 times | 2.0 times | Toluene 5 times Buffer solution 30 times | 20 to 25 | 18 | 95.6 |
| 2 | 0.5 | 6.5-7.0 | KRED 10 times GDH 0.2 times NADP 0.1 times | 2.0 times | Toluene 10 times Buffer solution 30 times | 20 to 25 | 18 | 93.3 |

Example 3e

An investigation of an amount of the buffer solution, an amount of the raw material, and an amount of KRDE were performed under reaction conditions shown in the table below. The compound represented by Formula (A-6) was obtained in the same manner as in the methods of (Examples 2a to 2f). A buffer solution was prepared from $K_2HPO_4$-$3H_2O$ and $KH_2PO_4$ in the same manner as in Example 3b.

TABLE 12

| | | | Conditions | | | | | IPC |
|---|---|---|---|---|---|---|---|---|
| | | | Enzyme | | Solvent | Reaction step | | purity |
| No. | A-6 (g) | pH | (times = times its weight) | D-glucose | (times = times its volume) | Temp. (° C.) | Time (h) | A7 (%) |
| 1 | 5 | 6.5-7.0 | KRED 10 times GDH 0.2 times NADP 0.1 times | 2.0 times | Toluene 5 times Buffer solution 30 times | 20 to 25 | 4 23 87 | 67.0 95.5 95.3 |

TABLE 12-continued

| No. | A-6 (g) | pH | Enzyme (times = times its weight) | D-glucose | Solvent (times = times its volume) | Reaction step Temp. (° C.) | Time (h) | IPC purity A7 (%) |
|---|---|---|---|---|---|---|---|---|
| 2 | 0.5 | 6.5-7.0 | KRED 5 times GDH 0.2 times NADP 0.1 times | 2.0 times | Toluene 5 times Buffer solution 30 times | 20 to 25 | 16 26 46 72 | 84.7 93.2 95.7 95.9 |
| 3 | 0.5 | 6.5-7.0 | KRED 10 times GDH 0.2 times NADP 0.1 times | 2.0 times | Toluene 5 times Buffer solution 15 times | 20 to 25 | 18 28 48 74 | 89.0 94.2 96.2 95.8 |

Example 3f

An enzymatic reaction was performed for 23 hours with a pH of a reaction solution=6.0 to 7.0 and at a reaction temperature of 23° C. (20° C. to 25° C.), and then for 16 hours at 50° C. to 60° C. using the compound (10 g) of Formula (A-6) obtained in the same manner as in the methods of (Examples 2a to 2f), toluene (50 mL), a buffer solution (300 mL, a composition of K₂HPO₄ 3H₂O and KH₂PO₄ was the same as in the above-described examples), KRED (100 g), D-glucose (20 g), NADP (0.25 g), and GDH (0.5 g), then work up was performed according to the above-mentioned work up method, and thereby the title compound (11.75 g) was obtained as a dark red oil.

Example 3g

KRED (1,279 g), D-glucose (253 g), NADP (12.61 g), and GDH (25.26 g) were added into a buffer solution (3,780 mL) prepared by dissolving K₂HPO₄ 3H₂O (108.4 g) and KH₂PO₄ (37.82 g) in water (3,780 mL) to prepare a mixed solution (MS-6-1), and then the mixed solution was stirred for 1 hour. A mixed solution obtained by dissolving the compound (126.05 g) of Formula (A-6) obtained in the same manner as in the methods of (Examples 2a to 2f) in toluene (630 mL) was added into the previously prepared mixed solution (MS-6-1). The reaction solution was stirred at a reaction temperature of 23° C. (20° C. to 25° C.) for 26 hours while maintaining a pH of the reaction solution at pH=6.0 to 7.0. Tert-amyl alcohol (500 mL) and isoamyl alcohol (130 mL) were added into the reaction solution, and the mixed solution was stirred at a reaction temperature of 23° C. (20° C. to 25° C.) for 16 hours. Ethyl acetate (1,300 mL) and a Celite (126 g) were added thereto, a temperature was raised to 60° C., and the mixture was stirred at the same temperature for 1 hour. After cooling to 20° C., filtration was performed and the aqueous layer and the organic layer were separated, and the aqueous layer was extracted with ethyl acetate (1,300 mL), then the organic layer was combined with the previously obtained organic layer, and then washed with water (1,300 mL) to obtain an organic layer (OP-6-1). Furthermore, ethyl acetate (1,300 mL) was added to the filtered Celite, and the mixture was stirred at 20° C. to 30° C. for 10 hours and filtered to obtain an organic layer (OP-6-2), and once again ethyl acetate (1,300 mL) was added to the filtered Celite, and the mixture was stirred at 20° C. to 30° C. for 2 hours and filtered to obtain an organic layer (OP-6-3). The organic layer (OP-6-1), the organic layer (OP-6-2), and the organic layer (OP-6-3) were combined to form an organic layer (OP-6A). Furthermore, the reaction was performed in the same manner as in the method described above using the compound (113 g) of Formula (A-6) obtained in the same manner as in the methods of (Examples 2a to 2f), and thereby an organic layer (OP-6B) was obtained. The organic layer (OP-6A) and the organic layer (OP-6B) were combined and then concentrated, and thereby the title compound (331 g) was obtained as a reddish brown oil.

[Data of Physical Properties of Compound Represented by Formula (A-7)]

(¹H NMR, 400 MHz, manufacturer: Bruker, CDCl₃, δ ppm)

7.51 (d, 1H, J=7 Hz), 7.05 (t, 1H, J=7 Hz), 6.80 (d, 1H, J=7 Hz), 6.19 (brs, 1H), 4.10-4.05 (1H, m), 2.92-2.81 (2H, m), 2.80-2.69 (1H, m), 2.43 (dd, 1H, J=7 Hz, 16 Hz), 2.03-1.88 (1H, m), 1.78-1.63 (1H, m), 1.45 (9H, s)

An absolute configuration of the compound represented by Formula (A-7) was determined by converting the compound represented by Formula (A-7) to the compound represented by Formula (B), thereafter, comparing an analytical data thereof to that of a compound represented by Formula (B) synthesized separately by a method disclosed in WO 2003/095420, and the like, and confirming whether those analytical data matched. Furthermore, whether hydroxyl groups in the compound represented by Formula (B) had the (R) configuration was determined by converting the compound represented by Formula (B) to a hydrobromide thereof, and analyzing the hydrobromide with an X-ray crystal structure (refer to (Example 5) and FIG. 2).

(Example 4a) Synthesis of hydrochloride of (R)-8-amino-1,2,3,4-tetrahydronaphthalen-2-ol (Formula B-HCl)

[C99]

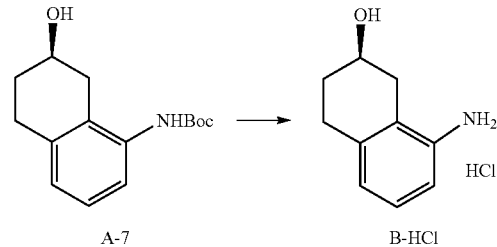

n-PrOH (2 g) was added into a reactor and stirred at −5° C. to 5° C. Acetyl chloride (0.76 g) was added dropwise at the same temperature over 10 minutes. After raising a reaction temperature to 50° C. to 55° C., a solution of the compound (0.5 g) of Formula (A-7) obtained in the same manner as in the methods of (Example 3a to g) in n-PrOH (6 g) was added to the mixture over 45 minutes. After stirring at a reaction temperature of 50° C. to 55° C. for 45 minutes, the mixture was allowed to cool so that the reaction temperature reached between 20° C. and 30° C., and the mixture was stirred at 20° C. to 30° C. for 16 hours. The obtained solid was filtered, washed with n-PrOH (5 mL×2 times), and dried at 40° C. to 50° C. for 6.5 hours to obtain the title compound (0.23 g).

(Example 4b) Synthesis of (R)-8-amino-1,2,3,4-tetrahydronaphthalen-2-ol (Formula B)

[C100]

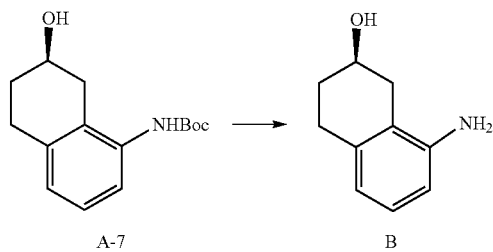

n-PrOH (1.81 g) was added into a reactor and stirred at −5° C. to 5° C. Acetyl chloride (2.35 g) was added dropwise at the same temperature over 10 minutes. After raising a reaction temperature to 33° C. to 37° C., a solution of the compound (4.25 g) of Formula (A-7) obtained in the same manner as in the methods of (Example 3a to g) in n-PrOH (12.75 g) was added to the mixture over 45 minutes. After stirring at a reaction temperature of 33° C. to 37° C. for 49.5 hours, the mixture was stirred at a reaction temperature of 20° C. to 25° C. for 19 hours. The generated solid was filtered, washed with i-PrOAc (10 mL×2 times), and dried at 30° C. to 40° C. for 4 hours to obtain a hydrochloride (2.04 g). After the separately synthesized hydrochloride (0.07 g) were combined to make 2.11 g, the combined product was suspended in ethyl acetate (12 mL), and a pH of the aqueous layer was adjusted to 7 to 8 using an aqueous solution of sodium hydrogen carbonate. After the aqueous layer and the organic layer were separated, the aqueous layer was extracted with ethyl acetate (12 mL×2 times), and the organic layers were combined, washed with water (10 mL×2 times), then concentrated under reduced pressure to obtain the title compound (1.34 g).

(Example 4c) Synthesis of (R)-8-amino-1,2,3,4-tetrahydronaphthalen-2-ol (Formula B)

n-PrOH (138 g) was added into a reactor and stirred at −5° C. to 5° C. Acetyl chloride (180.1 g) was added dropwise at the same temperature over 1 hour. After raising a reaction temperature to 33° C. to 37° C., a solution of a crude compound (331 g) of Formula (A-7) obtained in the same manner as in the methods of (Example 3a to g) in n-PrOH (750 mL) was added to the mixture over 45 minutes. After stirring at a reaction temperature of 33° C. to 37° C. for 15 hours, the mixture was stirred at a reaction temperature of 50° C. to 55° C. for 2 hours and 10 minutes. After a reaction temperature was set to 33° C. to 37° C., a mixed solution obtained by adding HCl (gass) (26 g) to i-PrOAc (192 g) was added to the mixture at 33° C. to 37° C. over 30 minutes. The reaction temperature was raised to 50° C. to 55° C., and the mixture was stirred for 1.5 hours. The produced solid was filtered, washed with i-PrOAc, and dried under reduced pressure at 20° C. to 30° C. for 36 hours to obtain a hydrochloride (158 g). The hydrochloride (158 g) was suspended in ethyl acetate (1,000 mL), and an aqueous solution of sodium hydrogen carbonate (76 g of sodium hydrogen carbonate, 1,000 mL of water) was added thereinto over 30 minutes. After the aqueous layer and the organic layer were separated, the aqueous layer was extracted with ethyl acetate (1,000 mL×2 times), and the organic layers were combined, washed with water (1,000 mL), and concentrated under reduced pressure to obtain the title compound (136 g).

[Data of Physical Properties of Compound Represented by Formula (B)]

($^1$H-NMR, 400 MHz, manufacturer: Bruker, CDCl$_3$, δ ppm)

6.91 (1H, t, J=7 Hz), 6.52-6.46 (2H, m), 4.19-4.04 (2H, m), 3.51 (1H, brs), 2.93-2.65 (3H, m), 2.31 (1H, dd, J=7 Hz, 16 Hz), 2.02-1.89 (1H, m), 1.85-1.65 (1H, m)

(Example 5) Synthesis of (R)-8-amino-1,2,3,4-tetrahydronaphthalen-2-ol hydrobromide (Formula (B-HBr))

[C101]

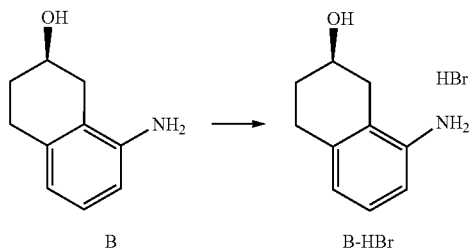

A crude compound (99.9 g) of (R)-8-amino-1,2,3,4-tetrahydronaphthalen-2-ol obtained by the same operation as in (Example 4b) or (Example 4c) was dissolved in ethyl acetate (1 L), and an aqueous solution of 48% hydrobromic acid (80 mL) was added to the mixture under ice-water cooling. The precipitated solid was collected by filtration and washed successively with isopropanol (300 to 400 mL) and ethyl acetate (500 mL). The obtained crude hydrobromide (123.9 g, 98.3% ee) was dissolved in hot water (250 mL), and activated carbon (20 g) was added thereto. The activated carbon was filtered using a Celite when it was hot, and washed with water. The filtrate was concentrated under reduced pressure, and the obtained residue was recrystallized with water. The obtained crystals were collected by filtration, and washed with isopropanol and ethyl acetate to obtain the title compound (34.2 g, 98.4% ee) was obtained. The filtrate was collected, concentrated under reduced pressure, and recrystallized twice with water to obtain the title compound (29.1 g, 98.9% ee).

An optical purity of the hydrobromide of the compound represented by Formula (B) was measured using a HPLC LC-10 system of Shimadzu Corporation under the following conditions.

TABLE 13

| | |
|---|---|
| Column | CHIRALCEL OJ-H ID 4.6 × 250 mm (Daicel) |
| Elution solvent | n-Hexane/Ethanol/Diethylamine = 50/50/0.1 (v/v/v) |
| Flow rate | 0.5 mL/min |
| Column temperature | 20° C. |
| Measurement wavelength | 254 nm |
| Elution time | R form - 11.2 minutes, S form - 12.5 minutes |

Furthermore, an X-ray crystal structure of a single crystal of the obtained hydrobromide of the compound represented by Formula (B) ((R)-8-amino-1,2,3,4-tetrahydronaphthalen-2-ol) was analyzed using AFC-7 of Rigaku, and the following results were obtained (refer to FIG. 2).

TABLE 14

| | |
|---|---|
| Crystal system | Monoclinic |
| Space group | P21 (#4) |
| Unit cell dimensions | a = 7.7320 (19) Å, α = 90.02 (3)°, |
| | b = 8.681 (3) Å, β = 103.47°, |
| | c = 8.017 (2) Å, γ = 90.00 (2)° |
| Volume | 523.3 (3) Å3 |
| Refinement method | Full-matrix least-squares |
| Data/restraints/parameters | 1549/1/121 |
| Goodness-of-fit on F2 | 1.430 |
| Final R indices [I > 2sigma(I)] | R1 = 0.0590, wR2 = 0.1710 |
| R indices (all data) | R1 = 0.1033, wR2 = 0.2584 |
| Absolute structure parameter | −0.06 (5) |
| Largest diff. peak and hole | 0.296 and −0.384 e.Å-3 |

(Example 6) Synthesis of (E)-2-(7-trifluoromethyl-chroman-4-ylidene)-N-[(7R)-7-hydroxy-5,6,7,8-tetrahydronaphthalen-1-yl]acetamide (Formula (I))

[C102]

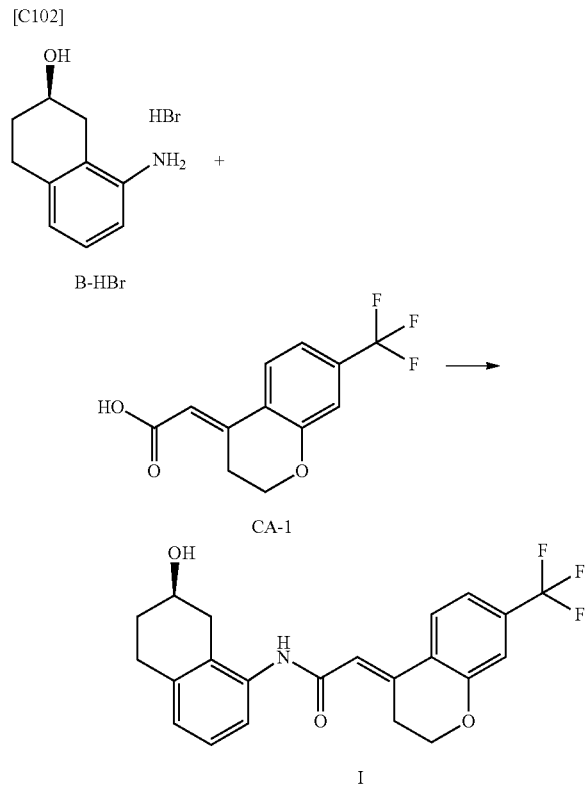

Triethylamine (0.27 mL, 1.0 eq) and 4-(4,6-dimethoxy-1,3,5-triazin-2-yl)-4-methylmorpholinium chloride (DMT-MM) (0.80 g, 1.5 eq) were added to a suspension of (R)-8-amino-1,2,3,4-tetrahydronaphthalen-2-ol hydrobromide (Formula (B-HBr)) (0.47 g) obtained in (Example 5) and (E)-2-(7-(trifluoromethyl)chroman-4-ylidene)acetic acid (Formula (CA-1)) (0.50 g, 1.0 eq) obtained by a production method disclosed in WO 2007/010383 in methanol (5.00 mL: about 10 times its volume with respect to 1 g of the compound represented by Formula (B-HBr)), and the mixture was stirred at room temperature for 3 hours. After the reaction solution was ice-cooled, the precipitated crystals were collected by filtration and washed with cold methanol. The obtained solid was dissolved in ethanol (6 mL) by heating, and then water (6 mL) was added during heating. After cooling the mixture, the precipitated solid was filtered, washed successively with 50% water-ethanol and water, and then dried under reduced pressure to obtain the title compound (0.56 g) as a white solid.

[Data of Physical Properties of Compound Represented by Formula (I)]

($^1$H-NMR data (CDCl$_3$) (δ: ppm)):

7.80-7.58 (m, 1H), 7.24-6.92 (m, 5H), 6.45 (s, 1H), 4.29 (t, 2H, J=6 Hz), 4.28-4.15 (m, 1H), 3.51 (t, 2H, J=5 Hz), 3.10-2.78 (m, 3H), 2.69-2.53 (m, 1H), 2.14-2.00 (m, 1H), 1.90-1.67 (m, 2H)

(LC-MS):

RT=4.73 (minutes), [M+H]$^+$=404

Optical purity: 97.9% ee

An optical purity of the compound represented by Formula (I) was measured using a HPLC LC-VP system of Shimadzu Corporation under the following conditions.

TABLE 15

| | |
|---|---|
| Column | CHIRALCEL AD-H ID 4.6 × 250 mm (Daicel) |
| Elution solvent | Ethanol |
| Flow rate | 0.5 mL/min |
| Column temperature | 40° C. |
| Measurement wavelength | 254 nm |
| Elution time | Compound represented by Formula (I) - 10.5 minutes, |
| | Enantiomer of compound represented by Formula (I) - 18.6 minutes |

The crystal structure of the compound represented by Formula (I) was analyzed at a SPring-8 beamline BL32B2 using an R-AXIS V detector of Rigaku (refer to FIG. 3).

TABLE 16

| | |
|---|---|
| Crystal system | Monoclinic |
| Space group | P21 (#4) |
| Unit cell dimensions | a = 16.344 Å, α = 90°, |
| | b = 7.272 Å, β = 113.80°, |
| | c = 19.088 Å, γ = 90° |
| Volume | 2075.6 Å3 |
| Z | 4 |
| Density (calculated) | 1.291 Mg/m$^3$ |
| Refinement method | Full-matrix least-squares |
| Data/restraints/parameters | 5861/1/581 |
| Goodness-of-fit on F2 | 1.123 |
| Final R indices [I > 2sigma(I)] | R1 = 0.0590, wR2 = 0.1710 |
| R indices (all data) | R1 = 0.0653, wR2 = 0.1795 |
| Largest diff. peak and hole | 0.408 and −0.323 e.Å-3 |

(Example 7) Synthesis of (E)-2-(7-trifluoromethyl-chroman-4-ylidene)-N-[(7R)-7-hydroxy-5,6,7,8-tetrahydronaphthalen-1-yl]acetamide: (Examination (1) of conditions for condensation reaction)

[C103]

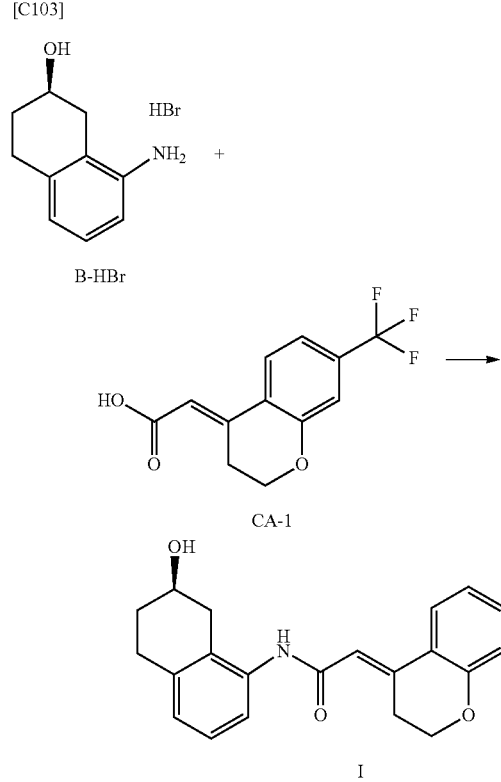

<Examination 1> Triethylamine (120 μL, 1.05 eq) and 4-(4,6-dimethoxy-1,3,5-triazin-2-yl)-4-methylmorpholinium chloride (DMT-MM) (339 mg, 1.5 eq) were added to a suspension of (R)-8-amino-1,2,3,4-tetrahydronaphthalen-2-ol hydrobromide (200 mg) obtained in (Example 5) and (E)-2-(7-(trifluoromethyl)chroman-4-ylidene)acetic acid (212 mg, 1.0 eq) obtained by a production method disclosed in WO 2007/010383 in methanol (3.15 mL: 15.75 times its volume with respect to 1 g of the compound represented by Formula (B-HBr)), and the mixture was stirred at room temperature for 3 hours. Water was added thereto, and the precipitated solid was filtered, washed with water, and dried to obtain the title compound (291 mg) as a white solid.

<Examination 2> Triethylamine (240 μL, 2.1 eq) and 4-(4,6-dimethoxy-1,3,5-triazin-2-yl)-4-methylmorpholinium chloride (DMT-MM) (339 mg, 1.5 eq) were added to a suspension of (R)-8-amino-1,2,3,4-tetrahydronaphthalen-2-ol hydrobromide (200 mg) obtained in (Example 5) and (E)-2-(7-(trifluoromethyl)chroman-4-ylidene)acetic acid (212 mg, 1.0 eq) obtained by a production method disclosed in WO 2007/010383 in methanol (3.15 mL: 15.75 times its volume with respect to 1 g of the compound represented by Formula (B-HBr)), and the mixture was stirred at room temperature for 3 hours. Water was added thereto, and the precipitated solid was filtered, washed with water, and dried to obtain the title compound (273 mg) as a white solid.

<Examination 3> Triethylamine (120 μL, 1.05 eq) and 4-(4,6-dimethoxy-1,3,5-triazin-2-yl)-4-methylmorpholinium chloride (DMT-MM) (339 mg, 1.5 eq) were added to a suspension of (R)-8-amino-1,2,3,4-tetrahydronaphthalen-2-ol hydrobromide (200 mg) obtained in (Example 5) and (E)-2-(7-(trifluoromethyl)chroman-4-ylidene)acetic acid (212 mg, 1.0 eq) obtained by a production method disclosed in WO 2007/010383 in methanol (1.60 mL: 8 times its volume with respect to 1 g of the compound represented by Formula (B-HBr)), and the mixture was stirred at room temperature for 3 hours. Water was added thereto, and the precipitated solid was filtered, washed with water, and dried to obtain the title compound (298 mg) as a white solid.

<Examination 4> Triethylamine (120 μL, 1.05 eq) and 4-(4,6-dimethoxy-1,3,5-triazin-2-yl)-4-methylmorpholinium chloride (DMT-MM) (339 mg, 1.5 eq) were added to a suspension of (R)-8-amino-1,2,3,4-tetrahydronaphthalen-2-ol hydrobromide (200 mg) obtained in (Example 5) and (E)-2-(7-(trifluoromethyl)chroman-4-ylidene)acetic acid (212 mg, 1.0 eq) obtained by a production method disclosed in WO 2007/010383 in methanol (3.15 mL: 15.75 times its volume with respect to 1 g of the compound represented by Formula (B-HBr)), and the mixture was stirred under heating reflux for 3 hours. After cooling the mixture, water was added thereto, and the precipitated solid was filtered, washed with water, and dried to obtain the title compound (291 mg) as a white solid.

In <Examination 1> to <Examination 4> of (Example 7) described above, generating of the endo product of the compound represented by Formula (I) ((R)—N-(7-hydroxy-5,6,7,8-tetrahydronaphthalen-1-yl)-2-(7-(trifluoromethyl)-2H-chromen-4-yl)acetamide) was suppressed.

A chemical purity of the compound represented by Formula (I) was measured using a HPLC LC-VP system of Shimadzu Corporation under the following conditions.

TABLE 17

| | |
|---|---|
| Column | Develosil ODS-HG-5 ID 4.6 × 150 mm (NOMURA CHEMICAL CO., LTD.) |
| Elution solvent | Acetonitrile/water = 50/50 (v/v) |
| Flow rate | 1.0 mL/min |
| Column temperature | 40° C. |
| Measurement wavelength | 273 nm |
| Elution time | Endo product of compound represented by Formula (I) - 5.9 minutes, Compound represented by Formula (I) - 9.1 minutes |

(Example 8) Synthesis of (E)-2-(7-trifluoromethyl-chroman-4-ylidene)-N-[(7R)-7-hydroxy-5,6,7,8-tetrahydronaphthalen-1-yl]acetamide: (Examination (2) of conditions for condensation reaction)

[C104]

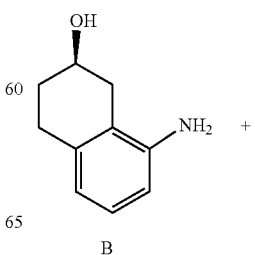

B

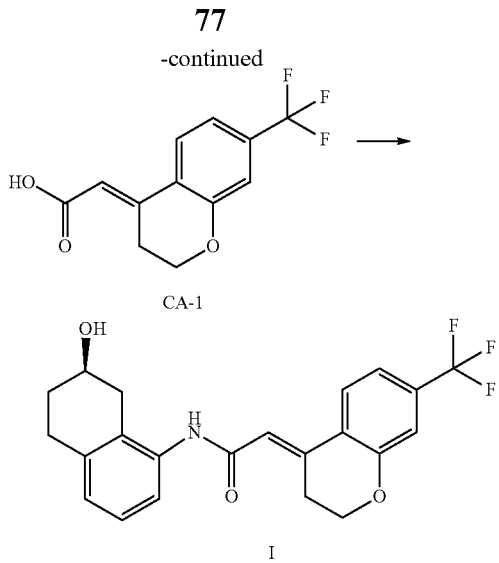

<Examination 1> 4-(4,6-dimethoxy-1,3,5-triazin-2-yl)-4-methylmorpholinium chloride (DMT-MM) (257 mg, 1.5 eq) was added to a suspension of (R)-8-amino-1,2,3,4-tetrahydronaphthalen-2-ol (101 mg) obtained in the same operation as that in (Example 4b) or (Example 4c) and (E)-2-(7-(trifluoromethyl)chroman-4-ylidene)acetic acid (200 mg, 1.25 eq) obtained by a production method disclosed in WO 2007/010383 in isopropanol (3.0 mL: about 30 times its volume with respect to 1 g of the compound represented by Formula (B)), and the mixture was stirred at room temperature for 6 hours. Water (3 mL) was added thereto, and the precipitated solid was filtered, washed with water, and dried to obtain the title compound (209 mg) as a white solid.

<Examination 2> 4-(4,6-dimethoxy-1,3,5-triazin-2-yl)-4-methylmorpholinium chloride (DMT-MM) (257 mg, 1.5 eq) was added to a suspension of (R)-8-amino-1,2,3,4-tetrahydronaphthalen-2-ol (126 mg) obtained in the same operation as that in (Example 4b) or (Example 4c) and (E)-2-(7-(trifluoromethyl)chroman-4-ylidene)acetic acid (200 mg, 1.0 eq) obtained by a production method disclosed in WO 2007/010383 in isopropanol (3.00 mL: about 24 times its volume with respect to 1 g of the Formula (B)), and the mixture was stirred at room temperature for 6 hours. Water (3 mL) was added thereto, and the precipitated solid was filtered, washed with water, and dried to obtain the title compound (238 mg) as a white solid.

<Examination 3> 4-(4,6-dimethoxy-1,3,5-triazin-2-yl)-4-methylmorpholinium chloride (DMT-MM) (257 mg, 1.5 eq) was added to a suspension of (R)-8-amino-1,2,3,4-tetrahydronaphthalen-2-ol (152 mg) obtained in the same operation as that in (Example 4b) or (Example 4c) and (E)-2-(7-(trifluoromethyl)chroman-4-ylidene)acetic acid (200 mg, 0.83 eq) obtained by a production method disclosed in WO 2007/010383 in isopropanol (3.00 mL: about 20 times its volume with respect to 1 g of the compound represented by Formula (B)), and the mixture was stirred at room temperature for 6 hours. Water (3 mL) was added thereto, and the precipitated solid was filtered, washed with water, and dried to obtain the title compound (243 mg) as a white solid.

<Examination 4> 4-(4,6-dimethoxy-1,3,5-triazin-2-yl)-4-methylmorpholinium chloride (DMT-MM) (257 mg, 1.5 eq) was added to a suspension of (R)-8-amino-1,2,3,4-tetrahydronaphthalen-2-ol (177 mg) obtained in the same operation as that in (Example 4b) or (Example 4c) and (E)-2-(7-(trifluoromethyl)chroman-4-ylidene)acetic acid (200 mg, 0.71 eq) obtained by a production method disclosed in WO 2007/010383 in isopropanol (3.00 mL: about 20 times its volume with respect to 1 g of the compound represented by Formula (B)), and the mixture was stirred at room temperature for 6 hours. Water (3 mL) was added thereto, and the precipitated solid was filtered, washed with water, and dried to obtain the title compound (238 mg) as a white solid.

(Example 9a) Synthesis of (E)-2-(7-trifluoromethyl-chroman-4-ylidene)-N-[(7R)-7-hydroxy-5,6,7,8-tetrahydronaphthalen-1-yl]acetamide After a condensation reaction (reaction conditions: 20° C. to 25° C., stirring for 22 hours) was performed using (R)-8-amino-1,2,3,4-tetrahydronaphthalen-2-ol (1.04 g, purity 99.35%) obtained in the same operation as that in (Example 4b) or (Example 4c), (E)-2-(7-(trifluoromethyl)chroman-4-ylidene)acetic acid (1.05 eq) obtained by a production method disclosed in WO 2007/010383, isopropanol (25 times its volume with respect to the compound represented by Formula (B)), and 4-(4,6-dimethoxy-1,3,5-triazin-2-yl)-4-methylmorpholinium chloride (DMT-MM) (1.3 eq), a work up was performed according to (Example 8), and thereby the title compound (1.87 g) was obtained as a solid.

(Example 9b) Synthesis of (E)-2-(7-trifluoromethyl-chroman-4-ylidene)-N-[(7R)-7-hydroxy-5,6,7,8-tetrahydronaphthalen-1-yl]acetamide (scale-up)

After a condensation reaction (reaction conditions: 20° C. to 25° C., stirring for 22 hours) was performed using (R)-8-amino-1,2,3,4-tetrahydronaphthalen-2-ol (110 g) obtained in the same operation as that in (Example 4b) or (Example 4c), (E)-2-(7-(trifluoromethyl)chroman-4-ylidene)acetic acid (173.9 g, 1.05 eq) obtained by a production method disclosed in WO 2007/010383, isopropanol (2,600 mL: 25 times its volume with respect to the compound represented by Formula (B)), and 4-(4,6-dimethoxy-1,3,5-triazin-2-yl)-4-methylmorpholinium chloride (DMT-MM) (243.7 g, 1.3 eq), a work up was performed according to (Example 8), and thereby the title compound (183.3 g) was obtained as a grayish-white solid.

An optical purity of the compound represented by Formula (I) was measured using a HPLC LC-VP system of Shimadzu Corporation under the following conditions.

TABLE 18

| | |
|---|---|
| Column | CHIRALCEL AD-H ID 4.6 × 250 mm (Daicel) |
| Elution solvent | Ethanol |
| Flow rate | 0.5 mL/min |
| Column temperature | 40° C. |
| Measurement wavelength | 254 nm |
| Elution time | Compound represented by Formula (I) - 10.5 minutes, Enantiomer of compound represented by Formula (I) - 18.6 minutes |

Bruker AV 400 was used for measurement of nuclear magnetic resonance (NMR) spectra of the compounds represented by Formula (A8-BR) and Formula (B).

The high-performance liquid chromatography (HPLC) of compounds represented by Formula (A8-BR) and Formula (B) were measured by the following method.

TABLE 19

Measurement conditions for compound represented by Formula (A8-BR)

| | |
|---|---|
| Measuring instrument | Thermo U-3000 with UV detector or equivalent |
| Column | Waters Xbridge C18 (4.6 mm × 150 mm, 3.5 μm) |
| Measurement wavelength | 220 nm |
| Column temperature | 35° C. |
| Flow rate | 1.0 mL/min |
| Injection capacity | 5 μL |
| Sample concentration | 0.5 mg/mL |
| Performance time | 21 min |
| Data collection time | 21 min |
| Dilution agent | ACN:H$_2$O = 50:50 (v/v) |
| Mobile phase A | 10 mM NH$_4$Ac in H$_2$0 |
| Mobile phase B | ACN |
| Gradient program | |

| Time (min) | Mobile phase A (%) | Mobile phase B (%) |
|---|---|---|
| Initial time | 90 | 10 |
| 13.00 | 15 | 85 |
| 15.00 | 15 | 85 |
| 16.00 | 90 | 10 |
| 21.00 | 90 | 10 |

Rebalancing time: 21 minutes

TABLE 20

Retention time (RT)

| Compound | RT (min) | Relative retention time (RRT) |
|---|---|---|
| Formula (SM8-BR) | 10.6 | 1.1 |
| Formula (A8-BR) | 9.7 | 1.0 |

TABLE 21

Measurement conditions for compound represented by Formula (B)

| | |
|---|---|
| Measuring instrument | Thermo U-3000 with UV detector or equivalent |
| Column | ACE 3 C18 (150 mm × 4.6 mm, 3 μm) |
| Measurement wavelength | 213 nm |
| Column temperature | 35° C. |
| Flow rate | 1.0 mL/min |
| Injection capacity | 5 μL |
| Sample concentration | 0.12 mg/mL |
| Performance time | 16 min |
| Data collection time | 16 min |
| Dilution agent | MeOH |
| Mobile phase A | 5 mM NH$_4$Ac in H2O |
| Mobile phase B | ACN |
| Gradient program | |

| Time (min) | Mobile phase A (%) | Mobile phase B (%) |
|---|---|---|
| Initial time | 95 | 5 |
| 4.00 | 70 | 30 |
| 10.0 | 10 | 90 |
| 11.0 | 10 | 90 |
| 12.0 | 95 | 5 |
| 16.0 | stop | stop |

Rebalancing time: 16 minutes

TABLE 22

Retention time (RT)

| Compound | RT (min) | Relative retention time (RRT) |
|---|---|---|
| Formula (B) | 6.9 | 1.0 |
| Formula (A8-BR) | 9.7 | 1.4 |

TABLE 23

Chiral analysis method for compound represented by Formula (A8-BR)

| | |
|---|---|
| Measuring instrument | Shimadzu LC-20A HPLC with PDA detector or equivalent |
| Column | Daicel Chiralpak IB (250 mm × 4.6 mm, 5 μm) |
| Measurement wavelength | 273 nm |
| Column temperature | 35° C. |
| Flow rate | 1.0 mL/min |
| Injection capacity | 5 μL |
| Sample concentration | 0.6 mg/mL |
| Data collection time | 15 min |
| Performance time | 15 min |
| Dilution agent | EtOH |
| Mobile phase | Hexanes:0.1% ethanolamine in EtOH = 95:5 (v/v) |
| Isocratic program | |

| Time (min) | Mobile phase (%) |
|---|---|
| 0.0 | 100 |
| 15.0 | stop |

TABLE 24

Retention time (RT)

| Compound | RT (min) | Relative retention time (RRT) |
|---|---|---|
| Formula (A8-BR) | 7.9 | 1.00 |
| Enantiomer of Formula (A8-BR) | 7.0 | 0.89 |

TABLE 25

Chiral analysis method for compound represented by Formula (B)

| | |
|---|---|
| Measuring instrument | Agilent 1260 HPLC with UV detector or equivalent |
| Column | Daicel Chiralcel OJ-H (250 × 4.6 mm, 5.0 μm) |
| Measurement wavelength | 237 nm |
| Column temperature | 25° C. |
| Flow rate | 0.5 mL/min |
| Injection capacity | 5 μL |
| Sample concentration | 0.6 mg/mL |
| Data collection time | 11.0 min |
| Performance time | 25 min |
| Dilution agent | EtOH |
| Mobile phase | n-Hexane:Ethanol:DEA (50:50:0.1, v/v/v) |
| Isocratic program | |

| Time (min) | Mobile phase (%) |
|---|---|
| 0.00 | 100% |
| 25.00 | stop |

TABLE 26

Retention time (RT)

| Compound | RT (min) | Relative retention time (RRT) |
|---|---|---|
| Formula (B) | 11.0 | 1.00 |
| Enantiomer of Formula (B) | 12.1 | 1.10 |

(Example 10A) to (Example 10D) Synthesis of (R)-8-bromo-1,2,3,4-tetrahydronaphthalen-2-ol (A8-BR)

[C105]

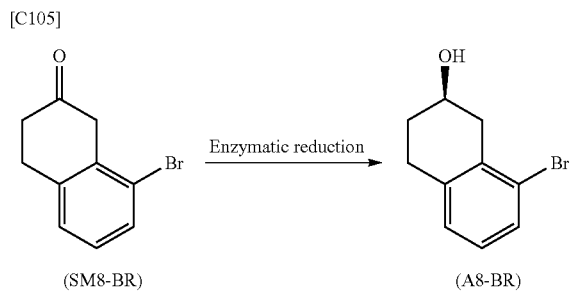

(SM8-BR) → Enzymatic reduction → (A8-BR)

Example 10A

KRED (ketone reductase derived from *Escherichia coli* sp., 5 mg), D-glucose (200 mg), glucose dehydrogenase (GDH) (2 mg), nicotinamide adenine dinucleotide phosphate (NADP) (1 mg), and a phosphate buffer solution (3 mL, prepared by adding 10.62 g of $KH_2PO_4$ and 21.25 g of $K_2HIPO_4$ to 1,000 mL of water) were mixed into a flask equipped with an orbital shaker (manufactured by Shanghai Nanrong Laboratory Equipment Co., Ltd., model number: NRY-200) and stirred to prepare a mixed solution. Next, a mixed solution obtained by dissolving 8-bromo-3,4-dihydronaphthalen-2(1H)-one (Formula (SM8-BR)) (100 mg) in dimethyl sulfoxide (DMSO) (0.3 mL) was added into the previously prepared mixed solution, and the mixture was stirred at a reaction temperature of 30° C. for 20 hours (where a rotation speed of an orbital shaker was 250 rpm). Some parts of the reaction solution were sampled and subjected to HPLC analysis, and it was confirmed that the title compound was obtained with an IPC yield (IPC=in process control) of 97.8% and an optical purity of 99.7%.

Example 10B

KRED (ketone reductase derived from *Escherichia coli* sp., 0.25 g), D-glucose (10 g), glucose dehydrogenase (GDH) (0.1 g), nicotinamide adenine dinucleotide phosphate (NADP) (0.05 g), and a buffer solution (1.55 g of $KH_2PO_4$ and 4.06 g of $K_2HPO_4$ $3H_2O$ were added to 145 mL of water) were mixed into a reactor to prepare a mixed solution, and it was stirred at 20° C. to 25° C. Next, a mixed solution obtained by dissolving 8-bromo-3,4-dihydronaphthalen-2(1H)-one (Formula (SM8-BR)) (5 g) in dimethyl sulfoxide (DMSO) (15 mL) was added dropwise into the previously prepared mixed solution. After stirring at a reaction temperature of 20° C. to 25° C. for 1 hour, a pH of the reaction solution was adjusted to be within a range of pH=6.5 to 7.0 using an aqueous solution of 2M sodium carbonate. Next, after stirring at a reaction temperature of 20° C. to 25° C. for 1 hour, a pH of the reaction solution was adjusted to be within a range of pH=6.5 to 7.0 using an aqueous solution of 2M sodium carbonate. Furthermore, after stirring at a reaction temperature of 20° C. to 25° C. for 1 hour, a pH of the reaction solution was adjusted to be within a range of pH=6.5 to 7.0 using an aqueous solution of 2M sodium carbonate. Thereafter, the reaction solution was stirred at a reaction temperature of 20° C. to 25° C. for 16 hours (some parts of the reaction solution were sampled and subjected to HPLC analysis, and it was confirmed that an IPC yield of the title compound was 99.6%).

Methyl tert-butyl ether (MTBE) (50 mL) was added into the reaction solution, and diatomite (diatomaceous earth) (5 g) containing water (5 g) was further added thereinto, then the mixed solution was stirred at a temperature of 50° C. to 60° C. for 30 minutes. The temperature of the mixed solution was cooled to 20° C. to 25° C., and the mixed solution was further stirred at the same temperature for 1 hour. The mixed solution described above was filtered, and the filtered material (wet cake) was washed with MTBE (5 mL) to obtain a filtrate A. The wet cake described above was put in a reactor, and MTBE (40 mL) was added thereinto, then the mixture was stirred at 20° C. to 25° C. for 2 hours. The suspension containing the wet cake was filtered, and the wet cake was washed with MTBE (5 mL) to obtain a filtrate B. After mixing the filtrate A and the filtrate B and stirring the mixture at 20° C. to 30° C. for 5 minutes, the aqueous layer and the organic layer were separated, and the aqueous layer was extracted with MTBE (45 mL), then the organic layer was combined with the previously obtained organic layer, washed with water (30 mL), and concentrated to obtain a crude title compound (4.61 g). The obtained crude title compound was subjected to silica gel column chromatography (n-heptane:ethyl acetate=1:1) to obtain the title compound (4.15 g, optical purity 99.9%).

Example 10C

KRED (ketone reductase derived from *Escherichia coli* sp., 0.83 g), D-glucose (33.28 g), glucose dehydrogenase (GDH) (0.33 g), nicotinamide adenine dinucleotide phosphate (NADP) (0.17 g), and a buffer solution (5.31 g of $KH_2PO_4$ and 13.89 g of $K_2HPO_4$ $3H_2O$ were added to 499 mL of water) were mixed into a reactor to prepare a mixed solution, and it was stirred at 20° C. to 25° C. Next, a mixed solution obtained by dissolving 8-bromo-3,4-dihydronaphthalen-2(1H)-one (Formula (SM8-BR)) (17.3 g) in dimethyl sulfoxide (DMSO) (50 mL) was added dropwise into the previously prepared mixed solution. After stirring at a reaction temperature of 20° C. to 25° C. for 1 hour, a pH of the reaction solution was adjusted to be within a range of pH=6.5 to 7.0 using an aqueous solution of 2M sodium carbonate. Next, after stirring at a reaction temperature of 20° C. to 25° C. for 1 hour, a pH of the reaction solution was adjusted to be within a range of pH=6.5 to 7.0 using an aqueous solution of 2M sodium carbonate. Furthermore, after stirring at a reaction temperature of 20° C. to 25° C. for 1 hour, a pH of the reaction solution was adjusted to be within a range of pH=6.5 to 7.0 using an aqueous solution of 2M sodium carbonate. Thereafter, the mixture was stirred at a reaction temperature of 20° C. to 25° C. for 16 hours. Some parts of the reaction solution were sampled and subjected to HPLC analysis, and it was confirmed that an IPC yield of the title compound was 97.4%. The same work up as in (Example 1B) was performed to obtain the title compound (17.12 g, optical purity 99.9%).

Example 10D

KRED (ketone reductase derived from *Escherichia coli* sp., 5.55 g), D-glucose (220 g), glucose dehydrogenase (GDH) (2.20 g), nicotinamide adenine dinucleotide phosphate (NADP) (1.12 g), and a buffer solution (35.12 g of $KH_2PO_4$ and 91.80 g of $K_2HPO_4$ $3H_2O$ were added to 3,300 mL of water) were mixed into a reactor to prepare a mixed solution, and it was stirred at 20° C. to 25° C. Next, a mixed solution obtained by dissolving 8-bromo-3,4-dihydronaphthalen-2(1H)-one (Formula (SM8-BR)) (110.31 g) in dimethyl sulfoxide (DMSO) (330 mL) was added dropwise into the previously prepared mixed solution. After stirring at a reaction temperature of 20° C. to 25° C. for 1 hour, a pH of the reaction solution was adjusted to be within a range of pH=6.5 to 7.0 using an aqueous solution of 2M sodium carbonate. Next, after stirring at a reaction temperature of 20° C. to 25° C. for 1 hour, a pH of the reaction solution was adjusted to be within a range of pH=6.5 to 7.0 using an aqueous solution of 2M sodium carbonate. Furthermore, after stirring at a reaction temperature of 20° C. to 25° C. for 2 hours, a pH of the reaction solution was adjusted to be within a range of pH=6.5 to 7.0 using an aqueous solution of 2M sodium carbonate. Thereafter, the mixture was stirred at a reaction temperature of 20° C. to 25° C. for 16 hours. Some parts of the reaction solution were sampled and subjected to HPLC analysis, and it was confirmed that an IPC yield of the title compound was 97.4%.

MTBE (1,100 mL) was added into the reaction solution, and diatomite (diatomaceous earth) (110 g) containing water (110 g) was further added thereinto, and the mixed solution was stirred at a temperature of 50° C. to 60° C. for 30 minutes. The temperature of the mixed solution was cooled to 20° C. to 25° C., and the mixed solution was further stirred at the same temperature for 2 hours. The mixed solution described above was filtered, and the filtered material (wet cake) was washed with MTBE (110 mL) to obtain a filtrate C. The wet cake described above was put in a reactor, and MTBE (900 mL) was added thereinto, then the mixture was stirred at 20° C. to 25° C. for 12 hours. The suspension containing the wet cake was filtered, and the wet cake was washed with MTBE (110 mL) to obtain a filtrate D. The filtrate C and the filtrate D were mixed, and the aqueous layer and the organic layer were separated and the aqueous layer was extracted with MTBE (1,000 mL), then the organic layer was combined with the previously obtained organic layer, washed with water (675 mL), and concentrated to obtain a crude title compound (108.03 g, optical purity 99.8%).

[Data of Physical Properties of Formula (A8)]

($^1$H NMR, 400 MHz, manufacturer: Bruker, DMSO-d$_6$, δ ppm) 7.40 (d, 1H, J=8 Hz), 7.10 (d, 1H, J=8 Hz), 7.04 (t, 1H, J=8 Hz), 4.89 (d, 1H, J=4 Hz), 3.99-3.95 (m, 1H), 2.92-2.86 (m, 2H), 2.70-2.60 (m, 1H), 1.83-1.75 (m, 1H), 1.65-1.55 (m, 1H))

The KRED (ketone reductase derived from *Escherichia coli* sp.) used in (Example 10A) to (Example 10D) is an enzyme manufactured by EnzymeWorks, Inc. (product number: HQ-K-105).

An absolute configuration of the compound represented by Formula (A8-BR) obtained in (Example 10A) to (Example 10D) was determined by converting the Formula (A8-BR) to the Formula (B), and thereafter, confirming whether an analytical data thereof matched an analytical data of a compound represented by Formula (B) synthesized separately by a method disclosed in WO 2003/095420, and the like.

(Reference Example 1) Synthesis of 8-bromo-1,2,3,4-tetrahydronaphthalen-2-ol (Formula (A8-BR-Rac))

[C106]

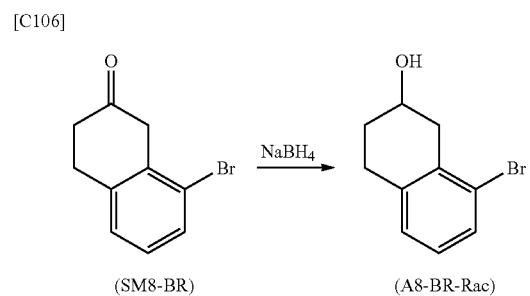

(SM8-BR)  (A8-BR-Rac)

8-Bromo-3,4-dihydronaphthalen-2(1H)-one (Formula (SM8-BR)) (20.0 g) and methanol (200 mL) were added into a reactor, and NaBH$_4$ (8.28 g) was added at an internal temperature of 0° C. to 5° C., and the mixture was stirred at the same temperature for 1 hour (some parts of the reaction solution were sampled and subjected to HPLC analysis, and it was confirmed that an IPC yield was 98.5%). An aqueous solution of 10% sodium hydrogen carbonate (1.5 L) was added dropwise when a temperature of the reaction solution was 5° C. or lower, and the mixed solution was stirred for 0.2 hours at a temperature of the mixed solution of 0° C. to 5° C. Ethyl acetate (1.5 L) was added, and the aqueous layer and the organic layer were separated then the aqueous layer was extracted with ethyl acetate (1.5 L), and the organic layer was combined with the previously obtained organic layer, washed with an aqueous solution of 25 wt % sodium chloride (1.5 L) and concentrated to obtain a crude title compound (21.53 g). The obtained crude title compound was subjected to silica gel column chromatography (n-heptane:ethyl acetate=1:1) to obtain the title compound (21.29 g). It was confirmed that the obtained compound represented by Formula (A8-BR-Rac) matched physical properties data known from a literature.

(Example 11A) to (Example 11G) Synthesis of (R)-8-amino-1,2,3,4-tetrahydronaphthalen-2-ol (Formula (B))

[C107]

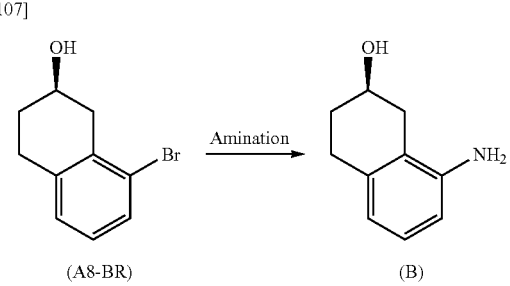

(A8-BR)  (B)

Example 11A (R)-8-bromo-1,2,3,4-tetrahydronaphthalen-2-ol (Formula (A8-BR)) (100 mg) obtained by an enzymatic reduction in the same manner as in the methods of Example 10A to Example 10D, $Cu_2O$ (40 mg), N-methyl-pyrrolidone (NMP) (2 mL), and ammonia water (3 mL) were mixed in a sealed-tube reactor, and a sealed-tube reaction was performed at a temperature of 105° C. to 115° C. for 20 hours. After diluting the mixture with water, the mixture was extracted with ethyl acetate, and the organic layer was washed with an aqueous solution of 25 wt % sodium chloride, dried with $Na_2SO_4$, filtered, and concentrated to obtain a crude title compound (106 mg). Thin layer chromatography (n-heptane:ethyl acetate=1:1) was performed for separation, and thereby the title compound (10 mg) was obtained (optical purity 96.8%).

Example 11B (R)-8-bromo-1,2,3,4-tetrahydronaphthalen-2-ol (Formula (A8-BR)) (2.2 g) obtained by an enzymatic reduction in the same manner as in the methods of Example 10A to Example 10D, $Cu_2O$ (700 mg), NMP (3.5 mL, 1.6 v), and ammonia water (5.5 mL) were mixed in a sealed-tube reactor, and a sealed-tube reaction was performed at a temperature of 105° C. to 115° C. for 37 hours (it was confirmed that an IPC yield was 83.75% after 16 hours, 88.91% after 21 hours, and 93.12% after 37 hours). After diluting the mixture with water (17 mL) and ethyl acetate (11 mL), the mixture was filtered, and the filtered material was washed with ethyl acetate (4 mL, 3 times), then the aqueous layer and the organic layer were separated. Then, the aqueous layer was extracted with ethyl acetate (11 mL, 5 times), and the organic layer was combined with the previously obtained organic layer, washed with water (20 mL, 2 times), an aqueous solution of 10% $Na_2SO_4$, and concentrated to obtain a crude title compound (1.25 g, 61.27%, optical purity 95.6%).

Example 11C

The sealed-tube reaction was performed under conditions shown in the table below, and the reaction solvent was verified.

TABLE 27

| Ex. No. | Reagent (eq.) | | | | Reaction Condition Temp./Time | IPC (%) @6.91 min B |
|---|---|---|---|---|---|---|
| | A8-BR | $Cu_2O$ | $NH_3 \cdot H_2O$ | NMP | | |
| 11C-1 | 1.90 g (1.0 eq.) | 0.60 g (0.50 eq.) | 4.8 mL (2.5 v) | 1 mL (0.5 v) | 105-115° C./ 13 h | 63.97 |
| | | | | | 105-115° C./ 37 h | 82.32 |
| 11C-2 | 2.07 g (1.0 eq.) | 0.66 g (0.51 eq.) | 5.2 mL (2.5 v) | 2 mL (1 v) | 105-115° C./ 13 h | 66.46 |
| | | | | | 105-115° C./ 37 h | 93.75 |
| 11C-3 | 1.90 g (1.0 eq.) | 0.60 g (0.50 eq.) | 4.8 mL (2.5 v) | 2.9 mL (1.5 v) | 105-115° C./ 13 h | 70.34 |
| | | | | | 105-115° C./ 37 h | 93.10 |

In Example 11C-2, 0.74 g (yield 50%) of (R)-8-amino-1,2,3,4-tetrahydronaphthalen-2-ol was obtained, and in Example 11C-3, 0.5 g (36.6%) of (R)-8-amino-1,2,3,4-tetrahydronaphthalen-2-ol was obtained.

Example 11D

The sealed-tube reaction was performed under conditions shown in the table below, and an amount of the ammonia water was verified.

TABLE 28

| Ex. No. | Reagent (eq.) | | | | Reaction Condition Temp./Time | IPC (%) @6.83 min (B)-Rac |
|---|---|---|---|---|---|---|
| | (A8-BR-Rac) | $Cu_2O$ | $NH_3 \cdot H_2O$ | NMP | | |
| 11D-1 | 3.00g | 0.96 g (0.51 eq.) | 7.5 mL (2.5 v) | 3 mL (1 v) | 105-115° C./ 21 h | 91.85 |
| 11D-2 | 3.00g | 0.96 g (0.51 eq.) | 10.5 mL (3.5 v) | 3 mL (1 v) | 105-115° C./ 21 h | 92.93 |

In the table, (B)-Rac means a racemic compound represented by Formula (B).

Example 11E (R)-8-bromo-1,2,3,4-tetrahydronaphthalen-2-ol (Formula (A8-BR)) (3.00 g) obtained by an enzymatic reduction in the same manner as in the methods of Example 10A to Example 10D, $Cu_2O$ (0.96 g, 0.51 eq), NMP (3 mL, 1 v), and ammonia water (10.5 mL, 3.5 v) were mixed in a sealed-tube reactor, and a sealed-tube reaction was performed at a temperature of 105° C. to 115° C. for 21 hours (some parts of the reaction solution were sampled and subjected to HPLC analysis, and it was confirmed that an IPC yield was 92.93%). After cooling the reaction solution, an aqueous solution of 25 wt % sodium chloride (23 mL) and 2-methyltetrahydrofuran (2-MeTHF) (15 mL) were added to the reaction solution and the mixed solution was filtered, then the filtered material was washed with 2-MeTHF (15 mL). The aqueous layer and the organic layer were separated, and the aqueous layer was extracted with 2-MeTHF (15 mL, 4 times), then the organic layer was combined with the previously obtained organic layer, washed with an aqueous solution of 10 wt % $Na_2SO_4$ (15 mL), then decolorized through a CUNO (trademark) (filter) over 1 hour. The CUNO was washed with 2-MeTHF (15 mL), and the solvent was concentrated, then isopropyl acetate (6 mL) was added, and n-heptane (1.5 mL) was added dropwise at a temperature of 30° C. to 40° C., and the mixture was stirred at the same temperature for 0.5 hours. Furthermore, n-heptane (10.5 mL) was added dropwise, and the mixture was stirred at a temperature of 30° C. to 40° C. for 0.5 hours. Furthermore, n-heptane (3.0 mL) was added dropwise, and the mixture was stirred at a temperature of 30° C. to 40° C. for 0.5 hours. Furthermore, n-heptane (3.0 mL) was added dropwise, and the mixture was stirred at a temperature of 30° C. to 40° C. for 0.5 hours. The mixed solution described above was cooled at 20° C. for 30 minutes and stirred at a temperature of 15° C. to 25° C. for 1 hour. The mixed solution was filtered, and the filtered material was washed with n-heptane (3 mL) and dried to obtain the title compound (1.375 g, 60.1%).

Example 11F (R)-8-bromo-1,2,3,4-tetrahydronaphthalen-2-ol (Formula (A8-BR)) (16.32 g, NMP solution, content 61.1%) obtained by an enzymatic reduction in the same manner as in the methods of Example 10A to Example 10D, $Cu_2O$ (3.18 g, 0.51 eq), NMP (5 mL, 0.5 v), and ammonia water (35 mL, 3.5 v) were mixed in a sealed-tube reactor, and a sealed-tube reaction was performed at a temperature of 105° C. to 115° C. for 40 hours (it was confirmed that an IPC yield at 40 hours was 90.16%). After cooling the reaction solution, an aqueous solution of 25 wt % sodium chloride (75 mL) and 2-MeTHF (50 mL) were added to the reaction solution, and the mixed solution was filtered using diatomite (diatomaceous earth) (20.00 g), then the filtered material (cake) was washed with 2-MeTHF (50 mL). The aqueous layer and the organic layer were separated, and the aqueous layer was extracted with 2-MeTHF (50 mL, 2 times), then the organic layer was combined with the previously obtained organic layer, washed with an aqueous solution of 8 wt % $Na_2SO_4$ (50 mL, 2 times), and the organic layer (92.5% of a total amount) was taken out, then an aqueous solution of 0.5 M hydrochloric acid (111 mL) was added dropwise at 5° C. to 15° C. (in this case, pH=1.2). The aqueous layer and the organic layer were separated, and the aqueous layer was extracted with 2-MeTHF (30 mL). An aqueous solution of 10% sodium hydroxide (22 mL) was added to the aqueous layer, and the aqueous layer was extracted with 2-MeTHF (100 mL, 50 mL, 50 mL). After combining with the previously obtained organic layer, the organic layer was concentrated at 40° C. or lower, and n-heptane (80 mL) was added dropwise at 35° C. to 45° C., then the mixture was cooled to 5° C. Thereafter, the mixture was stirred at 0° C. to 10° C. for 24 hours and collected by filtration, and the filtered material was washed with n-heptane (10 mL) and dried to obtain the title compound (4.50 g, 67.8%, optical purity 99.9%).

Example 11G

The sealed-tube reaction was performed under conditions shown in the table below.

TABLE 29

| Ex. | (A8-BR) | Reagent (eq.) $Cu_2O$ | $NH_3 \cdot H_2O$ | NMP | Reaction Condition Temp./Time | IPC (%) @7.34 min (B) |
|---|---|---|---|---|---|---|
| 11G-1 | 72.44 g (NMP solution, content 63.8%) | 14.56 g (0.50 eq.) | 162 mL (3.5 v) | 23 mL (0.5 v) | 105-115° C./ 20 h | 90.87 |
| 11G-2 | 78.39 g (NMP solution, content 63.8%) | 15.78 g (0.50 eq.) | 175 mL (3.5 v) | 25 mL (0.5 v) | 105-115° C./ 20 h | 89.60 |

(Work up 11G-1)
After the reaction of Example 11G-1 was completed and the reaction solution was cooled, an aqueous solution of 25 wt % sodium chloride (345 mL) and 2-MeTHF (250 mL) were added to the reaction solution, and the mixed solution was filtered using diatomite, then the filtered material (cake) was washed with 2-MeTHF (230 mL). The aqueous layer and the organic layer were separated, and the aqueous layer was extracted with 2-MeTHF (230 mL, 2 times), then the organic layer was combined with the previously obtained organic layer to obtain the organic phase (11G-1).

(Work up 11G-2)
After the reaction of Example 11G-2 was completed and the reaction solution was cooled, an aqueous solution of 25 wt % sodium chloride (375 mL) and 2-MeTHF (250 mL) were added to the reaction solution, and the mixed solution was filtered using diatomite, then the filtered material (cake) was washed with 2-MeTHF (250 mL). The aqueous layer and the organic layer were separated, and the aqueous layer was extracted with 2-MeTHF (250 mL, 2 times), then the organic layer was combined with the previously obtained organic layer to obtain the organic phase (11G-2).

(Work up 11G-3)
After mixing the previously obtained organic phase (11G-1) and organic phase (11G-2), the mixture was washed with an aqueous solution of 8 wt % $Na_2SO_4$ (480 mL, 2 times), then an aqueous solution of 0.5 M hydrochloric acid (1,156 mL) was added dropwise, and a pH was adjusted to 0.88. The aqueous layer and the organic layer were separated, and the aqueous layer was extracted with 2-MeTHF (290 mL). An aqueous solution of 10% sodium hydroxide (230 mL) was added to the aqueous layer, and the aqueous layer was extracted with 2-MeTHF (1,000 mL, 500 mL, 500 mL, 3 times). After combining with the previously obtained organic layer, the organic layer was concentrated at 40° C. or lower, and n-heptane (576 mL) was added dropwise at 35° C. to 45° C., and then the mixture was cooled to 0° C. to 10° C., stirred at the same temperature, collected by filtration, and the filtered material was washed with n-heptane (96 mL) and dried to obtain the title compound (53.55 g, 70.8%, optical purity 99.9%).

[Data of Physical Properties of Formula (B)]
($^1$H-NMR, 400 MHz, manufacturer: Bruker, $CDCl_3$, δ ppm) 6.91 (1H, t, J=7 Hz), 6.52-6.46 (2H, m), 4.19-4.04 (2H, m), 3.51 (1H, brs), 2.93-2.65 (3H, m), 2.31 (1H, dd, J=7.16 Hz), 2.02-1.89 (1H, m), 1.85-1.65 (1H, m)

The ammonia water used in (Example 11A) to (Example 11G) is 25% to 28% ammonia water.

(Example 12A) to (Example 12B) Synthesis of (E)-2-(7-trifluoromethylchroman-4-ylidene)-N-[(7R)-7-hydroxy-5,6,7,8-tetrahydronaphthalen-1-yl]acetamide

[C108]

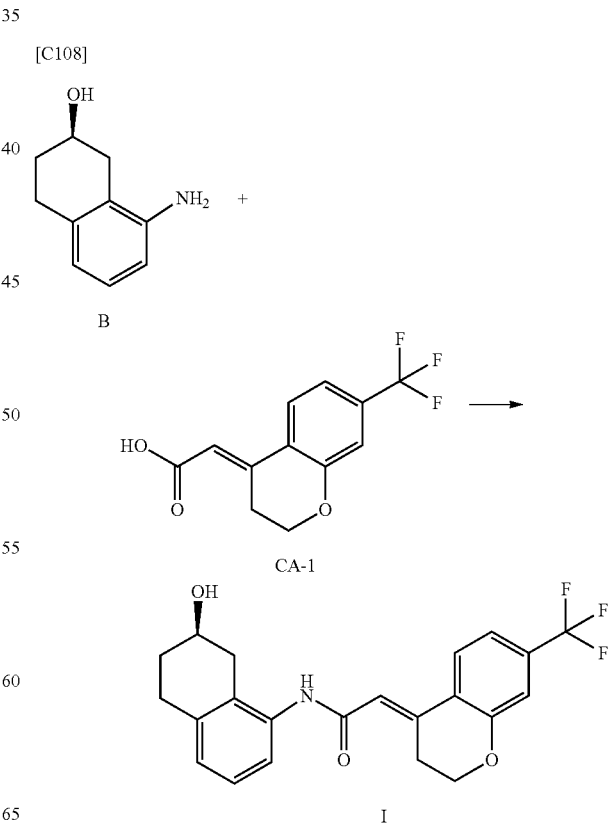

Example 12A

A condensation reaction (reaction conditions: 20° C. to 25° C., stirring for 17 hours) was performed using (R)-8-amino-1,2,3,4-tetrahydronaphthalen-2-ol (3 g) obtained in the same operation as that in (Example 11G), (E)-2-(7-(trifluoromethyl)chroman-4-ylidene)acetic acid (4.83 g, 1.0 eq) obtained by a production method disclosed in WO 2007/010383, isopropanol (60.01 g: 20 times its weight with respect to the compound represented by Formula (B)), and 4-(4,6-dimethoxy-1,3,5-triazin-2-yl)-4-methylmorpholinium chloride (DMT-MM) (6.67 g, 1.3 eq). After adding water (75 mL) to the reaction solution, the mixed solution was cooled to 10° C. to 15° C., stirred at the same temperature for 1 hour, filtered, and the filtered material was washed with water and dried at 36° C. for 16 hours. 2-MeTHF (90 g) was added to the obtained filtered material, and the mixture was stirred at 70° C. to 80° C. for 0.5 hours, then the solution was concentrated under reduced pressure at 40° C. or lower until a volume of the solution was 6 mL. Subsequently, after stirring the concentrated solution at 70° C. to 80° C. for 1 hour, it was cooled to 0° C. to 5° C., and 60 g of n-heptane was added dropwise at the same temperature, then the mixture was further stirred at the same temperature for 30 minutes. The mixture was collected by filtration, and the filtered material was washed with n-heptane (9 g), and dried to obtain the title compound (5.96 g, optical purity 99.9%).

(Example 12B) [Scale-up]

A condensation reaction (reaction conditions: 20° C. to 25° C., stirring for 13 hours) was performed using (R)-8-amino-1,2,3,4-tetrahydronaphthalen-2-ol (44.5 g) obtained in the same operation as that in (Example 11G), (E)-2-(7-(trifluoromethyl)chroman-4-ylidene)acetic acid (72.5 g, 1.0 eq) obtained by a production method disclosed in WO 2007/010383, isopropanol (900 g: 18 times its weight with respect to the compound represented by Formula (B)), and 4-(4,6-dimethoxy-1,3,5-triazin-2-yl)-4-methylmorpholinium chloride (DMT-MM) (100.05 g, 1.3 eq). A work up was performed according to (Example 12a), and thereby the title compound (95.7 g, optical purity 100%) was obtained.

[Data of Physical Properties of Compound Represented by Formula (I)]

($^1$H-NMR data (CDCl$_3$) (δ: ppm)):
7.80-7.58 (m, 1H), 7.24-6.92 (m, 5H), 6.45 (s, 1H), 4.29 (t, 2H, J=6 Hz), 4.28-4.15 (m, 1H), 3.51 (t, 2H, J=5 Hz), 3.10-2.78 (m, 3H), 2.69-2.53 (m, 1H), 2.14-2.00 (m, 1H), 1.90-1.67 (m, 2H)

(LC-MS):
RT=4.73 (minutes), [M+H]$^+$=404

An optical purity of the compound represented by Formula (I) was measured using a HPLC LC-VP system of Shimadzu Corporation under the following conditions.

TABLE 30

| | |
|---|---|
| Column | CHIRALCEL AD-H ID 4.6 × 250 mm (Daicel) |
| Elution solvent | Ethanol |
| Flow rate | 0.5 mL/min |
| Column temperature | 40° C. |
| Measurement wavelength | 254 nm |
| Elution time | Compound represented by (I) - 10.5 minutes, Enantiomer of compound represented by (I) - 18.6 minutes |

EXPLANATION OF REFERENCES

L1, L2, L3, L4: Nitrogen inlet
M1: Vessel containing raw material, TEMPO, and dichloromethane
M2: Vessel containing KBr, NaHCO$_3$, and water
M3: Vessel containing NaClO
P1, P2, P3: Pump
T1, T2, T3: Pre-cooling tube
S1, S2, S3: Stirrer
R1, R2, R3: Reactor
CD: Recovery drum

The invention claimed is:

1. A method for producing a compound represented by Formula (I), the method comprising:
   asymmetrically reducing a keto group of a compound represented by Formula (SM8) to obtain a compound represented by Formula (A8);
   reacting the compound represented by Formula (A8) with ammonia water in the presence of a catalyst selected from the group consisting of Pd$_2$(dba)$_3$, PdCl$_2$-Josiphos complex, CuI, Cu(OAc)$_2$, Cu$_2$O, CuO, CuBr, CuCl, CuSO$_4$, and CuFe$_2$O$_4$ to obtain a compound represented by Formula (B); and
   causing a condensation reaction of the compound represented by Formula (B) or a salt thereof and a compound represented by Formula (CA-1) by using DMT-MM (4-(4,6-dimethoxy-1,3,5-triazin-2-yl)-4-methylmorpholinium chloride) as a condensation agent to obtain the compound represented by Formula (I), Formula (I)

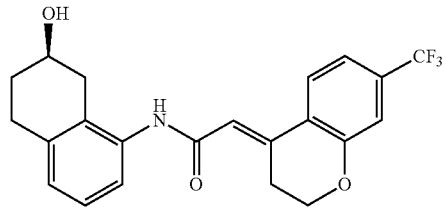

(I)

Formula (SM8)

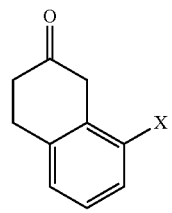

(SM8)

in Formula (SM8), X is a halogen atom,

Formula (A8)

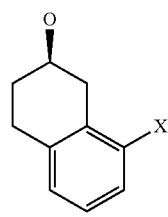

(A8)

in Formula (A8), X is a halogen atom,

-continued

Formula (B)

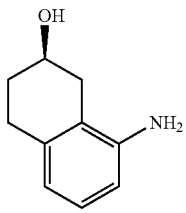
(B)

Formula (CA-1)

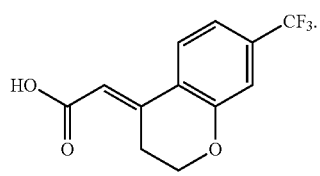
(CA-1)

2. A method for producing a compound represented by Formula (I), the method comprising:

reacting a compound represented by Formula (A8) with ammonia water in the presence of a catalyst selected from the group consisting of $Pd_2(dba)_3$, $PdCl_2$-Josiphos complex, CuI, $Cu(OAc)_2$, $Cu_2O$, CuO, CuBr, CuCl, $CuSO_4$, and $CuFe_2O_4$ to obtain a compound represented by Formula (B); and causing a condensation reaction of the compound represented by Formula (B) or a salt thereof and a compound represented by Formula (CA-1) by using DMT-MM (4-(4,6-dimethoxy-1,3,5-triazin-2-yl)-4-methylmorpholinium chloride) as a condensation agent to obtain the compound represented by Formula (I), Formula (I)

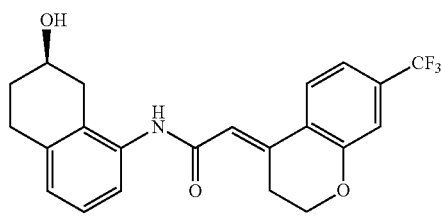
(I)

Formula (A8)

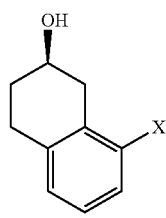
(A8)

in Formula (A8), X is a halogen atom,

-continued

Formula (B)

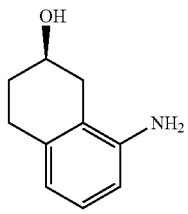
(B)

Formula (CA-1)

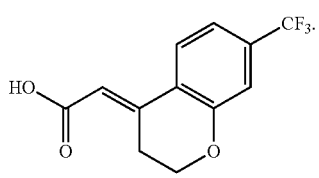
(CA-1)

3. A method for producing a compound represented by Formula (I), the method comprising:

causing a condensation reaction of a compound represented by Formula (B) or a salt thereof and a compound represented by Formula (CA-1) by using DMT-MM (4-(4,6-dimethoxy-1,3,5-triazin-2-yl)-4-methylmorpholinium chloride) as a condensation agent to obtain the compound represented by Formula (I), Formula (I):

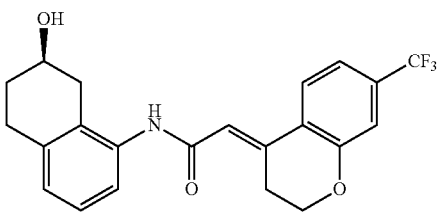
(I)

Formula (B):

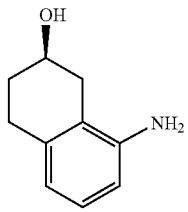
(B)

Formula (CA-1):

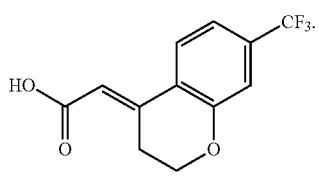
(CA-1)

4. A method for producing a compound represented by Formula (B), the method comprising:

asymmetrically reducing a keto group of a compound represented by Formula (SM8) to obtain a compound represented by Formula (A8); and reacting the compound represented by Formula (A8) with ammonia water in the presence of a catalyst selected from the group consisting of Pd$_2$(dba)$_3$, PdCl$_2$-Josiphos complex, CuI, Cu(OAc)$_2$, Cu$_2$O, CuO, CuBr, CuCl, CuSO$_4$, and CuFe$_2$O$_4$ to obtain the compound represented by Formula (B), Formula (B):

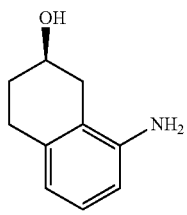
(B)

Formula (SM8):

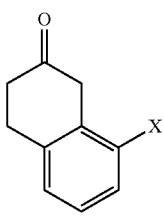
(SM8)

in Formula (SM8), X is a halogen atom,

Formula (A8):

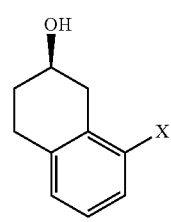
(A8)

in Formula (A8), X is a halogen atom.

5. A method for producing a compound represented by Formula (B), the method comprising:
reacting a compound represented by Formula (A8) with ammonia water in the presence of a catalyst selected from the group consisting of Pd$_2$(dba)$_3$, PdCl$_2$-Josiphos complex, CuI, Cu(OAc)$_2$, Cu$_2$O, CuO, CuBr, CuCl, CuSO$_4$, and CuFe$_2$O$_4$ to obtain the compound represented by Formula (B), Formula (B):

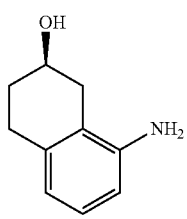
(B)

Formula (A8):

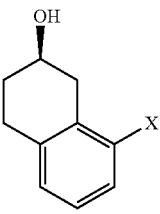
(A8)

in Formula (A8), X is a halogen atom.

6. A method for producing a compound represented by Formula (A8), the method comprising:
asymmetrically reducing a keto group of a compound represented by Formula (SM8) to obtain the compound represented by Formula (A8), Formula (A8)

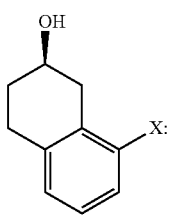
(A8)

in Formula (A8), X is a halogen atom,

Formula (SM8)

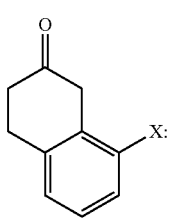
(SM8)

in Formula (SM8), X is a halogen atom.

7. The method according to claim 6, wherein the step of asymmetrically reducing a keto group of a compound represented by Formula (SM8) uses ketone reductase to obtain the compound represented by Formula (A8).

* * * * *